(12) United States Patent
Mao et al.

(10) Patent No.: US 10,246,461 B2
(45) Date of Patent: Apr. 2, 2019

(54) DOSAGE FORM COMPOSITIONS COMPRISING AN INHIBITOR OF BRUTON'S TYROSINE KINASE

(71) Applicant: Genentech, Inc., South San Francisco, CA (US)

(72) Inventors: Chen Mao, Foster City, CA (US); Dawen Kou, Millbrae, CA (US); Po-Chang Chiang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/442,774

(22) Filed: Feb. 27, 2017

(65) Prior Publication Data

US 2017/0247381 A1 Aug. 31, 2017
US 2018/0251462 A2 Sep. 6, 2018

Related U.S. Application Data

(60) Provisional application No. 62/301,373, filed on Feb. 29, 2016.

(51) Int. Cl.
| | |
|---|---|
| *A61K 31/498* | (2006.01) |
| *A61K 47/12* | (2006.01) |
| *A61K 9/20* | (2006.01) |
| *C07D 487/04* | (2006.01) |
| *C07C 309/04* | (2006.01) |
| *A61K 9/14* | (2006.01) |
| *A61K 31/4985* | (2006.01) |

(52) U.S. Cl.
CPC .......... *C07D 487/04* (2013.01); *A61K 9/146* (2013.01); *A61K 9/2013* (2013.01); *A61K 31/4985* (2013.01); *C07C 309/04* (2013.01); *C07B 2200/13* (2013.01)

(58) Field of Classification Search
CPC .................................................. A61K 31/4985
See application file for complete search history.

(56) References Cited

U.S. PATENT DOCUMENTS

| | | |
|---|---|---|
| 6,287,599 B1 | 9/2001 | Burnside et al. |
| 8,716,274 B2 | 5/2014 | Crawford et al. |
| 8,729,072 B2 | 5/2014 | Crawford et al. |
| 8,735,392 B2 | 5/2014 | Wang et al. |
| 8,921,353 B2 * | 12/2014 | Crawford ............. A61K 31/496 514/210.21 |
| 9,238,655 B2 * | 1/2016 | Crawford ............. A61K 31/496 |
| 9,782,405 B2 * | 10/2017 | Crawford ............. A61K 31/496 |
| 2008/0160080 A1 | 7/2008 | Jacobs et al. |
| 2010/0310648 A1 | 12/2010 | Packhaeuser et al. |
| 2013/0116235 A1 * | 5/2013 | Crawford ............. A61K 31/496 514/210.21 |

OTHER PUBLICATIONS

Budha et al., "Drug absorption interactions between oral targeted anticancer agents and PPIs: is pH-dependent solubility the Achilles heel of targeted therapy?" Clin. Pharmacol. Ther. Aug. 2012;92(2):203-13. PubMed PMID: 22739140. (Year: 2012).*
International Search Report and Written Opinion for PCT/EP2017/054435, dated May 12, 2017, 10 pages.
Badawy et al., "Formulation of Solid Dosage Forms to Overcome Gastric pH Interaction of the Factor Xa Inhibitor, BMS-561389", Pharmaceutical Research, May 2006, vol. 23, No. 5, pp. 989-996.
Badawy et al., "Microenvironmental pH Modulation in Solid Dosage Forms", Journal of Pharmaceutical Sciences, May 2007, vol. 96, No. 5, pp. 948-959.
Menning et al., "Fumaric Acid Microenvironmental Tablet Formulation and Process Development for Crystalline Cenicriviroc Mesylate, a BCS IV Compound", Molecular Pharmaceutics, 2013, vol. 10, pp. 4005-4015.
Mitra et al., "Using Absorption Simulation and Gastrick pH modulated Dog Model for Formulation Development to OVercome Achlorhydria Effect", 2011, vol. 8, pp. 2216-2223.
Mitra et al., "Impaired Drug Absorption Due to High Stomach pH: A Review of Strategies for Mitigation of Such Effect to Enable Pharmaceutical Product Development", Molecular Pharmaceutics, 2013, vol. 10, pp. 3970-3979.
Adachi et al., "Improved dissolution and absorption of ketoconazole in the presence of organic acids as pH-modifiers", European Journal of Pharmaceutical Sciences, 2015, vol. 76, pp. 225-230.
Onoue et al., "Improved dissolution and pharmacokinetic behavior of dipyridamole formulation with microenvironmental pH-modifier under hypochlorhydria", International Journal of Pharmaceutics, 2012, vol. 426, pp. 61-66.
Taniguchi et al., "Microenvironmental pH-modification to improve dissolution behavior and oral absorption for drugs with pH-dependent solubility", Expert Opinion Drug Delivery, 2014, vol. 11, No. 4, pp. 505-516.

* cited by examiner

*Primary Examiner* — Theodore R. West
(74) *Attorney, Agent, or Firm* — Armstrong Teasdale LLP

(57) ABSTRACT

The invention relates generally to pharmaceutical tablet compositions comprising fumaric acid and the compound (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one free base that is an inhibitor of Bruton's tyrosine kinase. The invention further relates to amorphous solid dispersions comprising at least one polymer and the Bruton's kinase inhibitor free base compound. The invention further relates to crystalline mesylate salts, crystalline chloride salts and crystalline sulfate salts of the Bruton's kinase inhibitor free base compound. In some aspects, the crystalline salts are single polymorphs.

11 Claims, 31 Drawing Sheets

DOSAGE FORM COMPOSITIONS COMPRISING AN INHIBITOR OF BRUTON'S TYROSINE KINASE

CROSS-REFERENCE TO RELATED APPLICATION

This application claims priority benefit of U.S. Provisional Application Ser. No. 62/301,373 filed on Feb. 29, 2016, which is incorporated herein in its entirety.

FIELD OF THE DISCLOSURE

The field of the disclosure relates generally to pharmaceutical dosage form compositions comprising compounds which inhibit Bruton's Tyrosine Kinase (Btk) activity which are useful for treating disorders mediated by Btk including inflammation, immunological diseases, and cancer.

BACKGROUND

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis. A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production). Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (Di Paolo et al (2011) Nature Chem. Biol. 7(1):41-50; Liu et al (2011) Jour. of Pharm. and Exper. Ther. 338(1):154-163). In addition, Btk has been reported to play a role in apoptosis; thus, inhibition of Btk activity can be useful for cancer, as well as the treatment of B-cell lymphoma, leukemia, and other hematological malignancies. Moreover, given the role of Btk in osteoclast function, the inhibition of Btk activity can be useful for the treatment of bone disorders such as osteoporosis. Specific Btk inhibitors have been reported (Liu (2011) Drug Metab. and Disposition 39(10):1840-1849; U.S. Pat. No. 7,884,108, WO 2010/056875; U.S. Pat. Nos. 7,405,295, 7,393,848; WO 2006/053121; U.S. Pat. No. 7,947,835; US 2008/0139557; U.S. Pat. No. 7,838,523; US 2008/0125417; US 2011/0118233; PCT/US2011/050034 "PYRIDINONES/PYRAZINONES, METHOD OF MAKING, AND METHOD OF USE THEREOF", filed 31 Aug. 2011; PCT/US2011/050013 "PYRIDAZINONES, METHOD OF MAKING, AND METHOD OF USE THEREOF", filed 31 Aug. 2011; U.S. Ser. No. 13/102,720 "PYRIDONE AND AZA-PYRIDONE COMPOUNDS AND METHODS OF USE", filed 6 May 2011).

U.S. Pat. No. 8,716,274 (incorporated by reference herein in its entirety) discloses classes of heteroaryl pyridine and aza-pyridone compounds useful for inhibiting Btk. Compound (A) depicted below is one particular Btk inhibitor compound, where the asterisk refers to a chiral center:

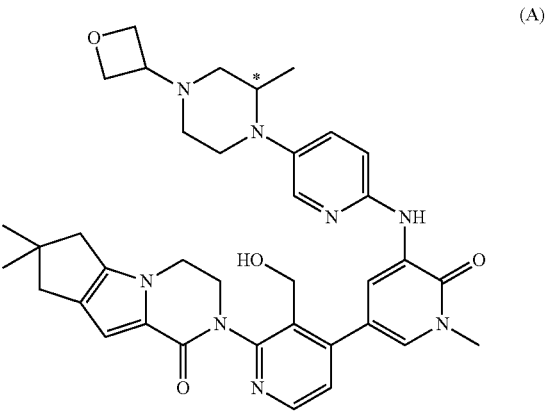 [SMILES: CC1CN(C2COC2)CCN1c1ccc(Nc2cc(-c3ccnc(N4CCn5c(cc6c5CC(C)(C)C6)C4=O)c3CO)cn(C)c2=O)nc1]

(A)

The S enantiomer of compound (A) is: (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrrol[1,2-a]pyrazin-1-one. The R enantiomer of compound (A) is: (R)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one.

Compound (A) is a weak base exhibiting a pH-dependent solubility profile having an aqueous solubility of about 6.5 mg/mL at pH 2.6 and a solubility of about 0.001 mg/mL at pH 5.0. Many patients that could benefit from treatment with Btk inhibitors take a stomach acid reducing agent ("ARA") such as a proton pump inhibitor ("PPI") for the treatment of gastric reflux disease. Problematically, such patients may be achlorhydric and exhibit a stomach pH of from about 4 to about 6 thereby reducing the solubility and concomitant bioavailability of weak base Bkt inhibitors such as compound (A). Thus there may be decreased drug exposure in patients taking ARAs.

A need therefore exists for compositions that mitigate pH-dependent solubility risks associated with compound (A) and that provide for improved bioavailability in patients exhibiting achlorohydria.

BRIEF DESCRIPTION

In some aspects, tablet compositions are provided. The tablets comprise from about 25 mg to about 300 mg of a free base of structure (I)

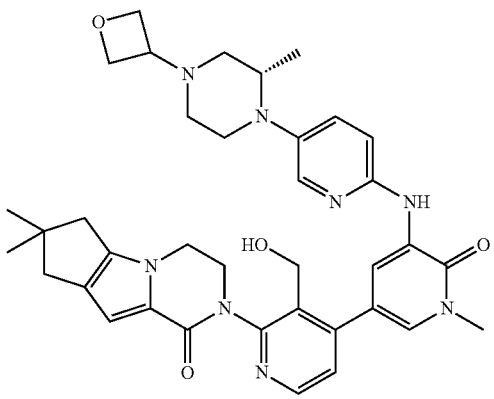

(I)

and from about 5 wt. % to about 50 wt. % fumaric acid.

In some aspects, salt compositions are provided. The salt compositions comprise a cation formed from a free base of structure (I) recited above and an anion, such as an anion selected from mesylate, chloride and sulfate.

In some aspects, amorphous solid dispersion compositions are provided. The compositions comprise a polymeric component and from about 20 wt. % to about 60 wt. % of a free base of structure (I) recited above.

In some other aspects, pharmaceutical compositions comprising: (i) the combination of from about 25 mg to about 300 mg of a free base of structure (I) and from about 5 wt. % to about 50 wt. % fumaric acid, (ii) salt compositions comprising a cation formed from a free base of structure (I) and an anion selected from mesylate, chloride and sulfate, or (iii) amorphous solid dispersions comprising a polymeric component and from about 20 wt. % to about 60 wt. % of a free base of structure (I) are provided.

In other aspects, a method of treating a condition selected from immune disorders, cancer, cardiovascular disease, viral infection, inflammation, metabolism/endocrine function disorders and neurological disorders in an achlorhydric patient is provided. The method comprises administering a pharmaceutical composition as previously described to a patient in need of such treatment.

In other aspects, a kit for treating a condition selected from immune disorders, cancer, cardiovascular disease, viral infection, inflammation, metabolism/endocrine function disorders and neurological disorders in an achlorhydric patient is provided. The kit comprises: (1) a pharmaceutical composition as previously described; and (2) instructions for use.

DETAILED DESCRIPTION

Figure 1:
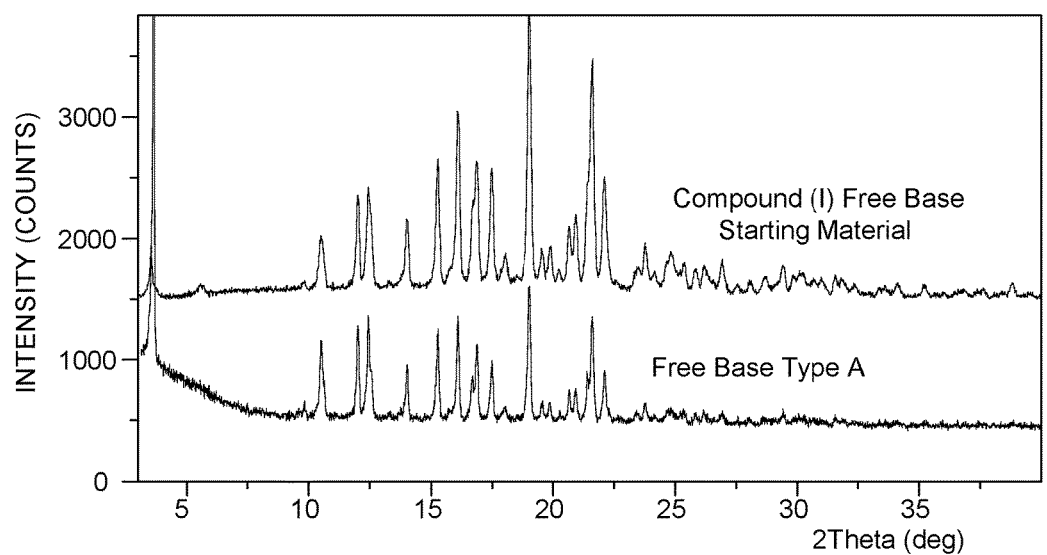
FIG. 1 provides an overlay of powder X-ray diffraction (XRPD) patterns of compound (I) free base Type A crystals used in some of the examples herein and compound (I) free base Type A crystal standard.

Reference will now be made in detail to certain aspects of the disclosure, examples of which are illustrated in the accompanying structures and formulas. While the disclosure will be described in conjunction with the enumerated aspects, it will be understood that they are not intended to limit the invention to those aspects. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this disclosure belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

The disclosure is directed to pharmaceutical compositions comprising the S-enantiomer of compound (A): (S)-2-(3'-(hydroxymethyl)-1-methyl-5-((5-(2-methyl-4-(oxetan-3-yl) piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one, depicted below as compound (I), in the form of a free base or a salt.

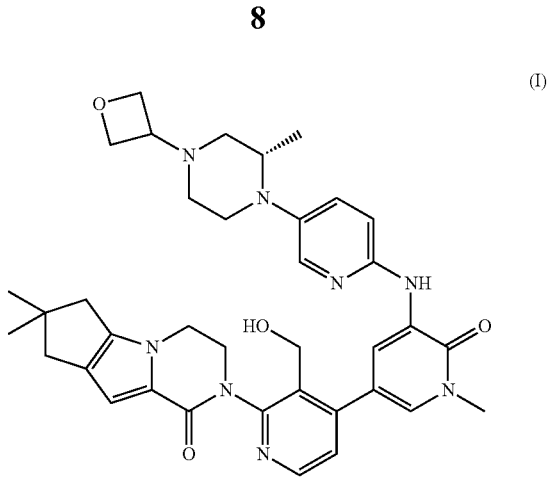

(I)

Some aspects of the disclosure relate to tablet compositions comprising compound (I) free base in combination with fumaric acid. Some other aspects of the disclosure relate to salt compositions comprising a cation formed from compound (I) free base. Some further aspects of the disclosure relate to amorphous solid dispersions comprising compound (I) free base and a polymeric component. Each of the various compositions of the disclosure provide for improved dissolution of compound (I) at a pH of from about 4 to about 6 as compared to compound (I) free base alone.

Definitions

As used herein "achlorohydria" and "achlorohydric" refer to states where the production of hydrochloric acid in gastric secretions of the stomach and other digestive organs is low or absent. A typical stomach pH associated with achlorohydria is from about 4 to about 6. In some aspects of the disclosure, achlorohydria may result from the use of antacids or drugs that decrease gastric acid production (such as H2-receptor antagonists) or transport (such as proton pump inhibitors ("PPI")).

As used herein, the term "amorphous" or "amorphous form" is intended to mean that the substance, component, or product in question is not essentially crystalline as determined, for instance, by XRPD or where the substance, component, or product in question, for example is not birefringent when viewed microscopically. In certain aspects, a sample comprising an amorphous form of a substance may be essentially free of other amorphous forms and/or crystalline forms.

As used herein, the term "amorphous solid dispersion" ("ASD") refer to compositions having an amorphous active ingredient essentially dispersed in a polymer or mixture of polymers.

As used herein "essentially" refers to at least 80%, at least 85%, at least 90%, at least 95% or at least 99% on a specified basis.

As used herein, the terms "crystalline" and "crystal" refer to a crystalline solid form of a chemical compound, including, but not limited to, a single-component or multiple-component crystal form, e.g., a polymorph of a compound; or a solvate, a hydrate, a clathrate, a co-crystal, a salt of a compound, or a polymorph thereof. The term "crystal forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

Techniques for characterizing crystal forms and amorphous forms are known in the art and include, but are not limited to, thermogravimetric analysis ("TGA"), differential scanning calorimetric ("DSC"), X-ray powder diffraction ("XRPD"), single crystal X-ray diffractometry, vibrational spectroscopy, e.g., IR and Raman spectroscopy, solid-state nuclear magnetic resonance ("NMR"), optical microscopy, hot stage optical microscopy, scanning electron microscopy ("SEM,") electron crystallography and quantitative analysis, particle size analysis ("PSA"), surface area analysis, solubility studies and dissolution studies.

As used herein, the terms "polymorph" and "polymorphic form" refer to one of two or more crystal forms that comprise the same molecule, molecules or ions. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs).

As used herein, the term "stereomerically pure" means a composition that comprises one stereoisomer of a compound and is essentially free of other stereoisomers of that compound. In certain aspects, stereomerically pure Compound (I) or a salt or solvate thereof is provided herein that is essentially free of the other stereoisomers including, for example, (R)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one. In certain aspects, a stereomerically pure compound comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, greater than about 97 percent by weight of one stereoisomer of the compound and less than about 3 percent by weight of the other stereoisomers, or greater than about 99 percent by weight of one stereoisomer of the compound and less than about 1 percent by weight of the other stereoisomers of the compound. In certain aspects, term "stereomerically pure" compound (I) means that the compound is made up of approximately 100% by weight of this particular stereoisomer. The above percentages are based on the total amount of combined stereoisomers of the compound.

In the description herein, if there is a discrepancy between a depicted structure and a name given to that structure, then the depicted structure controls. Additionally, if the stereochemistry of a structure or a portion of a structure is not indicated with, for example, bold wedged, or dashed lines, the structure or portion of the structure is to be interpreted as encompassing all stereoisomers of it. In some cases, however, where more than one chiral center exists, the structures and names may be represented as single enantiomers to help describe the relative stereochemistry As used herein, a crystalline or amorphous form that is "essentially pure" contains less than about 10 percent by weight of one or more other crystalline or amorphous form, less than about 5 percent by weight of one or more other crystalline or amorphous form, less than about 3 percent by weight of one or more other crystalline or amorphous form, less than about 1 percent by weight of one or more other crystalline or amorphous form, or less than about 0.5 percent by weight of one or more other crystalline or amorphous form. In certain contexts, as used herein, "essentially pure" compound (I) or a salt or solvate thereof can mean free of other chemical compounds, for example, unreacted precursors and side products that might be present in preparation processes. In other contexts, as used herein, a "essentially pure" solid form (e.g., crystalline form or amorphous form) of compound (I) or a salt or solvate thereof can mean free of other solid forms of compound (I) or salts or solvates thereof. As such, "essentially pure" compound (I) may comprise, in certain aspects, less than about 10%, 5%, 3%, 2%, 1%, 0.75%, 0.5%, 0.25%, or 0.1% by weight of one or more other crystal forms and amorphous forms of the compound and/or other chemical compounds. In certain aspects, a solid form that is essentially pure is essentially free of one or more other particular crystal forms, amorphous forms, and/or other chemical compounds.

The terms "treat" and "treatment" refer to therapeutic treatment, wherein the object is to slow down (lessen) an undesired physiological change or disorder, such as the development or spread of arthritis or cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present disclosure that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaI1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARGT™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

The term "package insert" is used to refer to instructions customarily included in commercial packages of therapeutic products, that contain information about the indications, usage, dosage, administration, contraindications and/or warnings concerning the use of such therapeutic products.

The term "pharmaceutically acceptable" refers to components or excipients which are not biologically or otherwise undesirable and which are compatible chemically and/or toxicologically, with the other ingredients comprising a formulation, and/or the mammal being treated therewith.

Tablets

Some aspects of the disclosure relate to pharmaceutical tablet compositions comprising compound (I) free base and an acid. In some aspects, the acid is an organic acid or an inorganic acid. In some aspects, the acid is an organic acid selected from fumaric acid, citric acid, succinic acid, and tartaric acid. In some particular aspects, the acid is fumaric acid.

The compound (I) free base content in the tablet composition is about 25 mg, about 50 mg, about 75 mg, about 100 mg, about 150 mg, about 200 mg, about 250 mg or about 300 mg, and ranges thereof, such as from about 25 mg to about 300 mg, from about 25 mg to about 200 mg, from about 25 mg to about 100 mg, from about 50 mg to about 150 mg, from about 100 mg to about 200 mg, from about 100 mg to about 300 mg, or from about 150 mg to about 250 mg. Based on tablet weight, the free base content in the tablet composition is about 5 wt. %, about 10 wt. %, about 15 wt. %, about 20 wt. %, about 25 wt. %, about 30 wt. %, about 35 wt. % or about 40 wt. %, and ranges thereof, such as from about 5 wt. % to about 40 wt. %, from about 10 wt. % to about 40 wt. %, from about 15 wt. % to about 35 wt. %, from about 15 wt. % to about 30 wt. %, or from about 20 wt. % to about 25 wt. %.

The organic acid (e.g., fumaric acid) content in the tablet composition is about 5 wt. %, about 10 wt. %, about 15 wt. %, about 20 wt. %, about 25 wt. %, about 30 wt. %, about 35 wt. %, about 40 wt. %, about 45 wt. % or about 50 wt. %, and ranges thereof, such as from about 5 wt. % to about 50 wt. %, from about 5 wt. % to about 40 wt. %, from about 5 wt. % to about 30 wt. %, from about 5 wt. % to about 20 wt. %, from about 10 wt. % to about 30 wt. %, from about 15 wt. % to about 25 wt. %, from about 20 wt. % to about 25 wt. %, from about 5 wt. % to about 15 wt. %, or from about 10 wt. % to about 15 wt. %. In some other aspects, fumaric acid is present as an extra-granular component in the tablet. In some other aspects, fumaric acid is present as an intra-granular component in the tablet. In some other aspects, fumaric acid may be present as both and intra-granular component and as an extra-granular component.

The weight ratio of the compound (I) free base to organic acid (fumaric acid) is about 1:5, about 1:4.5, about 1:4, about 1:3.5 about 1:3, about 1:2.5, about 1:2, about 1:1.5, about 1:1, about 1.5:1, about 2:1, about 2.5:1 or about 3:1, and ranges thereof, such as from about 1:5 to about 3:1, from about 1:1 to about 1:5, from about 1:2 to about 1:5, from about 1:3 to about 1:5, from about 1:3 to about 3:1, from about 1:2 to about 2:1, from about 1:1.5 to about 1.5:1, or from about 1.2:1 to about 1:1.2.

Tablet weight is suitably about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg or about 1500 mg.

In some aspects of the disclosure, the weight ratio of compound (I) free base to fumaric acid is about 1:5, about 1:4, about 1:3, about 1:2, about 1:1, from about 1:1 to about 1:5, from about 1:2 to about 1:5 or from about 1:3 to about 1:5. In such aspects, compound (I) free base content is about 25 mg, about 50 mg, about 75 mg or about 100 mg, from about 25 mg to about 100 mg or from about 25 mg to about 50 mg. In such aspects, as described in more detail elsewhere herein, the fumaric acid content in the tablet may be up to about 50 wt. %. In some other aspects of the disclosure, the weight ratio of compound (I) free base to fumaric acid is about 2:1, about 1.5:1, about 1.2:1, about 1:1, about 1:1.2, about 1:1.5 or about 1:2, and ranges thereof, such as from about 2:1 to about 1:2, from about 1.5:1 to about 1:1.5, or from about 1.2:1 to about 1:1.2. In such aspects, compound (I) free base content is about 100 mg, about 150 mg, about 200 mg, about 250 mg, about 300 mg, and ranges thereof, such as from about 100 mg to about 300 mg or from about 150 mg to about 250 mg.

The tablets of the present disclosure provide for improved compound (I) free base pharmacokinetics in humans exhibiting achlorhydria as compared to compound (I) free base formulated in the absence of an organic acid. In vivo human achlorhydria pharmacokinetics for a tablet dosage comprising 200 mg compound (I) free base are as follows. In some aspects, the terminal half-life (t½) is about 5 hours, about 10 hours, about 15 hours, about 20 hours, or about 25 hours, and ranges constructed from combinations of said values, for instance, from about 5 to about 25 hours, from about 5 to about 20 hours, or from about 5 to about 15 hours. In some aspects, the time to maximum plasma concentration (tmax) is about 0.5 hours, about 1 hour, about 2 hours, about 3 hours, or about 4 hours, and ranges constructed from combinations of said values, for instance, from about 0.5 to about 4 hours, from about 0.5 to about 3 hours, or from about 1 to about 3 hours. In some aspects, the maximum plasma concentration (Cmax) is about 80 ng/mL, about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 800 ng/mL, about 1000 ng/mL or about 1200 ng/mL, and ranges constructed from combinations of said values, for instance, from about 80 to about 1200 ng/mL, from about 200 to about 1000 ng/mL, or from about 400 to about 800 ng/mL. In some aspects, the plasma concentration after 12 hours (C12) is about 20 ng/mL, about 30 ng/mL, about 40 ng/mL, about 50 ng/mL, about 60 ng/mL, about 70 ng/mL or about 80 ng/mL, and ranges constructed from combinations of said values, for instance, from about 20 to about 80 ng/mL, from about 20 to about 60 ng/mL, or from about 30 to about 50 ng/mL. In some aspects, the area under the concentration curve over the time period of dosing to 12 hours (AUC0-12) is about 500 h*ng/mL, about 1000 h*ng/mL, about 1500 h*ng/mL, about 2000 h*ng/mL, or about 2500 h*ng/mL, and ranges constructed from combinations of said values, for instance, from about 500 to about 2500 h*ng/mL or 1000 to about 2000 h*ng/mL. In some aspects, the area under the concentration curve over the time period of dosing to 24 hours (AUC0-24) is about 800 h*ng/mL, about 1000 h*ng/mL, about 1500 h*ng/mL, about 2000 h*ng/mL, about 2500 h*ng/mL, about 3000 h*ng/mL, about 3500 h*ng/mL, or about 4000 h*ng/mL, and ranges constructed from combinations of said values, for instance, from about 800 to about 4000 h*ng/mL, from about 1500 to about 3000 h*ng/mL, or from about 2000 to about 3000 h*ng/mL. In some aspects, the area under the concentration curve over the time period of dosing to ∞ (72 hours) (AUC0-∞) is about 900 h*ng/mL, about 1500 h*ng/mL, about 2000 h*ng/mL, about 2500 h*ng/mL, about 3000 h*ng/mL, about 3500 h*ng/mL, about 4000 h*ng/mL, or about 4500 h*ng/mL, and ranges constructed from combinations of said values, for instance, from about 900 to about 4500 h*ng/mL, from about 1500 to about 4000 h*ng/mL, or from about 2000 to about 3000 h*ng/mL.

The tablet compositions of the present disclosure may further suitably comprise one or more pharmaceutically acceptable excipients selected from, but not limited to fillers (diluents), disintegrants, binders, glidants, and lubricants. A filler (or diluent) may be used to increase the bulk volume of the powdered drug making up the tablet. A disintegrant may be used to encourage the tablet to break down into small fragments, ideally individual drug particles, when it is ingested and thereby promote the rapid dissolution and absorption of drug. A binder may be used to ensure that granules and tablets can be formed with the required mechanical strength and hold a tablet together after it has been compressed, preventing it from breaking down into its component powders during packaging, shipping and routine handling. A glidant may be used to improve the flowability of the powder making up the tablet during production. A lubricant may be used to ensure that the tableting powder does not adhere to the equipment used to press the tablet during manufacture, to improve the flow of the powder during mixing and pressing, and to minimize friction and breakage as the finished tablets are ejected from the equipment.

Fillers and binders may include calcium hydrogenphosphate, microcrystalline cellulose (Avicel®), lactose, or any other suitable bulking agent. Examples of suitable fillers include microcrystalline cellulose, such as Avicel PH 101, Avicel PH102, Avicel PH 200, Avicel PH 105, Avicel DG, Ceolus KG 802, Ceolus KG 1000, SMCCSO and Vivapur 200; lactose monohydrate, such as Lactose FastFlo; microcrystalline cellulose co-processed with other excipients, such as microcrystalline cellulose coprocessed with lactose mono hydrate (MicroceLac 100) and microcrystalline cellulose co-processed with colloidal silicon dioxide (SM-CCSO, Prosolv 50 and Prosolv HD 90); mixtures of isomaltulose derivatives such as galenIQ; and other suitable fillers and combinations thereof. The filler may be present as an intra-granular component and/or as an extra-granular component. In some particular aspects, the tablet compositions of the present disclosure comprise lactose and microcrystalline cellulose.

Disintegrants may be included in the disclosed formulations to promote separation of the granules within the compact from one another and to maintain separation of the liberated granules from one another. Distintegrants may be present as an intra-granular component and/or as an extra-granular component. Disintegrants may include any suitable disintegrant such as, for example, crosslinked polymers such as cross-linked polyvinyl pyrrolidone and cross-linked sodium carboxymethylcellulose or croscarmellose sodium. In some particular aspects, the disintegrant is croscarmellose sodium. The disintegrant content is suitably about 1 wt. %, about 1.5 wt. %, about 2 wt. %, about 2.5 wt. %, about 3 wt. %, about 3.5 wt. %, about 4 wt. %, about 4.5 wt. %, or about 5 wt. %, and ranges thereof, such as from about 1 wt. % to about 5 wt. %, or from about 2 wt. % to about 4 wt. %.

Glidants may include, for example, colloidal silicon dioxide, including highly dispersed silica (Aerosil®), or any other suitable glidant such as animal or vegetable fats or waxes. In some particular aspects, the glidant is fumed silica. The glidant content is suitably about 0.1 wt. %, about 0.5 wt. %, about 1 wt. %, about 1.5 wt. %, about 2 wt. %, about 2.5 wt. % or about 3 wt. %, and ranges thereof, such as from about 0.1 wt. % to about 3 wt. %, from about 0.5 wt. % to about 2 wt. %, from about 0.5 wt. % to about 1.5 wt. %.

Lubricants may be used in compacting granules in the pharmaceutical composition. Lubricants may include, for example, polyethylene glycol (e.g., having a molecular weight of from about 1000 to about 6000), magnesium and calcium stearates, sodium stearyl fumarate, talc, or any other suitable lubricant. In some particular aspects, the lubricant is magnesium stearate and/or sodium stearyl fumarate. The lubricant may be present as an intra-granular component and/or as an extra-granular component. The lubricant content is suitably about 0.5 wt. %, about 1 wt. %, about 1.5 wt. %, about 2 wt. %, about 2.5 wt. %, about 3 wt. %, about 3.5 wt. %, about 4 wt. %, about 4.5 wt. %, or about 5 wt. %, and ranges thereof, such as from about 0.5 wt. % to about 5 wt. %, from about 1 wt. % to about 4 wt. %, from about 1 wt. % to about 3 wt. %, or from about 1 wt. % to about 2 wt. %.

A coating, such as a film coating, may be applied to the tablets of the present disclosure. A film coat may be used to, for example, contribute to the ease with which the tablet can be swallowed. A film coat may also be employed to improve taste and appearance. If desired, the film coat may be an enteric coat. The film coat may comprise a polymeric film-forming material such as hydroxypropyl methylcellulose, hydroxypropyl cellulose, acrylate or methacrylate copolymers, and polyvinyl alcohol-polyethylene glycol graft copolymers such as Opadry and Kollicoat IR. In addition to a film-forming polymer, the film coat may further comprise a plasticizer, e.g. polyethylene glycol, a surfactant, e.g. a Tween® type, and optionally a pigment, e.g. titanium dioxide or iron oxides. The film-coating may also comprise talc as an anti-adhesive. The film coat typically accounts for less than about 5% by weight of the dosage form.

In some aspects of the disclosure, tablets may be prepared by a process comprising pre-blending, direct tablet compression, and coating. In some other aspects, tablets may be prepared by a process comprising (i) pre-blending, (ii) granulation and sizing, such as by roller compaction and milling or by dry granulation, (iii) blending/lubrication, (iv) tablet compression, and (v) coating.

Pre-blending is designed to provide substantial homogeneity of the intra-granular components prior to roller compaction. Pre-blending equipment and related process parameters that provide for essentially homogeneous blends are known to those skilled in the art. Suitable blenders are known in the art and any apparatus typically employed in the pharmaceutical industry for uniformly admixing two or more components including V-shaped blenders, double-cone blenders, bin (container) blenders, and rotary drum blenders. The combination blender volume, blender fill, rotation speed and rotation time may be suitably determined by those skilled in the art in order to achieve an essentially homogeneous admixture of components. Blender volume is suitably about 2 L, about 50 L, about 100 L, about 200 L, about 250 L, about 500 L, about 650 L or about 1000 L. Selection of blender fill allows for convection and three-dimensional material movement, and is suitably about 25%, about 30%, about 35%, about 40%, about 50%, about 60% or about 70%, and ranges thereof, such as from about 30% to about 60%, from about 45% to about 65%, from 32% to 53% or from 32% to 40%. Blend time is suitably, 5 min, 10 min, 15 min, 20 min, 30 min, 40 min, 50 min, 60 min, or more. Rotation rate is suitably, for instance, 2 rpm, 3 rpm, 4 rpm, 5 rpm, 6 rpm, 7 rpm, 8 rpm, 9 rpm or 10 rpm.

Granulation and sizing may be achieved using any suitable method known to those skilled in the art. In some particular aspects of the disclosure, granulation and sizing comprises dry granulation, milling and screening (sieving). In some other aspects of the disclosure, dry granulation is roller compaction. Granulation and sizing improves flow and compression characteristics of the admixture of active drug and excipients. Roller compaction is a process wherein pre-blend powder particles are made to adhere together resulting in larger, granular multi-particle entities. Roller compaction generally comprises three unit operations including a feeding system, a compaction unit and a milling/sieving unit. In the compaction unit, the pre-blend is compacted between counter-rotating rolls by application of a roller compaction force (expressed in kN/cm) to form a formed mass of compacted material, such as a ribbon or a sheet. The distance between the rolls is defined as the gap width. The formed ribbon of compacted material is processed in a size reduction unit by milling to form granules that are screened to produce a plurality of granules having a desired particle size distribution.

Roller compaction and milling equipment is available commercially from a number of manufacturers including Gerteis, Fitzpatrick® and Freund-Vector. Such equipment generally provides for control of roller compaction force, gap width, roller speed and feed rate. The roller surfaces may be smooth, knurled, or one roller surface may be smooth and the other roller surface may be knurled. In any of the various aspects, the pre-blend is charged to a roller compactor feed hopper. Roller compaction is performed at a specified force and gap size, and the process is preferably run under gap control. In any of the various aspects of the disclosure, the gap size is about 2 mm, about 3 mm, about 4 mm or about 5 mm, or more, and ranges thereof, such as from about 2 mm to about 5 mm, from about 2 mm to about 4 mm, from about 3 mm to about 5 mm or from about 4 mm to about 5 mm. The roller compaction force is about 1 kN/cm, about 2 kN/cm, about 3 kN/cm, about 4 kN/cm, about 5 kN/cm, about 6 kN/cm, about 7 kN/cm or about 8 kN/cm, or more, and ranges thereof, such as from about 1 kN/cm to about 8 kN/cm, from about 2 kN/cm to about 5 kN/cm or from about 2 kN/cm to about 4 kN/cm. The formed ribbons or sheet may be milled through a screen to produce granules. In some aspects of the disclosure, the screen is integral to the mill. In any of the various aspects of the disclosure, the milling screen size is 0.5 mm, 0.75 mm, 1.0 mm, 1.25 mm, 1.5 mm, 1.75 mm, 2.0 mm, 2.25 mm or 2.5 mm, and ranges thereof, such as from about 0.5 mm to about 2.5 mm, from about 0.5 mm to about 2.0 mm, from about 0.5 mm to about 1.5 mm, from about 0.5 mm to about 1.25 mm, from about 0.75 mm to about 2.5 mm, from about 0.75 mm to about 2.0 mm, from about 0.75 mm to about 1.5 mm, or from about 0.75 mm to about 1.25 mm.

In the final blending step, granules formed by roller compaction and milling are charged to a blender and any extra-granular component, such as disintegrant (e.g., croscarmellose sodium) and lubricant (e.g., magnesium stearate or sodium stearyl fumarate), and optionally organic acid (e.g., fumaric acid), is added to the blender to form an admixture. The final blending step provides for an essentially homogeneous distribution of any external disintegrant and lubricant and provides for acceptable processability during tablet compression. Suitable blenders and related process variables are described above.

Filler, lubricant and disintegrants are typically delumped by screening prior to blending. Screening methods are known to this skilled in the art. In an example of one particular pre-blend aspect of the disclosure, filler (e.g. lactose monohydrate and MCC) and disintegrant (e.g., croscarmellose sodium) are delumped by screening and are combined with compound (I) in a blender, and the blender contents are blended for a blend time (e.g., 30 minutes) at a fixed rotation rate (e.g., 6 rpm). Lubricant (e.g., magnesium stearate) is delumped by screening and is added to a blender containing admixed filler, disintegrant and compound (I). The blender contents are blended for a blend time (e.g., 2 minutes to 30 minutes) at a fixed rotation rate (e.g., 5 rpm to 10 rpm) to form the pre-blend.

In the tableting step, a tableting die mold is filled with final blend material and the mixture is compressed to form a tablet core that is ejected. Suitable tablet presses are known in the art and are available commercially from, for instance, Riva-Piccola, Carver, Fette, Bosch Packaging Technology, GEA and Natoli Engineering Company. Generally, each tablet is made by pressing the granules inside a die, made up of hardened steel. The die is typically a disc shape with a hole cut through its center. The powder is compressed in the center of the die by two hardened steel punches that fit into the top and bottom of the die thereby forming the tablet. Tablet compression may be done in two stages with the first, pre-compression, stage involving tamping down the powder and compacting the blend slightly prior to application of the main compression force for tablet formation. The tablet is ejected from the die after compression.

Main compression force affects tablet characteristics such as hardness and appearance. Main compression force further has an impact on sticking of the final blend to tablet tooling during compression, with increased force leading to reduced sticking and, hence, fewer tablets with appearance defects. Further, the compressibility of the final blend can impact the quality (such as the presence or lack of defects) of the resultant tablet core. Compression processing parameters, such as compression force and run time, can also have an impact. In some aspects of the disclosure, the compression force is about 5 kN, about 6 kN, about 7 kN, about 8 kN, about 9 kN, about 10 kN, about 11 kN, about 12 kN, about 13 kN, about 14 kN, about 15 kN, about 16 kN, about 17 kN, about 18 kN, about 19 kN, about 20 kN, or more, and ranges thereof, such as from about 5 kN to about 20 kN, from about 14 kN to about 19 kN, from about 14 kN to about 18 kN, or from about 8 kN to about 13 kN.

The tablet cores may be film-coated to ensure that tablets are essentially tasteless and odorless, and are easy to swallow. Film coating also prevents dust formation during packaging and ensures robustness during transportation. Film coating may suitably be done by methods known in the art such as by pan coating. Suitable coating equipment includes, without limitation, a Glatt GC1000S.

In some aspects of the disclosure, tablet cores are charged to a coating pan and warmed to a target temperature. The coating suspension is prepared to a target solids content. Once the tablets are within the target temperature range, drum rotation and spraying are runs at target rates designed to achieve predetermined weight gain of about 3 wt. %, about 4 wt. % or about 5 wt. %. Outlet air temperature is maintained in a range to ensure that the target product temperature is obtained throughout coating. Once spraying is complete, the coated tablets are dried and cooled down before discharging the film-coated tablets. A solid content of a coating suspension is suitably from about 10 wt. % to about 20 wt. %, or from about 15 wt. % to about 20 wt. %. The coating spray rate per kg of tablet cores is suitably about 0.5 g/min to about 2.5 g/min, or from about 1 g/min to about 2 g/min. The coating temperature is suitably from about 30° C. to about 60° C., or from about 40° C. to about 50° C. The pan rotational speed is suitably from about 2 to about 20 rpm, from about 4 to about 15 rpm, or from about 8 to about 12 rpm. The inlet air volume varies with the batch size and is suitably from about 300 to about 1500 m3/h, from about 450 to about 1200 m3/h, or from about 1000 to about 1250 m3/h.

Amorphous Solid Dispersions

In general, amorphous solid dispersions of the present disclosure comprise a polymeric component and from about 20 wt. % to about 60 wt. % of compound (I) free base. In some aspects, the content of compound (I) free base is from about 30 wt. % to about 50 wt. %, from about 40 wt. % to about 50 wt. %, or about 50 wt. %. In some aspects, the glass transition temperature of the amorphous solid dispersions is at least 115° C., at least 125° C., or at least 150° C., such as 100° C., about 110° C., about 120° C., about 130° C., about 140° C., about 150° C., about 160° C., or about 170° C.

The amorphous solid dispersions may be characterized by aqueous dissolution at about pH 1 that is representative of normal stomach pH, at a pH of from about 4 to about 6 that is representative of achlorhydria stomach pH, and/or at a pH of from about 6.5 to about 7 that is representative of intestinal pH. More particularly, the dissolution of the compound (I) free base contained in amorphous solid dispersions in aqueous pH 1 buffer at 37° C. after 20 minutes is from about 1 mg/mL to about 2 mg/mL or from 1 mg/mL to about 1.5 mg/mL. The dissolution of the free base compound contained in the amorphous solid dispersion in aqueous pH 4.5 buffer at 37° C. after 20 minutes is at least 0.1 mg/mL, at least 0.2 mg/mL, at least 0.3 mg/mL, or from about 0.1 mg/mL to about 0.35 mg/mL. The dissolution of the free base compound contained in the amorphous solid dispersion in pH 6.8 fasted-state simulated intestinal fluid media at 37° C. after 60 minutes and after 180 minutes is at least 0.05 mg/mL, at least 0.075 mg/mL, or from about 0.075 mg/mL to about 0.1 mg/mL.

In some optional aspects of the present disclosure, the amorphous solid dispersions of the present disclosure may further comprise an acid. In such aspects, the molar equivalent ratio of the acid to the free base is from about 1:1 to about 10:1, from about 2:1 to about 10:1, from about 2:1 to about 5:1, from about 2:1 to about 4:1, or about 3:1. The acid may suitably be an organic acid or an inorganic acid. Suitable organic acids include, but are not limited to, fumaric acid, succinic acid, citric acid, and tartaric acid. Suitable inorganic acids include, but are not limited to, hydrochloric acid and sulfuric acid.

Amorphous solid dispersions comprising an acid may be characterized by aqueous dissolution at about pH 1, at a pH of about 4.5, and/or at a pH of about 6.8 as described elsewhere herein. More particularly, the dissolution of the free base compound contained in the amorphous solid dispersion in aqueous pH 1 buffer at 37° C. after 20 minutes is at least 1.5 mg/mL, at least 2 mg/mL or from about 2 mg/mL to about 2.5 mg/mL. The dissolution of the free base compound contained in the amorphous solid dispersion in aqueous pH 4.5 buffer at 37° C. after 20 minutes is at least 1 mg/mL, at least 1.25 mg/mL, or from about 1 mg/mL to about 1.5 mg/mL. The dissolution of the free base compound contained in the amorphous solid dispersion in pH 6.8 fasted-state simulated intestinal fluid media at 37° C. after 60 minutes and after 180 minutes is at least 0.05 mg/mL, or from about 0.05 mg/mL to about 0.08 mg/mL.

Non-limiting examples of polymers suitable for use singularly or in combination include alkylcellulose, hydroxyalkylcelluloses, hydroxyalkylalkylcellulose, methylcellulose (MC), ethylcellulose (EC), hydroxyethylcellulose (HEC), hydroxypropyl cellulose (HPC), hydroxypropylmethylcellulose (HPMC), hydroxyethylmethylcellulose (HEMC), hydroxypropylmethylcellulose succinate, hydroxypropylmethyl cellulose acetate succinate (HPMCAS), carboxymethylethylcellulose, sodium carboxymethylcellulose, potassium carboxymethyl cellulose, cellulose acetate succinate, cellulose acetate phthalate, hydroxypropylmethylcellulose phthalate, polyacrylic acid copolymer, poly(meth)acrylic acid polymers, poly(hydroxyalkyl acrylates), poly(hydroxyalkyl methacrylates), polyvinylpyrrolidone (PVP), homopolymers of vinylpyrrolidone, copolymers of vinylpyrrolidone, povidone, vinylpyrrolidone-vinylacetate copolymer (copovidone), copolymers of vinyl acetate, copolymers of vinyl propionate, copolymers of vinyl acetate and crotonic acid, polyethylene glycol, polyvinyl alcohol, partially hydrolyzed polyvinyl acetate, gelatin, sodium alginate, soluble starch, gum acacia, dextrin, hyaluronic acid, sodium chondroitin sulfate, propylene glycol alginate, agar, tragacanth, xanthan gum, aminoalkyl methacrylate copolymers, polyvinyl-acetal-diethylaminoacetate, methacrylate copolymer, amino methacrylate copolymer, methacrylic acid copolymer L, methacrylic acid copolymer LD, methacrylic acid copolymer S, macrogol, polyethylene oxide, polypropylene oxide, copolymers of ethylene oxide (EO) and propylene oxide (PO), carrageenans, galactomannans, and Soluplus®. Soluplus® is a polyethylene glycol, polyvinyl acetate and polyvinylcaprolactam-based graft copolymer available from BASF. In some particular aspects, the polymeric component is suitably selected from selected from polyvinylpyrrolidone, copovidone, hydroxypropyl methyl cellulose, hypromellose acetate succinate, amino methacrylate copolymer, Soluplus®, and combinations thereof.

The amorphous solid dispersions of the present disclosure may be prepared by any process which results in compound (I) being essentially in the amorphous state and essentially homogeneously dispersed throughout the polymer. Examples of methods for preparing amorphous solid dispersions include melt-extrusion processes and solvent processing methods such as spray drying and precipitation from solution with an anti-solvent.

In solvent processing methods, components comprising compound (I) and one or more polymers are dissolved in a solvent or solvent system in which the components are soluble. After dissolution, the solvent is rapidly removed by evaporation or amorphous solid dispersions are precipitated by mixing with an anti-solvent. Exemplary processes include spray-drying, spray-coating (pan-coating, fluidized bed coating, etc.), and precipitation by rapid admixing the solution with $CO_2$ or an anti-solvent. Preferably, the process comprises solvent removal to provide a solid solution of compound (I) dispersed in the polymer(s).

Suitable solvents can be any organic compound in which compound (I) and the polymer(s) are mutually soluble. Preferably, the solvent is volatile and has a boiling point of no more than 150° C. A non-exclusive list of solvents includes: alcohols such as methanol, ethanol, n-propanol, i-propanol, n-butanol and i-butanol; ketones such as acetone, methyl ethyl ketone and methyl i-butyl ketone; esters such as ethyl acetate and propylacetate; and other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used. In some aspects, the solvent system comprises water in combination with an organic solvent at a volume ratio of organic solvent to water of about 80:20, about 85:15, about 90:10 or about 95:5. Non-limiting examples of such solvent systems include acetone and water and methanol and water.

In spray-drying methods, in a spray-drying apparatus, a solution comprising compound (I) and at least one polymer is atomized into small droplets and the solvent is rapidly removed by evaporation to yield a crude amorphous solid dispersion. A rapid solvent evaporation rate is typically achieved by maintaining the partial pressure of solvent in the spray-drying apparatus well below the vapor pressure of the solvent at the temperature of the drying droplets through (1) maintaining the pressure in the spray-drying apparatus at a partial vacuum (such as from about 0.01 to about 0.50 atm), (2) mixing the liquid droplets with a warm drying gas, or (3) a combination thereof. Spray drying methods are known in the art (see, e.g., Perry's Chemical Engineers' Handbook, Eighth Edition, McGraw-Hill, 2007) and spray drying equipment is commercially available such as from Glatt, Freund-Vector and Fitzpatrick. Generally, drying gas temperature and flow rate and atomized droplet size are selected to provide formed amorphous solid dispersion particulate that is sufficiently dry by the time it reaches the spray drying apparatus chamber wall such that a fine powder that does not appreciably adhere to the wall. The actual length of time to achieve this level of dryness depends, in part, on the size of the droplets. Droplet size diameter generally ranges from about 1 µm to about 500 µm, from about 1 µm to about 100 µm, from about 1 µm to about 50 µm, or from about 1 µm to about 25 µm. Typically, a large droplet surface-to-volume ratio and a large driving force for solvent evaporation provides for drying times of a few seconds or less. It is believed that a rapid drying rate provides for a homogeneous drug dispersion within the polymer matrix as compared to slower drying rate wherein some phase separation into drug-rich and polymer-rich phases could occur. In general, amorphous solid dispersion particulate formation times should be less than about 100 seconds, less than about 10 seconds, or even less than about 1 second.

In some aspects of the disclosure, the amorphous solid dispersion is prepared by melt extrusion comprising the steps of preparing a homogeneous melt comprising compound (I) and one or more polymers and solidifying the melt by cooling. In some aspects, the melt may further comprise one or more solubilizers. In general "melting" refers to a transition of a compound (I)-polymer admixture into a liquid or rubbery state in which compound (I) is homogeneously distributed within a matrix of the polymer. In melt extrusion, it is believed that the polymer(s) melts and compound (I) dissolves in the melt to form a solution. Melt component mixing can take place before, during or after the formation of the melt. For instance, the components can be mixed first and then melted or simultaneously mixed and melted. Typically, the melt is homogenized in order to improve compound (I) dispersion efficiency. In some optional aspects, the polymer may be melted and compound (I) is subsequently added, admixed and homogenized. Melt temperature is a function of the identity of the polymer(s) and compound (I) loading. Generally, the melt temperature is from about 70°

C. to about 250° C., from about 80° C. to about 180° C., or from about 100° C. to about 140° C.

Compound (I) may be in the form of a solid, a solution, or dispersion in a suitable solvent such as described elsewhere herein. When solvent is present, at least a portion of the solvent is evaporated or flashed off upon preparation of the melt. Various additives may be included in the melt, for instance, flow regulators (e.g., colloidal silica), lubricants, bulking agents (fillers), disintegrants, plasticizers, stabilizers (e.g., antioxidants), light stabilizers, radical scavengers, preservatives (e.g., biocides), and combinations thereof.

Melt extrusion processing methods and equipment are known in the art. Particularly suitable are extruders or kneaders. Suitable extruders include single screw extruders, intermeshing screw extruders, and multi-screw extruders. In some aspects, the extruder is a co-rotating or counter-rotating twin screw extruder that may optionally be equipped with kneading disks or other screw elements for mixing or dispersing the melt. Extruders are typically heated by a heating element and/or by a jacketed section through which steam or heated oil is passed in order to provide at least a portion of the energy required to melt, mix and dissolve the components. Heat generated by friction and shearing of the material in the extruder may also provide a substantial amount of energy to the mixture and aid in the formation of a homogeneous melt of the components.

Extruder extrudate morphology may suitably range from pasty to viscous. In some aspects, prior to solidification, the extrudate may be directly shaped into tablets such as by a calender comprising two counter-rotating rollers with mutually matching depressions on their surface. A broad range of tablet forms can be attained by using rollers with different forms of depressions. In some aspects, films can be formed using rollers not having depressions on their surface. In some other aspects, extrudate may molded into a desired shape by injection-molding. In yet other aspects, extrudate may be subjected to profile extrusion through a die and cut into pieces, either before solidification (hot-cut) or after solidification (cold-cut).

In some aspects, the melt extrude amorphous solid dispersion material may milled or ground to granules as described elsewhere herein. The granules may then be filled into capsules or may be tableted. Suitable filled capsule and tablet excipients and methods for preparation are described elsewhere herein.

The ASD compositions of the present disclosure provide for improved compound (I) free base dissolution as compared to compound (I) free base alone. The dissolution of compound (I) free base formulated in an ASD composition in aqueous pH 1 buffer at 37° C. after 20 minutes is from about 1 mg/mL to about 2 mg/mL or from 1 mg/mL to about 1.5 mg/mL. The dissolution of compound (I) free base formulated in an ASD composition in aqueous pH 4.5 buffer at 37° C. after 20 minutes is at least 0.1 mg/mL, at least 0.2 mg/mL, at least 0.3 mg/mL, or from about 0.1 mg/mL to about 0.35 mg/mL. The dissolution of compound (I) free base formulated in an ASD composition in aqueous pH 4.5 buffer at 37° C. after 20 minutes is at least 0.1 mg/mL, at least 0.2 mg/mL, at least 0.3 mg/mL, or from about 0.1 mg/mL to about 0.35 mg/mL.

The ASD compositions of the present disclosure further comprising an acid provide for improved compound (I) free base dissolution at pH 4 to 5 as compared to compound (I) free base alone. The dissolution of compound (I) free base formulated in an ASD composition in aqueous pH 1 buffer at 37° C. after 20 minutes is at least 1.5 mg/mL, at least 2 mg/mL or from about 2 mg/mL to about 2.5 mg/mL. The dissolution of compound (I) free base formulated in an ASD composition in aqueous pH 4.5 buffer at 37° C. after 20 minutes is at least 1 mg/mL, at least 1.25 mg/mL, or from about 1 mg/mL to about 1.5 mg/mL. The dissolution of compound (I) free base formulated in an ASD composition in pH 6.8 fasted-state simulated intestinal fluid media at 37° C. after 60 minutes and after 180 minutes is at least 0.05 mg/mL, or from about 0.05 mg/mL to about 0.08 mg/mL.

The ASD compositions of the present disclosure further provide for improved pharmacokinetics at pH 4 to 5 as compared to compound (I) free base alone. The ASD compositions provide for an in vitro Cmax at pH 4 to 5 of at least 200 µM, at least 300 µM, at least 400 µM, at least 500 µM, at least 600 µM, at least 700 µM, at least 800 µM or at least 900 µM Cmax. The ASD compositions provide for an in vitro AUC at pH 4 to 5 of at least 5,000 hr*µM, at least 10,000 hr*µM, at least 15,000 hr*µM, at least 20,000 hr*µM, at least 25,000 hr*µM, or at least 25,000 hr*µM. The ASD compositions provide for an in vitro Cmax at intestinal pH of at least 100 µM, at least 150 µM, at least 200 µM, or at least 250 µM. The ASD compositions provide for an in vitro AUC at intestinal pH of at least 10,000 hr*µM, at least 15,000 hr*µM, at least 20,000 hr*µM, at least 25,000 hr*µM or at least 30,000 hr*µM.

Compound (I) Salts

In some aspects, crystalline mesylate, chloride and sulfate salts of compound (I) are provided.

Compound (I) mesylate salt Form A is generally prepared by a process comprising: (i) forming a solution of compound (I) free base Form A in a suitable solvent, (ii) combining the solution with a stoichiometric excess of methanesulfonic acid to form compound (I) mesylate salt in solution, (iii) formation of compound (I) mesylate salt Form A by crystallization, (iv) isolation of crystallized compound (I) mesylate salt Form A, (v) optionally washing of the isolated compound (I) mesylate salt Form A, and (vi) drying. Suitable solvents include polar protic solvents such as methanol, ethanol, isopropyl alcohol and acetic acid, polar aprotic solvents such as dichloromethane ("DCM"), tetrahydrofuran ("THF"), ethyl acetate, acetonitrile ("ACN"), dimethylformamide ("DMF"), dimethyl sulfoxide and acetone, and combinations thereof. In some aspects, the solvent is a solvent system comprising one or more polar protic and/or polar aprotic solvents and water. In some aspects, the solvent is methanol, ethanol or isopropyl alcohol. In some other aspects, the solvent is ethanol. The compound (I) free base concentration in the solvent is suitably about 0.05 mmol/mL, about 0.1 mmol/mL, about 0.15 mmol/mL, about 0.2 mmol/mL, about 0.25 mmol/mL, about 0.3 mmol/mL, about 0.4 mmol/mL, about 0.5 mmol/mL, about 0.6 mmol/mL, or about 0.7 mmol/mL. The dissolution temperature is suitably about 45° C., about 50° C., about 55° C., about 60° C., about 65° C., or about 70° C. Methanesulfonic acid is added in stoichiometric excess and the mole ratio of compound (I) free base to methanesulfonic acid is suitably about 1:1.01, about 1:1.05, about 1:1.1, about 1:1.15, or about 1:2. In some aspects, after methanesulfonic acid addition, the solution is cooled to less than about 50° C., such as about 45° C., about 40° C., about 35° C., or about 30° C. and held at that temperature such as for about 5 minutes, about 10 minutes, about 15 minutes, about 30 minutes, about 45 minutes, about one hour, or more. The cooled solution is seeded with compound (I) mesylate salt Form A crystals to form a slurry and held with agitation for about 30 minutes, about one hour, about 2 hours, about 3 hours, or more. Seed crystal amount is suitably about 0.5 wt. %, about 1 wt. %, about 2 wt. %, about 3 wt. %, about 4 wt. % or about 5 wt. % based on the amount of compound (I) free base. The seeded mixture is cooled at a controlled rate to about 5° C., about 10° C., about 15° C., about 20° C., or about 25° C. wherein the cooling rate is suitably about 0.05° C./min, about 0.1° C./min, about 0.15° C./min, about 0.2° C./min, about 0.5° C./min or about 1° C./min. The cooled mixture is held with agitation at temperature for about 1 hour, about 5 hours, about 10 hours, about 15 hours, or about one day. Compound (I) mesylate salt Form A crystals may be suitably isolated and collected by solid-liquid separation techniques known in the art such as filtration and centrifugation. The collected crystals may be dried by techniques known in the art, such as vacuum drying at a temperature of less than about 50° C. In some aspects, crystallization is induced or promoted by the addition of an anti-solvent to the slurry comprising compound (I) mesylate salt in solution and compound (I) mesylate salt Form A seed crystals prior to the final cooling step. Selection of a suitable anti-solvent relates to the identity of the solvent system. In some aspects, suitable anti-solvents include non-polar solvents such as pentane, heptane, hexane and diethyl ether. The amount of anti-solvent to solvent is suitably about 0.25:1 v/v, about 0.5:1 v/v, about 0.75:1 v/v, about 1:1 v/v, about 1:1.5 v/v, about 1:2 v/v, or about 1:4. The yield of compound (I) mesylate salt free base is suitably greater than 90%.

In certain aspects, the compound (I) mesylate crystalline salt form provided herein is essentially pure. For instance, in various aspects, the crystalline mesylate salt purity is of at least about 90%, at least about 95%, at least about 97%, at least about 98%, at least about 99%, at least about 99.2%, at least about 99.5%, at least about 99.6%, at least about 99.7% or at least about 99.8% by weight of a single crystalline form, the remainder of the total weight which may be other crystalline or amorphous forms and/or other compounds. In some aspects, the equivalent ratio of compound (I) to mesylate anion is about 1:1.

Figure 3A:
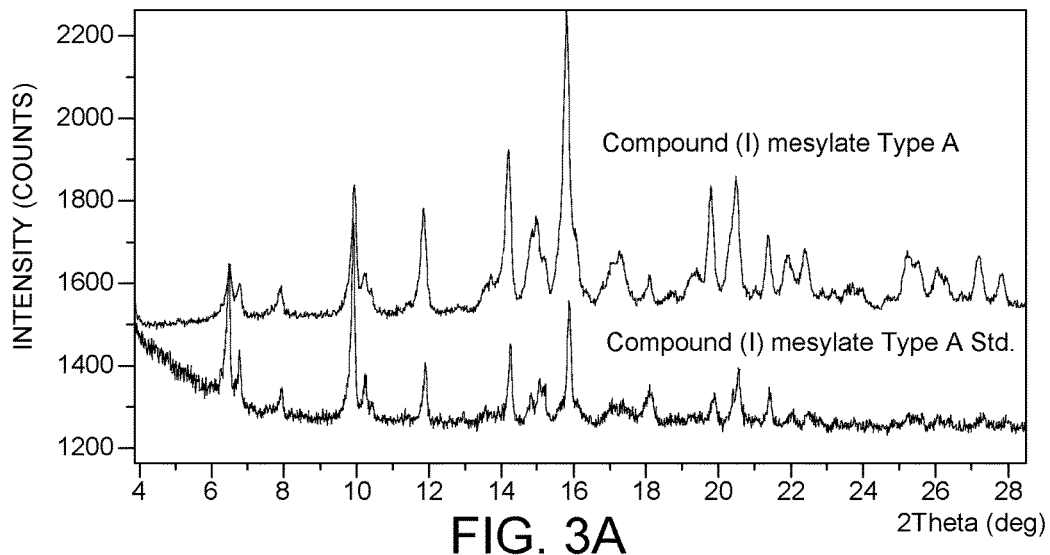
FIG. 3A provides an overlay of XRPD patterns of compound (I) mesylate salt Type A crystals prepared according to an aspect of the present disclosure as compared to standard compound (I) mesylate salt Type A crystals.
Figure 3B:
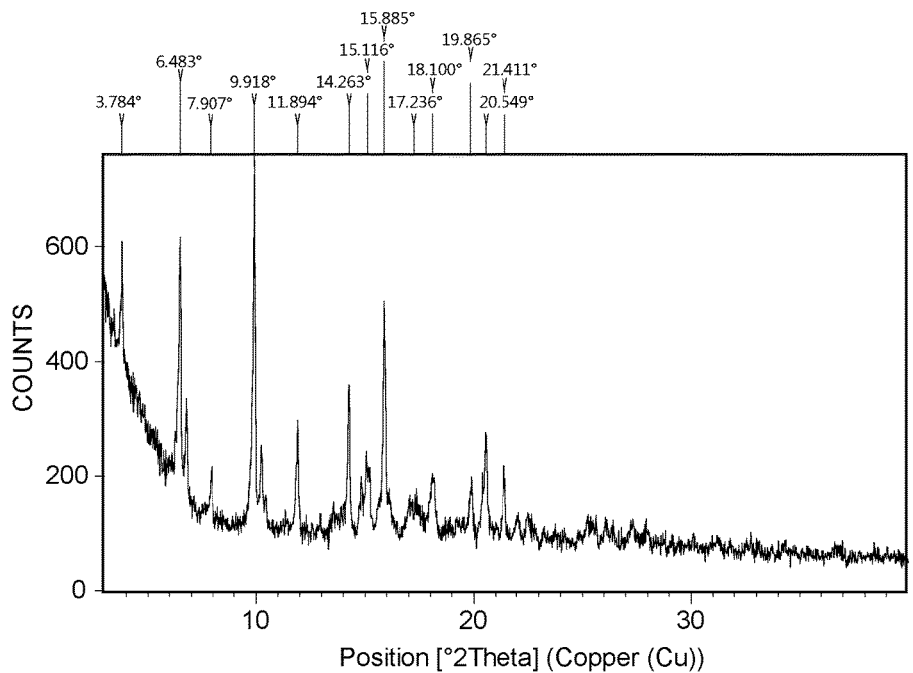
FIG. 3B provides an XRPD pattern of compound (I) mesylate salt Type A crystals prepared according to an aspect of the present disclosure.

In one aspect, the crystalline mesylate salt is essentially a single-component crystalline form or a single polymorph. In aspects, the crystalline form is essentially free of an amorphous form of compound (I). In certain aspects, a crystalline mesylate salt of compound (I) is provided having an XRPD pattern comprising one or more (e.g. one, two, three, four, five, six, seven, eight, nine, ten, or greater than ten; or at least three, at least four, at least five, at least six, or at least seven) characteristic peaks selected from peaks with 2θ angle degrees according to table 4. In certain aspects, the crystalline mesylate salt has an XRPD pattern essentially as provided in FIG. 3B. In other aspects, the crystalline mesylate salt has an XRPD pattern comprising one or more peaks (e.g., at least three, at least four, at least five, at least six, or at least seven peaks) selected from peaks with 2θ angle degrees+0.2 2θ angle degrees of about 3.78, about 6.48, about 7.91, about 9.92, about 11.89, about 14.26, about 15.12, about 15.89, about 17.24, about 18.10, about 19.86, about 20.55 and about 21.41. In other aspects, the crystalline mesylate salt has an XRPD pattern comprising one or more peaks (e.g., at least three, at least four, at least five, at least six, or at least seven peaks) selected from peaks expressed in d-values (Å) of about 23.35, about 13.63, about 11.18, about 8.92, about 7.44, about 6.21, about 5.86, about 5.58, about 5.14, about 4.90, about 4.47, about 4.32 and about 4.15.

In some aspects, the crystalline mesylate salt exhibits two endothermal peaks on DSC between room temperature and about 300° C., where a first endothermal peak occurs between about 110° C. to about 125° C., between about 115° C. to about 120° C., or from about 117° C. to about 118° C. and where a second endothermal peak occurs at between about 210° C. to about 225° C., between about 214° C. to about 219° C. from, or from about 216° C. to about 218° C. In certain aspects, the crystalline mesylate salt has a DSC pattern essentially as provided in FIG. 7.

Figure 4:
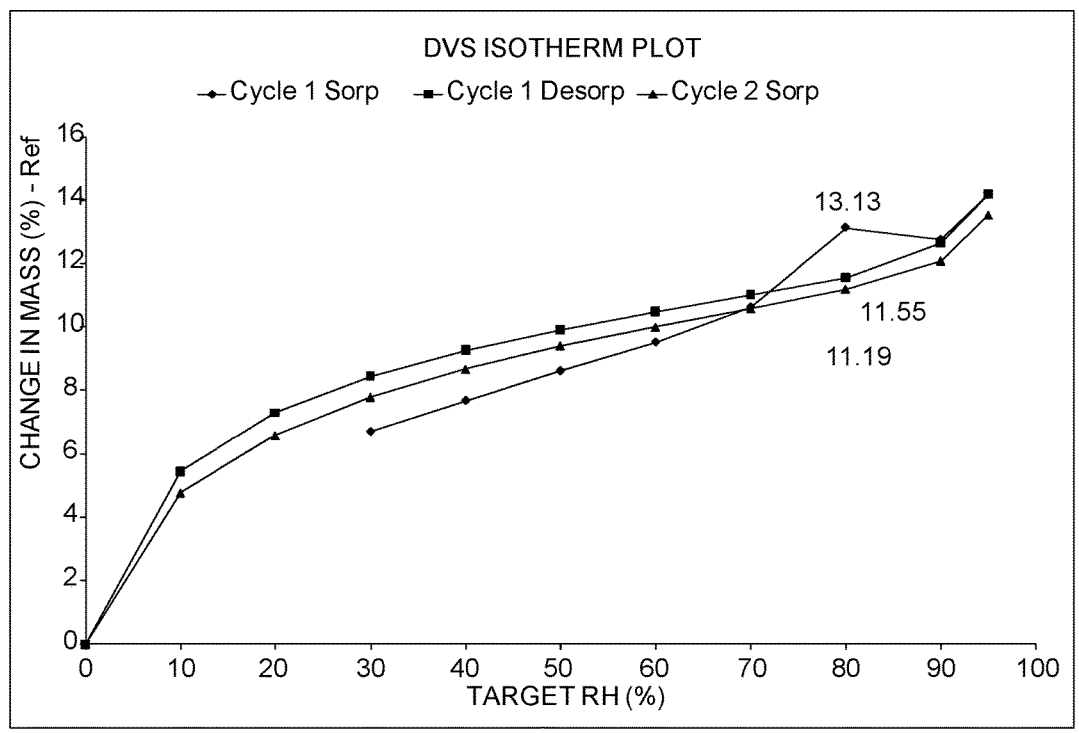
FIG. 4 provides a dynamic vapor sorption (DVS) graph of compound (I) mesylate salt type A.

In certain aspects, the crystalline mesylate salt of compound (I) has a dynamic vapor sorption ("DVS") isotherm plot corresponding essentially to the DVS isotherm plot of FIG. 4. In certain aspects, a crystalline mesylate salt of compound (I) as provided herein does not exhibit significant weight change (e.g., less than about 0.05 wt. %, less than about 0.1 wt. %, less than about 0.15 wt. %, or less than about 0.2 wt. %) from about 0% to about 95% relative humidity.

In some aspects, compound (I) chloride salts are provided. In some aspects, compound (I) chloride salt Form A is generally prepared by a process comprising: (i) forming a solution of compound (I) free base Form A in a suitable solvent, (ii) combining the solution with a stoichiometric excess of hydrochloric acid to form compound (I) chloride salt in solution, (iii) formation of compound (I) chloride salt Form A by crystallization, (iv) isolation of crystallized compound (I) chloride salt Form A, (v) optionally washing of the isolated compound (I) chloride salt Form A, and (vi) drying. Suitable solvents include polar protic solvents and polar aprotic solvents as described elsewhere herein. In some aspects, the solvent is a solvent system comprising one or more polar protic and/or polar aprotic solvents and water. In some aspects, the solvent is THF or ACN. In some particular aspects, the solvent is a solvent system comprising tetrahydrofuran and water wherein the v/v ratio of THF to water is about 5:1, about 10:1, about 15:1, about 19:1 or about 20:1, and ranges thereof. In some other particular aspects, the solvent system comprises THF, water and ACN. The compound (I) free base concentration in the solvent is suitably about 0.05 mmol/mL, about 0.1 mmol/mL, about 0.15 mmol/mL, about 0.2 mmol/mL, about 0.25 mmol/mL, about 0.3 mmol/mL, about 0.4 mmol/mL, about 0.5 mmol/mL, about 0.6 mmol/mL, or about 0.7 mmol/mL. The dissolution temperature is suitably about 20° C., about 25° C., about 30° C., about 35° C., about 40° C., about 45° C., about 50° C., about 55° C., about 60° C., about 65° C., or about 70° C. HCl is added in stoichiometric excess and the mole ratio of compound (I) free base to HCl is suitably about 1:1.01, about 1:1.05, about 1:1.1, about 1:1.15, or about 1:2. The HCl is suitably about 0.1 M, about 0.20 M, about 0.3 M or about 0.4 M. In some aspects, the HCl is prepared by diluting concentrated HCl with the solvent used to dissolve compound (I) free base (e.g., THF). In some other aspects, the HCl is prepared by diluting concentrated HCl with ethanol. In some aspects, after HCl addition, the solution is cooled to less than about 50° C., such as about 45° C., about 40° C., about 35° C., or about 30° C. and held at that temperature such as for about 5 minutes, about 10 minutes, about 15 minutes, about 30 minutes, about 45 minutes, about one hour, or more. The solution is seeded with compound (I) chloride salt Form A crystals to form a slurry. Seed crystal amount is suitably about 0.5 wt. %, about 1 wt. %, about 2 wt. %, about 3 wt. %, about 4 wt. % or about 5 wt. % based on the amount of compound (I) free base. In some aspects, the solution is seeded and crystallized at a temperature of, about 5° C., about 10° C., about 15° C., about 20° C., about 25° C. or about 25° C. The cooled mixture is held with agitation at temperature for about 10 hours, about 18 hours, about one day, about 2 days, or longer. Compound (I) chloride salt Form A crystals may be suitably isolated and collected by solid-liquid separation techniques known in the art such as filtration and centrifugation. The collected crystals may be dried by techniques known in the art, such as vacuum drying at a temperature of less than about 50° C. In some aspects, crystallization may be induced or promoted by the addition of an anti-solvent to the slurry comprising compound (I) chloride salt in solution and compound (I) chloride salt Form A seed crystals prior to the final cooling step. Selection of a suitable anti-solvent relates to the identity of the solvent system. In some aspects, suitable anti-solvents include non-polar solvents such as pentane, heptane, hexane and diethyl ether. The amount of anti-solvent to solvent is suitably about 0.25:1 v/v, about 0.5:1 v/v, about 0.75:1 v/v, about 1:1 v/v, about 1:1.5 v/v, about 1:2 v/v, or about 1:4. The yield of compound (I) chloride salt free base is suitably greater than 90%.

The compound (I) chloride Type A salts provide for improved dissolution at pH 4 to 5 as compared to compound (I) free base. At least 50 percent by weight of the mesylate salt dissolves in a pH 4.5 aqueous medium at 37° C. in 10 minutes and at least 80 percent by weight of the mesylate salt dissolves in the pH 4.5 aqueous medium at 37° C. in 30 minutes.

In certain aspects, the compound (I) chloride salt form provided herein is essentially pure. For instance, in various aspects, the crystalline chloride salt purity is of at least about 90%, at least about 95%, at least about 97%, at least about 98%, at least about 99%, at least about 99.2%, at least about 99.5%, at least about 99.6%, at least about 99.7% or at least about 99.8% by weight of a single crystalline form, the remainder of the total weight which may be other crystalline or amorphous forms and/or other compounds. In some aspects, the equivalent ratio of compound (I) to chlorine anion is about 1:1. In one aspect, the crystalline chloride salt is essentially a single-component crystalline form or a single polymorph. In aspects, the crystalline form is essentially free of an amorphous form of compound (I). In certain aspects, the crystalline compound (I) chloride salt has an XRPD pattern essentially as provided in FIG. 28 and/or FIG. 29. In some aspects, the crystalline chloride salt has an XRPD pattern comprising one or more peaks (e.g., at least three, at least four, at least five, at least six, or at least seven peaks) selected from peaks with 2θ angle degrees±0.2 2θ angle degrees of about 3.97, about 6.83, about 7.92, about 10.46, about 11.87, about 14.21, about 15.79 and about 19.76.

In some aspects, compound (I) sulfate salts are provided. In some aspects, compound (I) sulfate salt Form A is generally prepared by a process comprising: (i) forming a solution of compound (I) free base Form A in a suitable solvent, (ii) combining the solution with a stoichiometric excess of sulfuric acid to form compound (I) sulfate salt in solution, (iii) formation of compound (I) sulfate salt Form A by crystallization, (iv) isolation of crystallized compound (I) sulfate salt Form A, (v) optionally washing of the isolated compound (I) sulfate salt Form A, and (vi) drying. Suitable solvents include polar protic solvents and polar aprotic solvents as described elsewhere herein. In some aspects, the solvent for compound (I) free base dissolution is DCM and crystallization is done in a solvent system comprising DCM and ACN. The compound (I) free base concentration in the solvent is suitably about 0.05 mmol/mL, about 0.1 mmol/mL, about 0.15 mmol/mL, about 0.2 mmol/mL, about 0.25 mmol/mL, about 0.3 mmol/mL, about 0.4 mmol/mL, about 0.5 mmol/mL, about 0.6 mmol/mL, or about 0.7 mmol/mL. The dissolution temperature is suitably about 15° C., about 20° C., about 25° C., about 30° C., about 35° C., about 40° C., about 45° C., about 50° C., about 55° C., about 60° C., about 65° C., or about 70° C. In some aspects, dissolution is done at from about 15° C. to about 30° C. (room temperature). $H_2SO_4$ is added in a stoichiometric amount for the preparation of the mono-sulfate salt, and the mole ratio of compound (I) free base to $H_2SO_4$ is suitably about 1:1.01, about 1:1.05, about 1:1.1, about 1:1.15, or about 1:1.2. The $H_2SO_4$ is suitably about 0.1 M, about 0.20 M, about 0.3 M or about 0.4 M. In some aspects, the $H_2SO_4$ is prepared by diluting concentrated H2SO4 with the solvent used to dissolve compound (I) free base (e.g., DCM). In some aspects, after $H_2SO_4$ addition, the solution comprising compound (I) sulfate is heated to greater than 30° C., such as to about 35° C. or about 40° C. whereupon the solution is seeded with compound (I) sulfate salt Form A crystals to form a slurry. Seed crystal amount is suitably about 1 wt. %, about 3 wt. %, about 5 wt. %, about 10 wt. % based on the amount of compound (I) free base. In some aspects, prior to seed crystal addition, a first portion of an anti-solvent may be added to the compound (I) sulfate solution. In some such aspects, the anti-solvent is ACN and the amount of compound (I) sulfate solution to anti-solvent is about 1:1 v/v, about 1.5:1 v/v, about 2:1 v/v, about 2.5:1 v/v or about 3:1 v/v. After seed addition, anti-solvent is added to the slurry over a time period of about 1 hour, about 6 hours, about 12 hours or about 18 hours. The amount of compound (I) sulfate solution to anti-solvent is about 1:2 v/v, about 1:3 v/v, about 1:4 v/v, about 1:5 v/v, about 1:6 v/v, about 1:7 v/v, about 1:8 v/v, about 1:9 v/v, or about 1:10 v/v. After anti-solvent addition, the slurry is cooled to less than 30° C., such as about 25° C., about 20° C., about 15° C., about 10° C., or about 5° C. over a time period of about 0.5 hours, about 1 hour, about 2 hours, about 3 hours, about 4 hours, about 5 hours or about 6 hours, or more, and held at temperature for about 1 hour, about 2 hours, about 3 hours, about 4 hours, about 5 hours, about 6 hours, or more. Compound (I) sulfate salt Form A crystals may be suitably isolated and collected by solid-liquid separation techniques known in the art such as filtration and centrifugation. The collected crystals may be dried by techniques known in the art, such as vacuum drying at a temperature of less than about 60° C. The yield of compound (I) sulfate salt free base is suitably greater than 90%.

Figure 30:
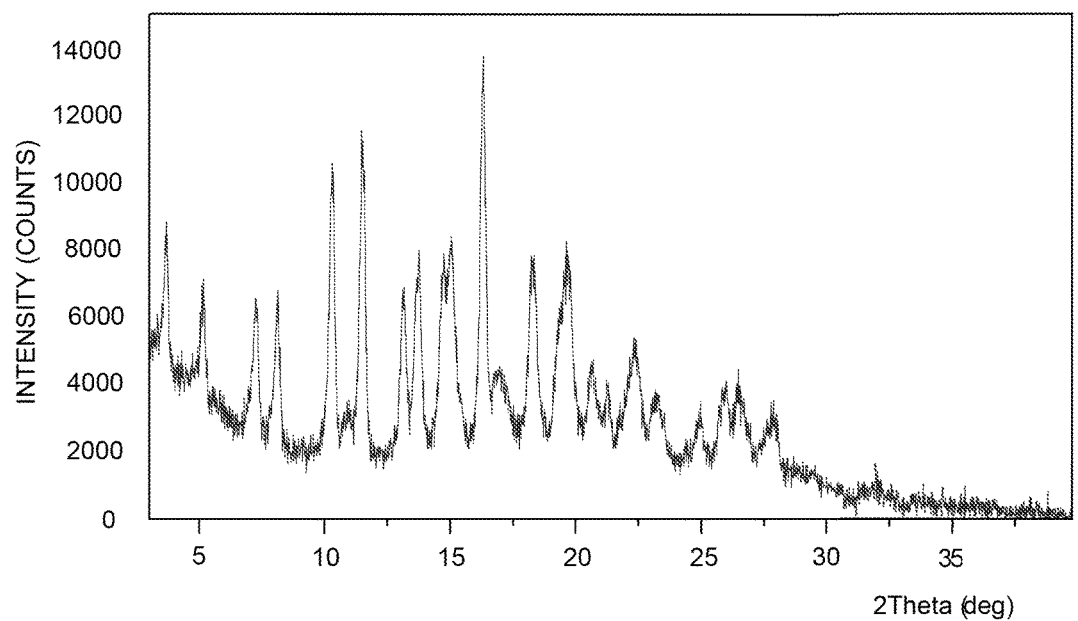
FIG. 30 provides and XRPD pattern of compound (I) sulfate salt Type A crystals prepared according to an aspect of the disclosure.

In certain aspects, the compound (I) sulfate salt form provided herein is essentially pure. For instance, in various aspects, the crystalline sulfate salt purity is of at least about 90%, at least about 95%, at least about 97%, at least about 98%, at least about 99%, at least about 99.2%, at least about 99.5%, at least about 99.6%, at least about 99.7% or at least about 99.8% by weight of a single crystalline form, the remainder of the total weight which may be other crystalline or amorphous forms and/or other compounds. In some aspects, the equivalent ratio of compound (I) to sulfate anion is about 1:1. In one aspect, the crystalline compound (I) sulfate salt is essentially a single-component crystalline form or a single polymorph. In aspects, the crystalline form is essentially free of an amorphous form of compound (I). In certain aspects, the crystalline compound (I) sulfate salt has an XRPD pattern essentially as provided in FIG. 30. In some aspects, the crystalline sulfate salt has an XRPD pattern comprising one or more peaks (e.g., at least three, at least four, at least five, at least six, or at least seven peaks) selected from peaks with 2θ angle degrees+0.2 2θ angle degrees of about 3.72, about 5.17, about 10.34, about 11.53, about 13.76, about 14.71, about 15.06, about 16.29, about 18.28 and about 19.74. In some aspects, the crystalline compound (I) sulfate salt exhibits three endothermal peaks on DSC between room temperature and about 300° C., where a first endothermal peak occurs between about 130°

C. to about 145° C., between about 136° C. to about 140° C., or from about 137° C. to about 139° C.; where a second endothermal peak occurs at between about 210° C. to about 225° C., between about 214° C. to about 219° C. from, or from about 216° C. to about 218° C.; and wherein a third endothermal peak occurs at between about 265° C. to about 280° C., between about 270° C. to about 275° C., or from about 271° C. to about 273° C.

Methods of Treatment

The dosage form compositions of the present disclosure are useful for treating a human or animal patient suffering from a disease or disorder arising from abnormal cell growth, function or behavior associated with Btk kinase such as immune disorders, cancer, cardiovascular disease, viral infection, inflammation, metabolism/endocrine function disorders. Patients suffering from such a disease or disorder may thus be treated by a method comprising the administration thereto of a therapeutic amount of a dosage form composition of the present disclosure. The condition of the patient may thereby be improved or ameliorated.

The dosage form compositions of the present disclosure may be dosed and administered in amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the indicated disorder. In general, As a general proposition, the initial pharmaceutically effective amount of compound (I) is in the range of from about 0.1 mg/kg/day to about 100 mg/kg/day, from about 0.5 mg/kg/day to about 20 mg/kg/day, or from about 1 mg/kg/day to about 10 mg/kg/day on the basis of patient body weight.

The dosage form compositions of the present disclosure are useful for treating diseases or conditions as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

In some aspects, the treatable diseases or conditions are systemic and local inflammation, arthritis, inflammation related to immune suppression, organ transplant rejection, allergies, ulcerative colitis, Crohn's disease, dermatitis, asthma, systemic lupus erythematosus, lupus nephritis, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD) and psoriasis. In some particular aspects, the disease or condition is selected from rheumatoid arthritis, systemic lupus erythematosus, and lupus nephritis.

The dosage form compositions of the present disclosure are also useful for treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

In some aspects of the disclosure, an article of manufacture, or "kit", comprising a container containing a dosage form composition of the present disclosure useful for the treatment of the diseases and disorders described above is provided. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, blister packs, etc. The container may be formed from a variety of materials such as glass or plastic. The label or package insert indicates that the dosage form composition is used for treating the condition of choice, such as rheumatoid arthritis, systemic lupus erythematosus, or lupus nephritis. The label or package insert may also indicate that the dosage form composition can be used to treat other disorders.

The kit may further comprise directions for the administration of the dosage form compositions of the present disclosure and, if present, a second pharmaceutical formulation as described elsewhere herein. For example, the kit may further comprise directions for the simultaneous, sequential or separate administration of the first and second pharmaceutical compositions to a patient in need thereof.

In another aspect, kits may provide a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

Combination Therapy and Kits

The dosage form compositions of the present disclosure may be employed alone or in combination with an additional therapeutic agent for the treatment of a disease or disorder described herein, such as inflammation or a hyperproliferative disorder (e.g., cancer). The additional therapeutic may be an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound (I) such that they do not adversely affect each other. Such compounds are suitably present in combination in amounts that are effective for the purpose intended.

The combination therapy may be administered in a simultaneous or in a sequential regimen. When administered sequentially, the combination may be dosed in two or more administrations. The combined administration includes co-administration, using separate formulations or a single pharmaceutical formulation, and consecutive administration in either order, wherein preferably there is a time period while both (or all) active agents simultaneously exert their biological activities. Suitable dosages for any of the above co-administered agents are those presently used and may be lowered due to the combined action (synergy) of the additional therapeutic agents.

The combination therapy may be synergistic such that the effect achieved when the active ingredients used together is greater than the sum of the effects that results from using the compounds separately. A synergistic effect may be attained when the active ingredients are: (1) administered or delivered simultaneously; (2) administered in alternation or in parallel; or (3) by some other regimen. When delivered in alternation therapy, a synergistic effect may be attained when the compounds are administered or delivered sequentially. In general, during alternation therapy, an effective dosage of each active ingredient is administered sequentially, i.e., serially, whereas in combination therapy, effective dosages of two or more active ingredients are administered together.

In combination therapy, a kit may comprise (a) a first container with a dosage form composition of the present disclosure and, optionally, (b) a second container with a second pharmaceutical formulation contained therein for co-administration with the dosage form compositions of the present disclosure. In such aspects, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

Unless otherwise noted, in vitro analysis of stomach and small intestine dissolution was done in a two stage apparatus. In the first stage, a first stirred vessel was used to simulate dissolution in the stomach. Stomach dissolution is suitably be measured at 37° C. at normal pH (about pH 1), achlorohydric stomach pH (in the range of from about 4 to about 6), or at an intermediate pH by selection of 500 mL of a medium having a desired pH, such as 1 or 4.5, and with typical sampling times of 5, 15 and 25 minutes. After a 30 minute dissolution time, the contents were transferred to a second stage stirred vessel used to simulate the small intestine that contained 1000 mL of a Fasted-State Simulated Intestinal Fluid (FaSSIF) buffer at 37° C. having a pH of 6.5 with typical sampling times of 35, 45, 60, 90, 120, 180 and 240 minutes.

Unless otherwise noted, the XRPD patterns were acquired on a PANalytical Empyrean diffractometer (Almelo, The Netherlands). Samples were gently flattened onto a zero-background silicon insert sample holder. A continuous 2θ scan range of 3° to 400 was used with a Cu Kα (λ 1.54056 Å) radiation source and a generator power of 45 kV and 40 mA. A 2θ step size of 0.0167 degrees/step with a step time of 17.780 second/step was used. Experiments were performed at room temperature and at ambient humidity.

Unless otherwise noted, DSC thermograms were acquired using a TA Instruments Q2000/Q200 Differential Scanning calorimeter (New Castle, Del., USA). The sample was weighed out directly into an aluminum DSC pan. The closed pan configuration was used. Unless otherwise noted, the temperature was ramped from 25° C. to 300° C. at the rate of 10° C./min.

Unless otherwise noted, TGA thermograms were acquired using a TA Instruments Q5000/Q500 Thermogravimetric Analyzer (New Castle, Del., USA). Samples were weighed out into the pan. Unless otherwise noted, the temperature was ramped from room temperature to 300° C. at the rate of 10° C./min.

Unless otherwise noted, DVS were acquired using standard procedures on a DVS Intrinsic 1 type from Surface Measurement Systems Ltd. (Alperton, Middlesex, UK). The standard isotherm run is a cycle starting at relative humidity ("RH") 0% to RH 95% at 10% intervals, followed by drying to RH 0% in 10% RH intervals (5% interval between RH 90% and 95%).

Example 1

Compound (I) Mesylate Crystalline Polymorph Type A

Figure 2:
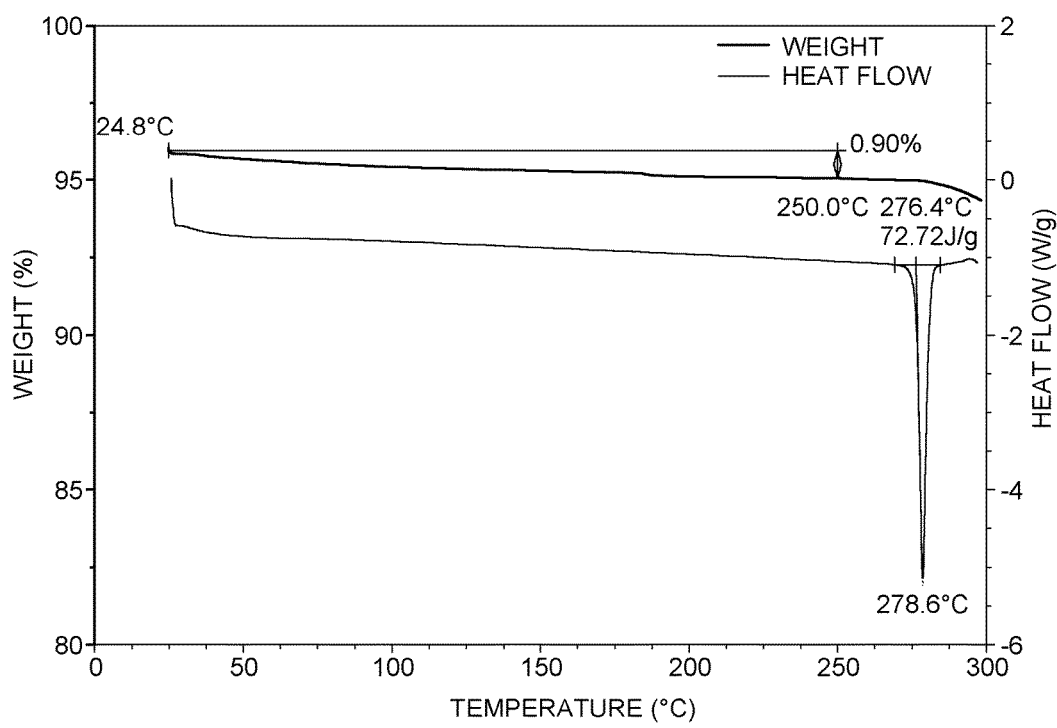
FIG. 2 provides a thermogravimetric analysis (TGA) graph and a differential scanning calorimetric (DSC) graph for compound (I) free base Type A crystals.

Compound (I) free base starting material was prepared as described in U.S. Pat. No. 8,716,274 B2. Compound (I) starting material was characterized by XRPD against a Compound (I) free base Type A standard. The XRPD results are presented in FIG. 1 and show that the starting free base material is Type A and conforms to the compound (I) free base Type A standard. TGA and DSC data are presented in FIG. 2. The TGA data shows a weight loss of up to 0.9% up to 250° C. and a sharp melting endotherm with 278.6° C. with an onset at 276.4° C.

In a first experiment for preparing compound (I) mesylate salt polymorph A, 100 mg (about 0.15 mmol) of compound (I) free base Type A was combined with 15.7 mg (about 0.16 mmol) methanesulfonic acid in a 5 mL vial. 1 mL of ethanol was added to the vial and was stirred (750 rpm, magnetically) at 50° C. to obtain a clear solution. The solution was cooled to 40° C. and held at 40° C. for 10 minutes. About 3 mg of compound (I) mesylate salt type A was added and the admixture was held at 40° C. for 60 minutes. The mixture was cooled to 20° C. at a rate of 0.1° C./minute and held at 20° C. for 10 hours. The solids were then isolated by centrifugation at 10,000 rpm and were then dried under vacuum at room temperature. The dried solids were collected to yield 106.9 mg of compound (I) mesylate polymorph type A for a yield of 93.4%. The XRPD pattern for the prepared compound (I) mesylate type A as compared to compound (I) mesylate type A standard is presented in FIG. 3. XRPD peak data for compound (I) free base Type A is recited in Table 1.

TABLE 1

Compound (I) Free Base Type A XRPD data

| Pos. [° 2Th.] | Height [cts] | FWHM Left [° 2Th.] | d-spacing [Å] | Rel. Int. [%] |
| --- | --- | --- | --- | --- |
| 3.521 | 2654.204 | 0.0640 | 25.097 | 100.00 |
| 10.402 | 437.958 | 0.0896 | 8.505 | 16.50 |
| 11.897 | 529.705 | 0.0768 | 7.439 | 19.96 |
| 12.321 | 546.315 | 0.0768 | 7.184 | 20.58 |
| 13.900 | 308.870 | 0.0895 | 6.371 | 11.64 |
| 15.158 | 510.903 | 0.1023 | 5.845 | 19.25 |
| 15.978 | 600.566 | 0.0895 | 5.547 | 22.63 |
| 16.757 | 423.526 | 0.0768 | 5.291 | 15.96 |
| 17.368 | 340.268 | 0.0895 | 5.106 | 12.82 |
| 17.878 | 60.536 | 0.2047 | 4.961 | 2.28 |
| 18.920 | 774.691 | 0.1151 | 4.691 | 29.19 |
| 19.751 | 99.957 | 0.1023 | 4.495 | 3.77 |
| 20.557 | 163.682 | 0.1023 | 4.321 | 6.17 |
| 20.814 | 171.119 | 0.1023 | 4.268 | 6.45 |
| 21.490 | 605.213 | 0.1151 | 4.135 | 22.80 |
| 21.998 | 278.325 | 0.1279 | 4.041 | 10.49 |
| 23.644 | 92.851 | 0.1023 | 3.763 | 3.50 |

In a second experiment for preparing compound (I) mesylate salt polymorph A, an acid stock solution of methanesulfonic acid in ethanol was prepared by adding 3.037 g (about 31.6 mmol) of methanesulfonic acid to 100 mL ethanol and vortexing. The acid stock solution was stored at room temperature until use. Compound (I) free base type A (20.0 g, about 30.1 mmol) was combined with 100 mL ethanol in a 500 mL three-necked jacketed crystallizer with a 2-flight overhead anchor-type agitator and was stirred at 50° C. at 350 rpm. The acid stock solution was admixed with the contents of the crystallizer within 20 minutes to yield a brown solution. The solution was cooled to 40° C. and held at 40° C. for 20 minutes. Compound (I) mesylate type A seed crystals (0.2 g) were added to the solution. The seed crystals were dissolved after 10 minutes. The solution was further cooled to 35° C. and held at 35° C. for 30 minutes. Compound (I) mesylate type A seed crystals (0.8 g) were added to the solution whereupon the solution became cloudy. The admixture was held at 35° C. for 1 hour. Within 12 hours, 100 mL of n-heptane was charged to the crystallizer and thereafter held at 35° C. for 2 hours. The mixture was then cooled to 20° C. and held at 20° C. for 3 hours. The contents of the crystallizer were collected by filtration and dried at 40° C. for 15 hours. The process yielded 24.0 g of compound (I) mesylate type A solids with a yield of 92.8%.

The product after drying contained at 5.9% residual ethanol, possibly due to the channel structure nature that depressed the effectiveness of vacuum drying. Considering the observed properties of the proposed channel structure, storing experiments at different humid atmospheres were set up to evaluate the possibility for replacing ethanol with water. As summarized in Table 2 below, after exposure at ambient conditions (RT/26% RH) and RT/57% RH (controlled by NaBr saturated aqueous solution) for 24 hrs, significant decrease of both ethanol and n-heptane was observed, indicating that wet drying, at RT/(from about 25% RH to about 55% RH), may be effective for ethanol removal. In Table 2, "TGA" refers to thermographic analysis, "KF" refers to Karl Fisher, "EtOH" refers to ethanol with results reported in ppm, and "n-Hep" refers to n-heptane with results reported in ppm, "Moist" refers to moisture.

TABLE 2

| Sample ID | Description | Scale | Residual Solvents EtOH | Residual Solvents n-Hep | Wt loss (TGA) | Moist (KF) |
| --- | --- | --- | --- | --- | --- | --- |
| 1 | Initial Mesylate (vacuum drying at 40° C. for 15 hrs) | 24 g | 58,644 | 719 | 7.6% | N/A |
| 2 | Mesylate exposed at RT/26% RH for 24 hrs) | 23 g | 1101 | 1.4 | 9.3% | 9.6% |
| 3 | Mesylate exposed at RT/57% RH for 24 hrs) | 0.1 g | 146 | 6.8 | N/A | N/A |

Figure 5:
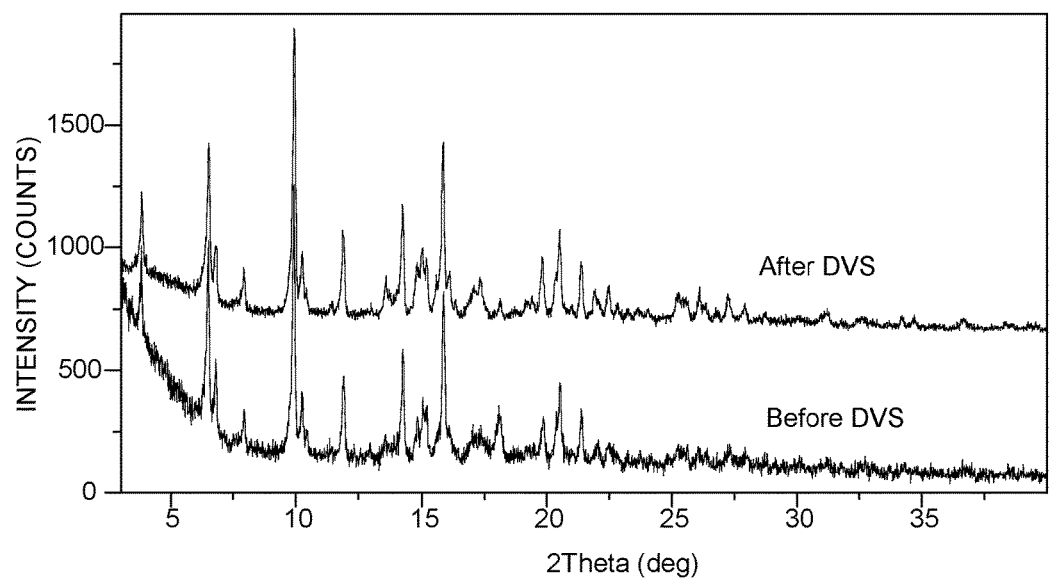
FIG. 5 provides a XPRD graph of compound (I) mesylate type A salt before and after DVS.

The compound (I) mesylate type A product was analyzed by DVS with the results reported in FIG. 4. Without being bound to any particular theory, as shown in FIG. 4, the bump observed at 25° C./80% RH may have been caused by the replacement of residual organic solvent with water. XRPD results for the product before and after DVS are presented in FIG. 5 where no significant solid form change was observed. Without being bound to any particular theory, it is believed that the XRPD results of FIG. 5 indicate a likely channel structure for the compound (I) mesylate type A product.

Figure 6:
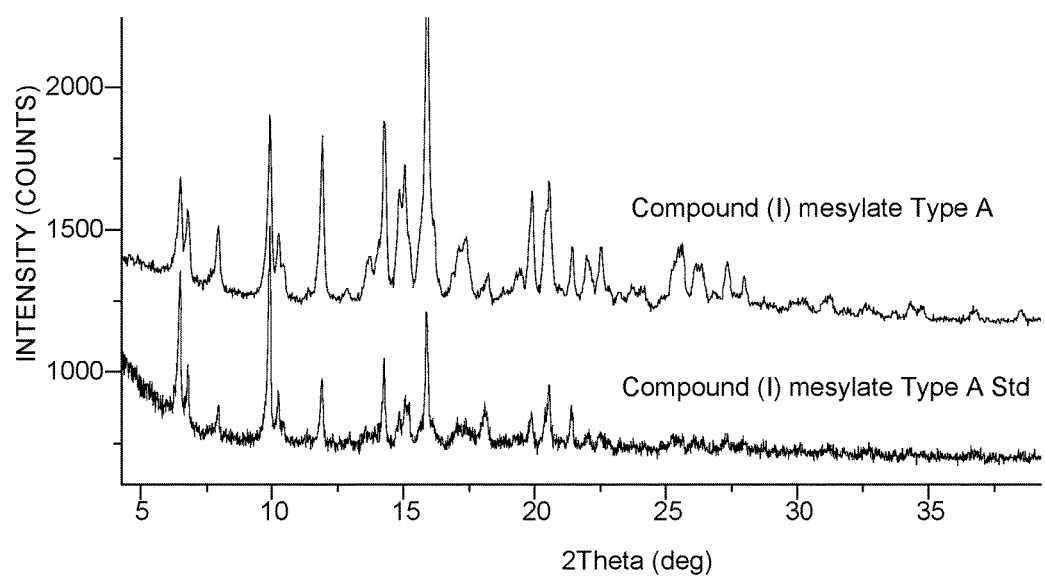
FIG. 6 provides an overlay of XRPD patterns of compound (I) mesylate salt Type A crystals prepared according to an aspect of the present disclosure as compared to standard compound (I) mesylate salt Type A crystals.
Figure 7:
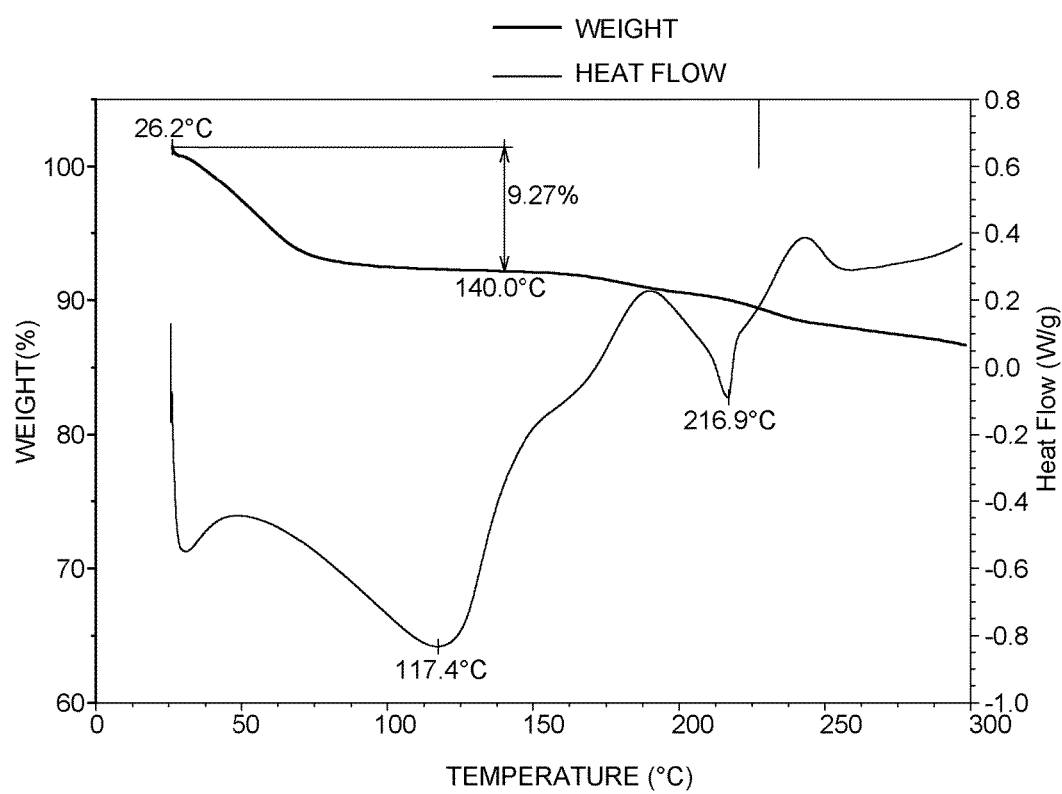
FIG. 7 provides a TGA graph and a DSC graph for compound (I) mesylate salt Type A crystals.
Figure 8:
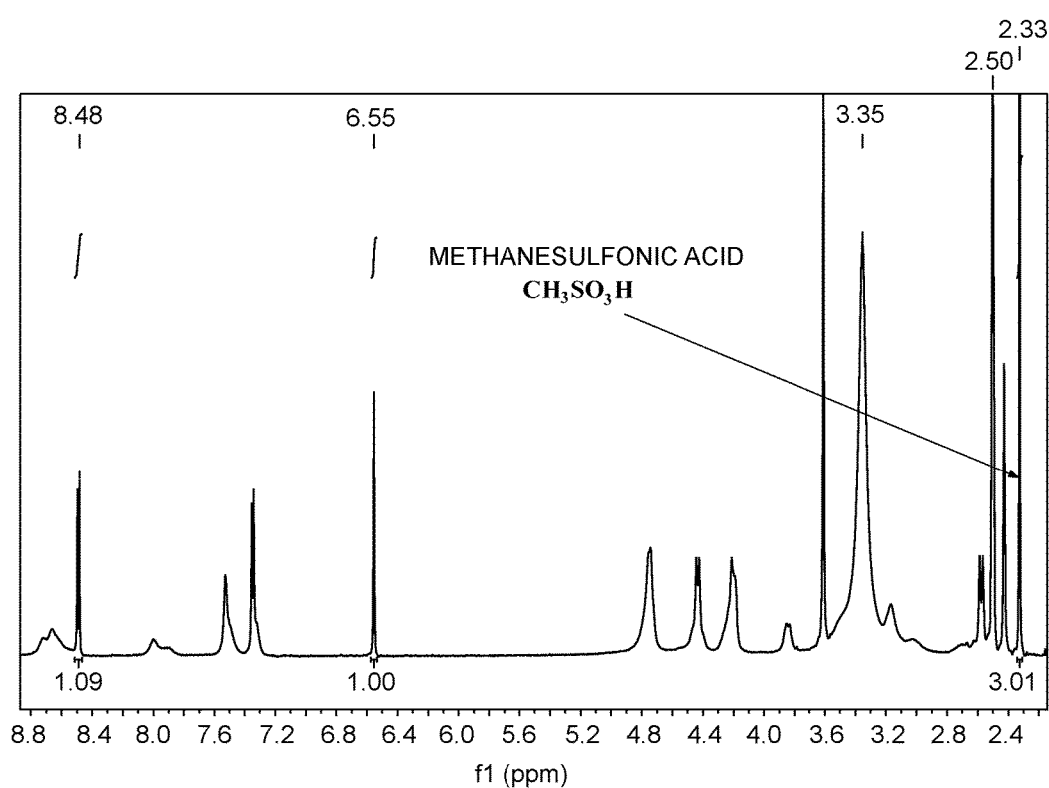
FIG. 8 provides a 1H NMR graph of compound (I) mesylate salt Type A crystals.

The compound (I) mesylate type A product was analyzed and the results are reported in Table 3 where "PLM" refers to polarized light microscopy; "XRPD" refers to X-ray powder diffractometry; "NMR" refers to nuclear magnetic resonance; "HPLC" refers to high pressure liquid chromatography; and "GC" refers to gas chromatography. In additional detail, a needle-like product was obtained that conformed to mesylate Type A, as per the XRPD pattern comparison in FIG. 6. TGA data showed a weight loss of 9.3% up to 140° C., and two endotherms at 117.4° C. and 216.9° C. (peak temperature) were observed in DSC (FIG. 7). $^1$H NMR results in FIG. 8 indicate a stoichiometry of 1.00 for the re-prepared compound (I) mesylate Type A. XRPD peak data for compound (I) mesylate salt Type A is recited in Table 4.

TABLE 3

| Test | Results |
| --- | --- |
| Appearance | Beige powder |
| Morphology by PLM | Agglomeration with fine crystals |

TABLE 3-continued

| Test | Results |
|---|---|
| Crystal form by XRPD | Compound (I) mesylate type A |
| Weight loss by TGA (%) | 9.3 (to 140° C.) |
| Endotherm by DSC (peak, ° C.) | 117.4, 216.9 |
| Stoichiometric ratio by $^1$H NMR | 1.00 |
| Water content by KF (%) | 9.6 |
| HPLC Purity (area %) | 100.0 |
| Residual solvent by GC (ppm) | EtOH: 1101.5; n-heptane: 1.4 |

TABLE 4

Compound (I) Mesylate Salt Type A XRPD data

| Pos. [° 2Th.] | Height [cts] | FWHM Left [° 2Th.] | d-spacing [Å] | Rel. Int. [%] |
|---|---|---|---|---|
| 3.784 | 450.122 | 0.1535 | 23.348 | 68.01 |
| 6.483 | 510.820 | 0.06400 | 13.634 | 77.18 |
| 7.907 | 91.077 | 0.1535 | 11.182 | 13.76 |
| 9.918 | 661.835 | 0.06400 | 8.918 | 100.00 |
| 11.894 | 193.626 | 0.1023 | 7.441 | 29.26 |
| 14.263 | 257.280 | 0.06400 | 6.210 | 38.87 |
| 15.116 | 107.182 | 0.1535 | 5.861 | 16.19 |
| 15.885 | 398.986 | 0.07675 | 5.579 | 60.28 |
| 17.236 | 39.588 | 0.5117 | 5.145 | 5.98 |
| 18.100 | 96.738 | 0.2047 | 4.901 | 14.62 |
| 19.865 | 82.458 | 0.1535 | 4.470 | 12.46 |
| 20.549 | 173.055 | 0.1023 | 4.322 | 26.15 |
| 21.411 | 94.411 | 0.1023 | 4.150 | 14.27 |

The dissolution of 100 mg compound (I) mesylate salt was evaluated in 2 mL pH 4.5 aqueous media at 37° C. over time as compared to the dissolution of 100 mg compound (I) free base in 2 mL of the buffer. The results are presented in Table 5 below wherein the pH of the media comprising dissolved compound (I) mesylate salt was 4.3 and the pH of the media comprising dissolved compound (I) free base was 4.8.

TABLE 5

| Time (min) | Compound (I) mesylate salt (% dissolved) | Compound (I) free base (% dissolved) |
|---|---|---|
| 15 | 81.4 | 0 |
| 30 | 94.5 | 0.5 |
| 45 | 98.2 | 2.3 |
| 60 | 98.2 | 4.1 |

Example 2

Dissolution of Compound (I) Free Base Versus pH

The solubility of compound (I) free base was evaluated in buffers of varying pH including Fed State Simulated Intestinal Fluid ("FeSSIF") (pH 5) and Fasted State Simulated Intestinal Fluid ("FaSSIF") (pH 6.8). The results are reported in Table 6 below.

TABLE 6

| pH | Solubility (mg/mL) |
|---|---|
| 2.54 | 35.9 |
| 2.60 | 6.48 |
| 3.02 | 1.66 |
| 3.80 | 0.036 |
| 5.04 | 0.001 |
| 6.06 | 0 |

TABLE 6-continued

| pH | Solubility (mg/mL) |
|---|---|
| 6.94 | 0.001 |
| 7.76 | 0.001 |
| FeSSIF (pH 5) | 0.018 |
| FaSSIF (pH 6.8) | 0.013 |

Example 3

Effect of Acid on Compound (I) Free Base Dissolution

Figure 9:
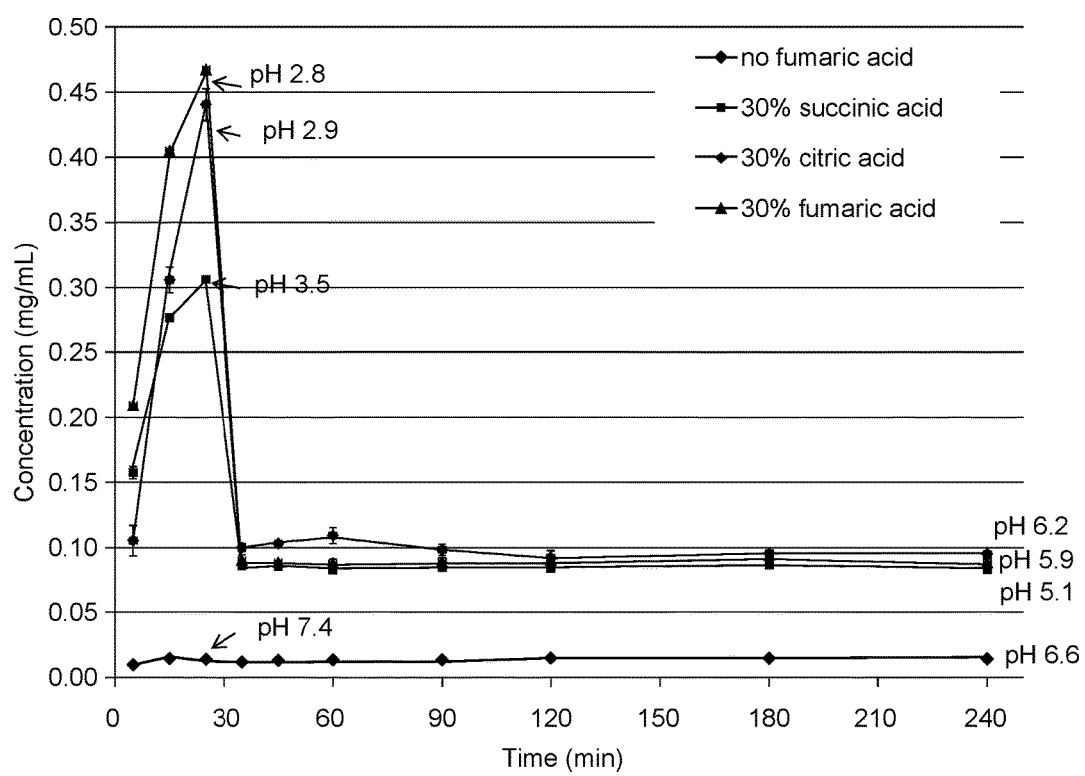
FIG. 9 provides a graph of in vitro compound (I) free base dissolution rate in a simulated achlorohydric stomach medium (pH 4.5, 0-30 min) and in a simulated intestinal medium (pH 6.5, 30-240 min) when combined with each of fumaric acid, succinic acid and citric acid.

In a first experiment, fumaric acid, succinic acid, citric acid and fumaric acid were evaluated for the capability to dissolve compound (I) free base in a 0.0000316N HCl buffer having a pH of 4.5 (representative of an achlorohydric stomach) as compared the free base in the absence of acid. In the trials, 3 tablets, each containing 100 mg compound (I) free base (20 wt. %) combined with 150 mg acid (30 wt. %) were used, and the in vitro stomach and small intestine dissolution was evaluated in the two stage apparatus described elsewhere herein. The results are presented in FIG. 9 wherein the indicated stomach pH indicates the pH at the 25 minute sampling time and the small intestine pH indicates the simulated intestinal pH at the 240 minute sampling time.

Figure 10:
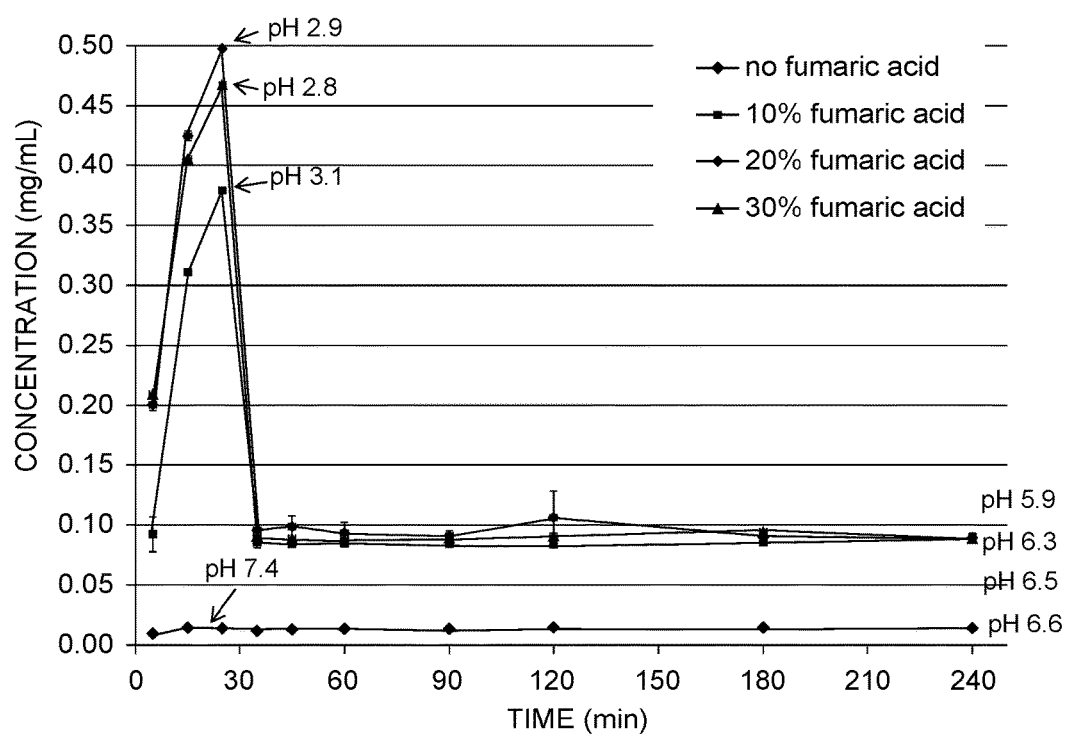
FIG. 10 provides a graph of in vitro compound (I) free base dissolution rate in a simulated achlorohydric stomach medium (pH 4.5, 0-30 min) and in a simulated intestinal medium (pH 6.5, 30-240 min) in the absence of fumaric acid and in combination with various concentrations of fumaric acid.

The effect of 10%, 20% and 30% fumaric acid content were evaluated for the capability to dissolve compound (I) free base as compared to the free base in the absence of fumaric acid in the system described immediately above. In the trials, 3 tablets, each containing 100 mg compound (I) free base (20 wt. %) combined with 50 mg acid (10 wt. %), 100 mg acid (20 wt. %), and 150 mg acid (30 wt. %) were used, and the in vitro stomach and small intestine dissolution was evaluated in the two stage apparatus described elsewhere herein. The results are presented in FIG. 10 wherein the indicated stomach pH indicates the pH at the 25 minute sampling time and the small intestine pH indicates the simulated intestinal pH at the 240 minute sampling time.

Example 4

Dissolution of Tablets Comprising Compound (I) Free Base and Fumaric Acid

Figure 11:
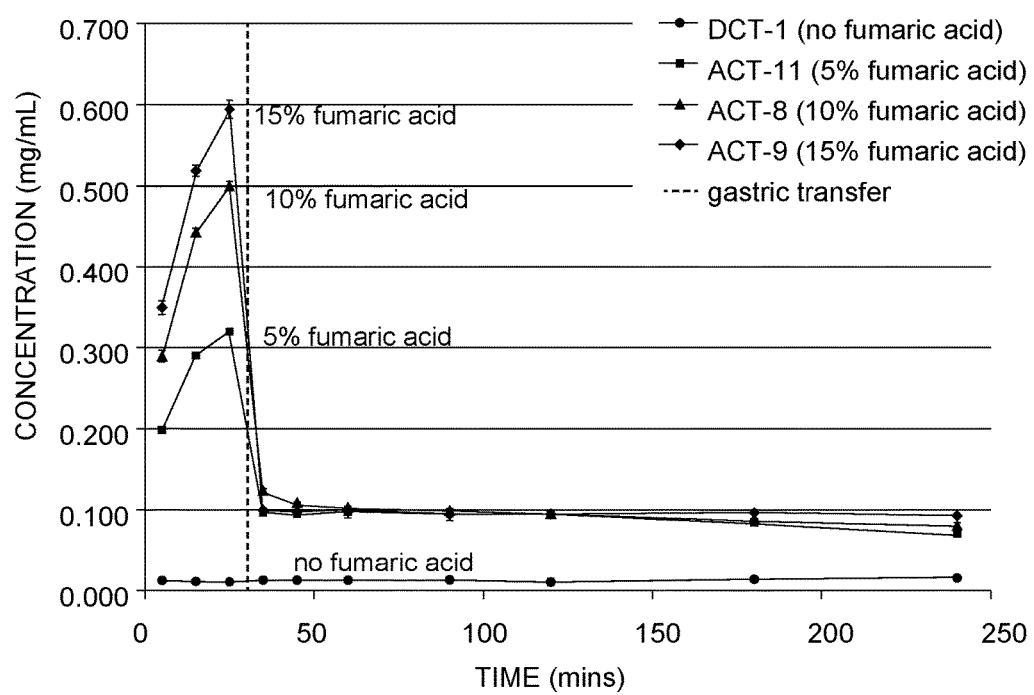
FIG. 11 provides a graph of in vitro dissolution rates of tablets comprising compound (I) free base not containing fumaric acid and in tablets comprising compound (I) free base in combination with varying amounts of fumaric acid in a simulated achlorhydric stomach medium (pH 4.5, 0-30 min) and in a simulated intestinal medium (pH 6.5, 30-240 min).

Tablets of the composition disclosed in Table 7 below were prepared wherein "API" refers to the active pharmaceutical ingredient compound (I) free base, "FA" refers to fumaric acid, "MCC" refers to microcrystalline cellulose, "Cros-Na" refers to croscarmellose sodium, "$SiO_2$" refers to colloidal silicon dioxide, "Mg stearate" refers to magnesium stearate, and where all amount are reported in wt. %. In vitro analysis of stomach and small intestine dissolution was done in the two stage apparatus described elsewhere herein wherein a 4.5 pH stomach pH was simulated. Samples were evaluated at the indicated time for compound (I) concentration in solution. The results are presented in FIG. 11.

TABLE 7

| Tablet | API | FA | MCC | Lactose | Cros-Na | $SiO_2$ | Mg Stearate |
|---|---|---|---|---|---|---|---|
| DCT-1 | 15% | 0% | 68.06% | 11.44% | 3% | 1% | 1.5% |
| ACT-8 | 15% | 10% | 59.5% | 10% | 3% | 1% | 1.5% |

TABLE 7-continued

| Tablet | API | FA | MCC | Lactose | Cros-Na | SiO$_2$ | Mg Stearate |
|---|---|---|---|---|---|---|---|
| ACT-9 | 15% | 15% | 64.75% | 0% | 3% | 1% | 1.25% |
| ACT-11 | 15% | 5% | 54.75% | 20% | 3% | 1% | 1.25% |

Example 5

Amorphous Solid Dispersions Comprising Compound (I) Free Base and at Least One Polymer Various amorphous solid dispersions comprising compound (I) free base and at least one polymer were prepared by spray drying 10 g (solids basis) spray solutions comprising 10 wt. % solids in a 90:10 acetone to water (w/w). For ASD formulations 7 to 14: the compound (I) free base content ("API") was 20 wt. %; the atomization pressure was 24 psi; and the drying gas flow rate was 43 kg/hr. For ASD formulations 32 to 35, 41 and 42: the atomization pressure varied from 24 to 32 psi; the drying gas flow rate was 43 kg/hr; the API content was 20 wt. % (ASD #s 32, 33, 35 and 41), 30 wt. % (ASD #42), or 50 wt. % (ASD #34). For ASD formulations 56 to 63: the API content was 50 wt. %; the atomization pressure was 30 psi; and the drying gas flow rate was 43 kg/hr. The ASD formulations and spray drying parameters are disclosed in Table 8 below. "ASD" refers to the amorphous solid dispersion composition reference number, "API:poly" refers to the ratio of crystalline compound (I) free base to polymer (1) or the ratio of crystalline compound (I) free base to polymer (1) and to polymer (2). "Flow" refers to solution flow rate in mL/min. "T$_{in}$" refers to the inlet temperature in ° C. "T$_{out}$" refers to the outlet temperature in ° C. "Tg" refers to the glass transition temperature in ° C. The copovidone used was Kollidon VA64 and the PVP used was Kollidon 17PF.

C./20 sec. Each of ASD formulations 7 to 14, 41, 42 and 56 to 63 exhibited a single Tg with no crystalline peaks below the T$_g$, consistent with the formation of an intimately mixed amorphous solid dispersion. ASD formulations 32 to 34 had a similar T$_g$ in the range of 63 to 73° C. consistent with Eudragit E100 at 20% drug loading; however these mixtures with PVP-based polymers, as well as the higher drug loading formulation showed a second T$_g$ value possibly indicating, without being bound to any particular theory, that the ASD polymers are phase-separated or the dispersion formed non-homogenous domains (i.e. regions either rich or poor in API or either of the two polymers, in the case of ternary dispersions). Under one theory, and without being bound to any particular theory, this could indicate that the API is segregating to Eudragit rich domains with low T$_g$.

Compound (I) free base and the ASD formulations were analyzed by x-ray diffraction with the following parameters: (1) Instrument: Bruker D2 Phaser; (2) Scan mode: Coupled 2θ-θ; (3) Scan time: 1 sec; (4) 2θ range: 1° to 40°; (5) Increment: 0.010; (6) Voltage: 30 kV; (7) Current: 10 mA; (8) Rotation: 15 r/min; (9) Holder type: Cup; (10) Divergence slit width: 1.0 mm; and (11) Knife-edge width: 1.0 mm. XRD analysis indicated that the compound (I) free base appeared to be crystalline and each ASD formulation appeared to be amorphous with no evidence of crystalline peaks.

The dissolution performance of unformulated compound (I) free base and ASD formulations was assessed via a two-stage dissolution assay which measured kinetic solubility in vitro over 210 minutes. The assay was performed in a modified USP II apparatus (paddles). The experiment measured the total drug dissolved in the presence of excess solid API (non-sink conditions), which included a combination of 'free' and colloidal or polymer-bound drug in solution. In some evaluations—to simulate the relatively high pH gastric environment in patients taking proton pump inhibitors—different simulated gastric media were used to begin the

TABLE 8

| ASD | Polymer (1) | Polymer (2) | API:Poly | Flow | T$_{in}$ | T$_{out}$ | T$_g$1 | T$_g$2 |
|---|---|---|---|---|---|---|---|---|
| 7 | Soluplus ® | — | 20:80 | 30 | 95 | 48 | 87.2 | — |
| 8 | Copovidone | — | 20:80 | 30 | 96 | 49 | 118.3 | — |
| 9 | HPMC E3 | — | 20:80 | 26 | 94 | 48 | 137.2 | — |
| 10 | HPMCAS-L | — | 20:80 | 30 | 93 | 49 | 126.8 | — |
| 11 | HPMCAS-L | PEG 400 | 20:78:2 | 28 | 95 | 50 | 111.2 | — |
| 12 | Kollidon 17PF | — | 20:80 | 26 | 115 | 48 | 146.2 | — |
| 13 | Eudragit E100 | — | 20:80 | 30 | 96 | 51 | 67.3 | — |
| 14 | Eudragit E100 | PEG 400 | 20:78:2 | 26 | 95 | 50 | 53.5 | — |
| 32 | Eudragit E100 | Copovidone | 20:40:40 | 25 | 81 | 37 | 63.1 | 121.8 |
| 33 | Eudragit E100 | PVP | 20:40:40 | 25 | 112 | 36 | 65.7 | 151.2 |
| 34 | Eudragit E100 | — | 50:50 | 25 | 86 | 36 | 72.6 | 153.4 |
| 35 | Eudragit E100 | — | 20:80 | 25 | 69 | 38 | 65.8 | N/A |
| 41* | Eudragit E100 | — | 20:80 | 20 | 77 | 36 | 87.9 | — |
| 42 | Eudragit E100 | — | 30:70 | 25 | 80 | 36 | 63.6 | — |
| 56 | HPMCAS-L | — | 50:50 | 15 | 115 | 47 | 131.9 | — |
| 57* | HPMCAS-L | — | 50:50 | 15 | 115 | 47 | 119.4 | — |
| 58* | HPMC | — | 50:50 | 15 | 115 | 48 | 150.6 | — |
| 59 | HPMC | — | 50:50 | 15 | 115 | 48 | 138.2 | — |
| 60 | Copovidone | — | 50:50 | 15 | 115 | 45 | 124.7 | — |
| 61 | PVP | — | 50:50 | 15 | 130 | 40 | 147.3 | — |
| 62* | Copovidone | — | 50:50 | 15 | 115 | 46 | 135.3 | — |
| 63* | PVP | — | 50:50 | 15 | 130 | 52 | 162.6 | — |

*ASD formulations 41, 57, 58, 62 and 63 additionally contained 3 molar equivalents of HCl in the spray solution.

T$_g$ analysis was done by modulated differential scanning calorimetry with the following parameters: (1) Instrument: TA Q-2000, RCS90 chiller; (2) Temperature range: 0-200° C.; (3) Heating rate: 5° C./min; and (4) Modulation: ±2° two-stage experiment: either pH 1 (HCl buffer) or pH 4 or 5 (acetate buffers) at a nominal compound (I) concentration of 2.0 mg/mL. In some other experiments, acetate buffer was replaced with a dilute HCl solution at similar pH, to better mimic the expected in vivo environment. After 30 minutes, the test material was transferred to fasted-state simulated intestinal fluid (FaSSIF) media consisting of physiologically relevant bile salts (SIF Powder, Biorelevant Inc.) in 100 mM phosphate buffer, and the compound (I) concentration was diluted to 1.0 mg/mL. pH of the phosphate buffer was adjusted as needed to obtain a simulated intestinal pH of 6.8±0.1 in the second stage of the dissolution experiment. The test material was sampled periodically throughout the test and samples were centrifuged at 13,000 r/min. The supernatant was diluted 1:1 with sample diluent and the compound (I) concentration was measured by HPLC. Dissolution test parameters are as follows: (1) Dissolution apparatus: Distek 2100C, miniature vessels (100 mL); (2) Stir rate: 100 r/min; (3) Temperature: 37° C.; (4) Gastric media: pH 1 HCl, pH 4 acetate, or pH 5 acetate buffer; (5) Intestinal media: FaSSIF, pH 6.8; (6) Gastric transfer time: 30 min; (7) Total time: 210 min: and (8) Sample diluent 50:40:10 H$_2$O:ACN:MeOH.

Figure 12:
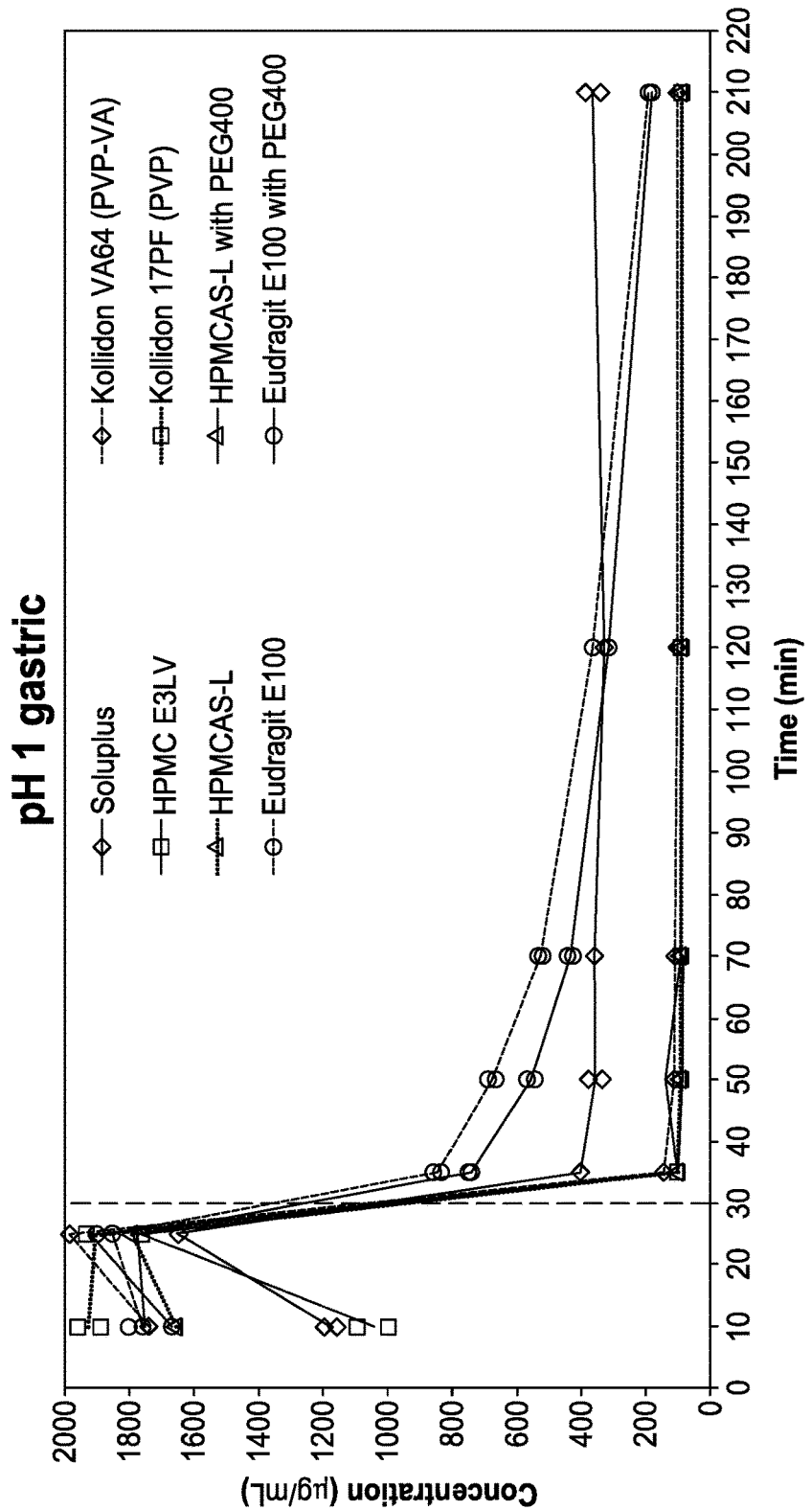
FIG. 12 provides a graph of in vitro dissolution of amorphous solid dispersions prepared from compound (I) free base and a polymer in a simulated normal stomach medium (pH of 1) and in a simulated intestinal medium.
Figure 13:
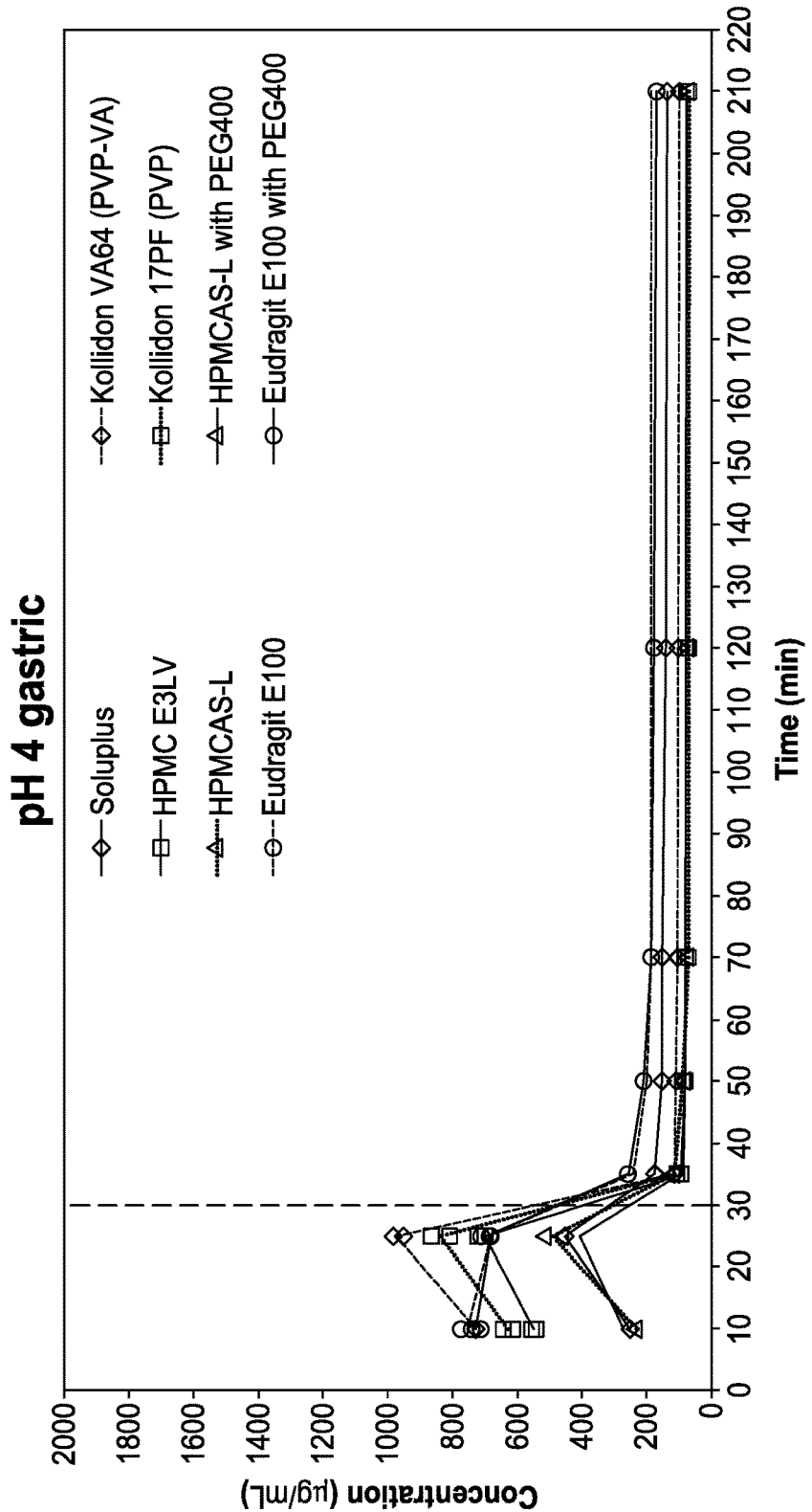
FIG. 13 provides a graph of in vitro dissolution of amorphous solid dispersions prepared from compound (I) free base and a polymer of FIG. 12 in a simulated achlorohydric stomach medium (pH of 4) and in a simulated intestinal medium.
Figure 14:
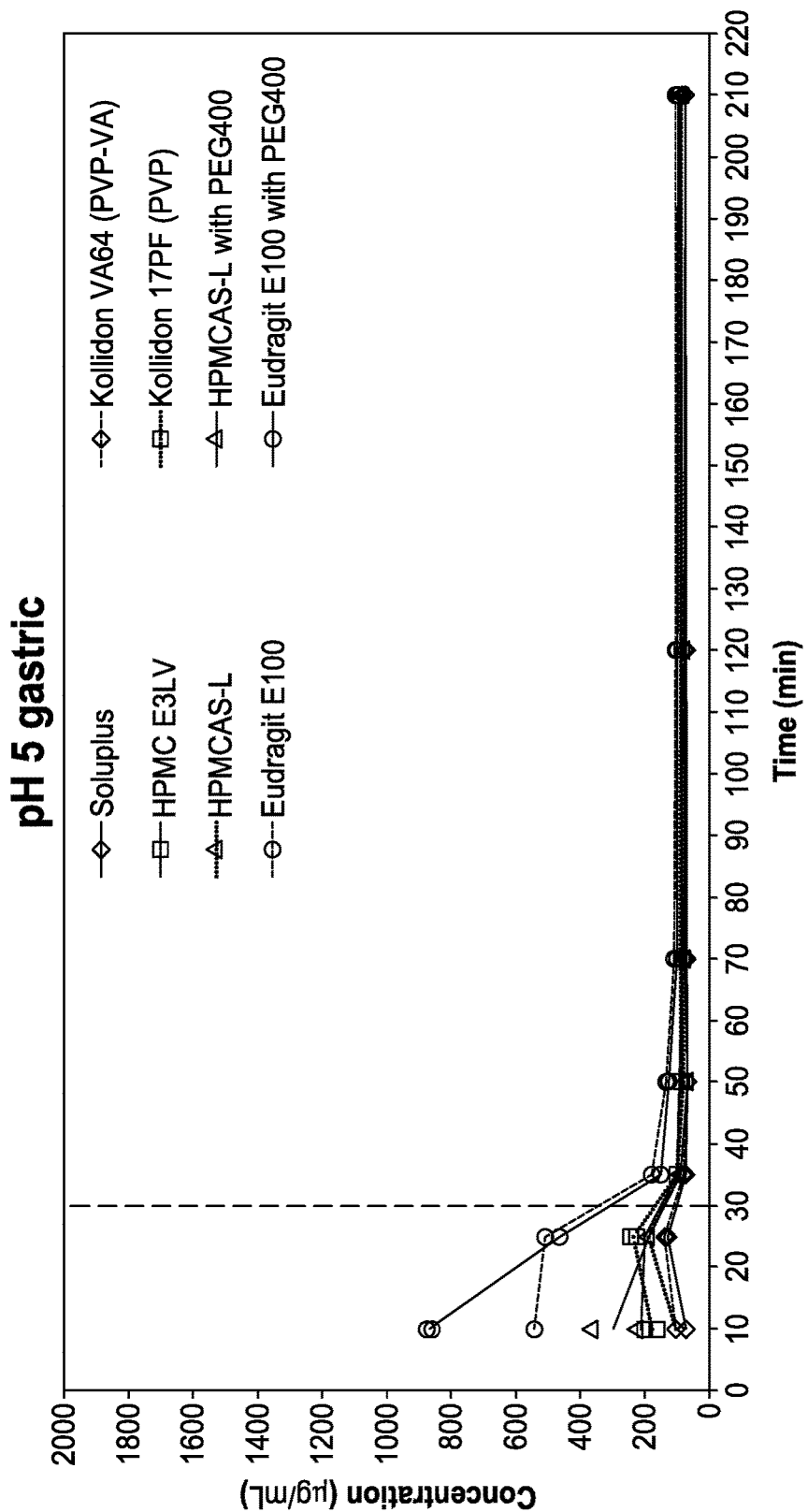
FIG. 14 provides a graph of in vitro dissolution of amorphous solid dispersions prepared from compound (I) free base and a polymer of FIG. 12 in a simulated achlorohydric stomach medium (pH of 5) and in a simulated intestinal medium.

Results of unformulated compound (I) free base dissolution at three gastric conditions indicate that the kinetic dissolution was greatest in pH 1 gastric media, where it was fully dissolved at the dosed concentration of about 2000 ug/mL. Upon transfer to intestinal media, the test that began in the more acidic condition maintained the greatest supersaturation indicating that greater gastric dissolution leads to improved intestinal dissolution, despite the intestinal pH being the same across all experiments. Non-sink dissolution results for ASD formulations 7 to 14 are given in Table 9 below where $C_{max}$ is in μM and AUC is in hr*μM. The formulations with the greatest increase in intestinal and gastric dissolution at pH 1 (i.e. normal patient populations) were those which included Eudragit E100, a cationic copolymer based on dimethylaminoethyl methacrylate, butyl methacrylate, and methyl methacrylate, that is used as a protective tablet coating and designed to dissolve at gastric pH up to 5. Eudragit E100 formulations also gave the greatest increase in AUC (when considering total drug in solution) in the simulated intestinal portion of the experiment at all pH conditions. In all cases, solid dispersion formulations gave greater intestinal AUC. FIGS. 12 to 14 show the ASD non-sink dissolution results for each pH condition plotted over time.

TABLE 9

| | API | | | Total drug | | | |
|---|---|---|---|---|---|---|---|
| | | | | Gastric | | Intestinal | |
| ASD# | (wt. %) | Polymer | pH | $C_{max}$ | AUC | $C_{max}$ | AUC |
| 13 | 20 | Eudragit E100 | 1 | 1851 | 53787 | 843 | 74111 |
| 14 | 20 | Eudragit E100:PEG4000 | 1 | 1771 | 52729 | 739 | 64061 |
| 7 | 20 | Soluplus ® | 1 | 1652 | 41116 | 403 | 63358 |
| 8 | 20 | Copovidone | 1 | 1978 | 55156 | 143 | 19319 |
| 9 | 20 | HPMC-E3LV | 1 | 1768 | 40439 | 136 | 15677 |
| 12 | 20 | PVP | 1 | 1926 | 57439 | 104 | 15628 |
| 11 | 20 | HPMCAS-L:PEG4000 | 1 | 1921 | 53132 | 95 | 15311 |
| 10 | 20 | HPMCAS-L | 1 | 1792 | 51332 | 102 | 15195 |
| API | 100 | — | 1 | 2102 | 62463 | 97 | 13908 |
| 13 | 20 | Eudragit E100 | 4 | 779 | 22312 | 247 | 35182 |
| 14 | 20 | Eudragit E100:PEG4000 | 4 | 746 | 21769 | 259 | 34673 |
| 7 | 20 | Soluplus ® | 4 | 471 | 10557 | 178 | 26853 |
| 8 | 20 | Copovidone | 4 | 1000 | 25602 | 114 | 18596 |
| 12 | 20 | PVP | 4 | 868 | 22184 | 93 | 15338 |
| 10 | 20 | HPMCAS-L | 4 | 504 | 10510 | 110 | 14850 |
| 11 | 20 | HPMCAS-L:PEG4000 | 4 | 420 | 10090 | 93 | 14848 |
| 9 | 20 | HPMC-E3LV | 4 | 722 | 19053 | 84 | 13721 |
| API | 100 | — | 4 | 145 | 3673 | 45 | 5413 |
| 13 | 20 | Eudragit E100 | 5 | 558 | 16231 | 174 | 20777 |
| 14 | 20 | Eudragit E100:PEG4000 | 5 | 888 | 21403 | 147 | 18846 |
| 8 | 20 | Copovidone | 5 | 121 | 3220 | 98 | 16386 |
| 12 | 20 | PVP | 5 | 246 | 6275 | 95 | 15541 |
| 10 | 20 | HPMCAS-L | 5 | 193 | 4289 | 99 | 14822 |
| 9 | 20 | HPMC-E3LV | 5 | 219 | 6366 | 90 | 14342 |
| 11 | 20 | HPMCAS-L:PEG4000 | 5 | 307 | 7764 | 91 | 13950 |
| 7 | 20 | Soluplus ® | 5 | 134 | 3038 | 80 | 13635 |
| API | 100 | — | 5 | 50 | 1273 | 68 | 5996 |

Non-sink dissolution results for ASD formulations 32 to 35 are given in Table 10 below. Gastric AUC was similar for all ASD formulations in all pH conditions. Of the ASDs tested, 20:80 Compound (I):Eudragit E100 (ASD #32) showed the greatest intestinal AUC at all pH conditions.

TABLE 10

| | API | | | Total drug | | | |
|---|---|---|---|---|---|---|---|
| | | | | Gastric | | Intestinal | |
| ASD# | (wt. %) | Polymer | pH | $C_{max}$ | AUC | $C_{max}$ | AUC |
| 32 | 20 | Eudragit E100:copovidone | 1 | 2061 | 60765 | 235 | 31233 |
| 33 | 20 | Eudragit E100:PVP | 1 | 1929 | 57711 | 206 | 27707 |
| 34 | 50 | Eudragit E100 | 1 | 1956 | 58152 | 159 | 19808 |
| 35 | 20 | Eudragit E100 | 1 | 1961 | 56289 | 718 | 62120 |
| 32 | 20 | Eudragit E100:copovidone | 4 | 909 | 26937 | 185 | 23499 |
| 33 | 20 | Eudragit E100:PVP | 4 | 877 | 23283 | 179 | 21724 |
| 34 | 50 | Eudragit E100 | 4 | 1037 | 30687 | 138 | 16238 |
| 35 | 20 | Eudragit E100 | 4 | 823 | 23747 | 247 | 33163 |
| 32 | 20 | Eudragit E100:copovidone | 5 | 242 | 7230 | 144 | 22181 |
| 33 | 20 | Eudragit E100:PVP | 5 | 310 | 8869 | 147 | 19365 |
| 34 | 50 | Eudragit E100 | 5 | 285 | 8235 | 126 | 15778 |
| 35 | 20 | Eudragit E100 | 5 | 468 | 12341 | 195 | 23294 |

Non-sink dissolution results for ASD formulations 35, 41 and 42 and the unformulated API are given in Table 11 below where "Ace" refers to acetate buffer.

TABLE 11

| ASD# | API (wt. %) | Polymer | pH | Total drug Gastric $C_{max}$ | AUC | Intestinal $C_{max}$ | AUC |
|---|---|---|---|---|---|---|---|
| 35 | 20 | Eudragit E100 | 1 (HCl) | 1851 | 53787 | 843 | 74111 |
| 35 | 20 | Eudragit E100 | 4 (HCl) | N/A | N/A | N/A | N/A |
| 35 | 20 | Eudragit E100 | 5 (HCl) | N/A | N/A | N/A | N/A |
| 35 | 20 | Eudragit E100 | 4 (Ace) | 779 | 22312 | 247 | 35182 |
| 35 | 20 | Eudragit E100 | 5 (Ace) | 558 | 16231 | 174 | 20777 |
| 41 | 20 | Eudragit E100 + HCl (3 eq) | 1 (HCl) | 2042 | 57413 | 875 | 83743 |
| 41 | 20 | Eudragit E100 + HCl (3 eq) | 4 (HCl) | 238 | 6544 | 124 | 20090 |
| 41 | 20 | Eudragit E100 + HCl (3 eq) | 5 (HCl) | 245 | 6735 | 122 | 19022 |
| 41 | 20 | Eudragit E100 + HCl (3 eq) | 4 (Ace) | 967 | 28344 | 273 | 34655 |
| 41 | 20 | Eudragit E100 + HCl (3 eq) | 5 (Ace) | 511 | 12238 | 205 | 32746 |
| 42 | 30 | Eudragit E100 | 1 (HCl) | 2197 | 65333 | 260 | 38188 |
| 42 | 30 | Eudragit E100 | 4 (HCl) | 65 | 1881 | 102 | 15594 |
| 42 | 30 | Eudragit E100 | 5 (HCl) | 52 | 1248 | 111 | 16322 |
| 42 | 30 | Eudragit E100 | 4 (Ace) | 977 | 27960 | 168 | 25562 |
| 42 | 30 | Eudragit E100 | 5 (Ace) | 323 | 8871 | 152 | 20040 |
| API | 100 | — | 1 (HCl) | 2102 | 62463 | 97 | 13908 |
| API | 100 | — | 4 (HCl) | 182 | 5303 | 97 | 7537 |
| API | 100 | — | 5 (HCl) | 32 | 890 | 18 | 2033 |
| API | 100 | — | 4 (Ace) | 145 | 3673 | 45 | 5413 |
| API | 100 | — | 5 (Ace) | 50 | 1273 | 68 | 5996 |

The HCl salt formulation with Eudragit E100 showed the greatest in vitro simulated intestinal AUC compared to unformulated API and to 20:80 Compound (I):Eudragit E100, particularly at the highest gastric pH tested, indicating that this approach may prove useful to enhance dissolution. The 30:70 Compound (I):Eudragit E100 resulted in lower intestinal AUC at all pH conditions than 20:80 Compound (I):Eudragit E100 previously tested.

Figure 15A:
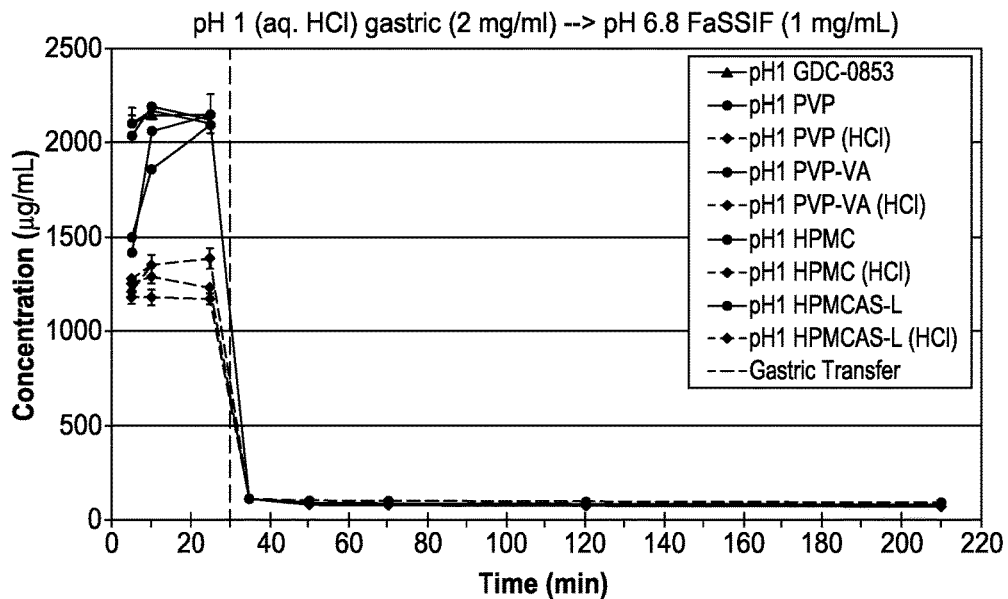
FIG. 15A provides a graph of in vitro dissolution of amorphous solid dispersions prepared from compound (I) free base and a polymer in a simulated normal stomach medium (pH of 1) and in a simulated intestinal medium.
Figure 15B:
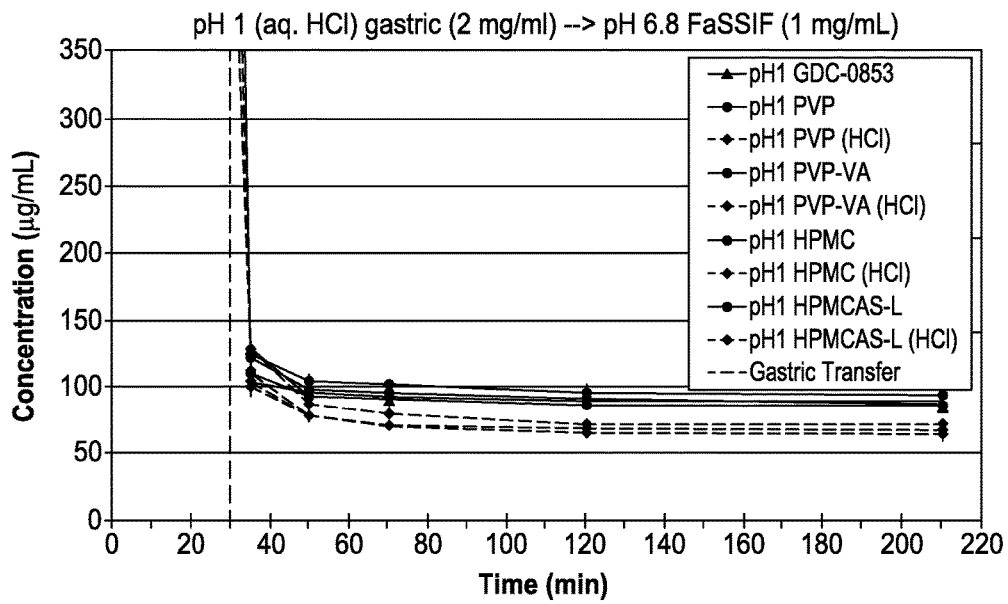
FIG. 15B zooms in on the concentration range for the simulated intestinal phase of the experiment.
Figure 16A:
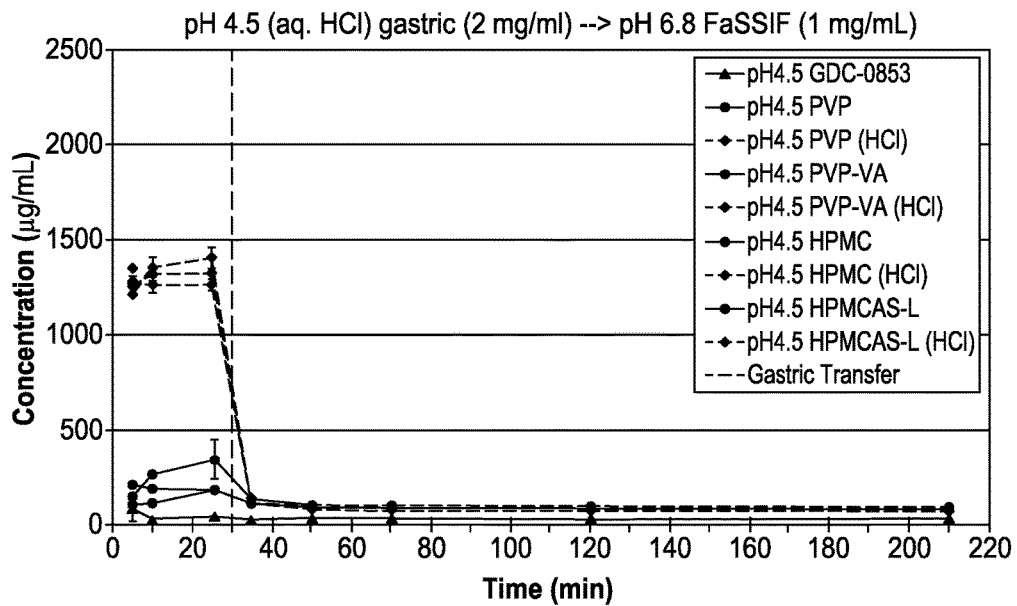
FIG. 16A provides a graph of in vitro dissolution of amorphous solid dispersions prepared from compound (I) free base and a polymer in a simulated achlorohydric stomach medium (pH of 4.5) and in a simulated intestinal medium.
Figure 16B:
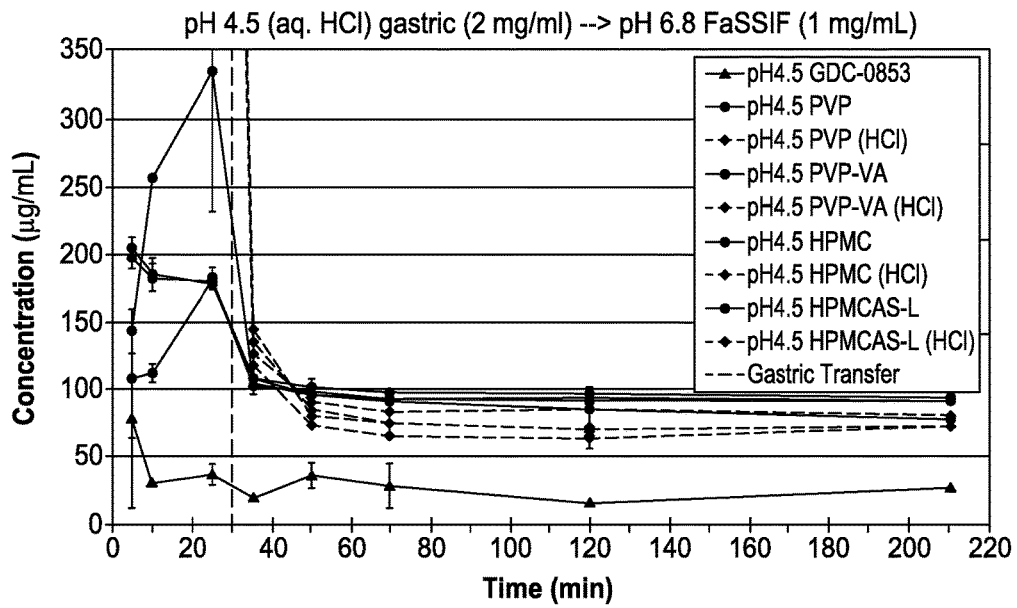
FIG. 16B zooms in on the concentration range for the simulated intestinal phase of the experiment.

Non-sink dissolution results for ASD formulations 56 to 63 are presented in FIGS. 15A, 15B, 16A and 16B. Non-sink dissolution was performed as described previously, except an intermediate gastric pH of 4.5 (HCl) was used in place of the previous separately tested pH 4 and 5 gastric conditions. FIGS. 15A (pH 1 gastric pH) and 16A (pH 4.5 gastric pH) depict the entire concentration range tested, and FIGS. 15B and 16B zoom in on the concentration range for the simulated intestinal phase of the experiment (e.g. 350 ug/mL).

All ASD formulations provided a 3- to 4-fold enhanced sustainment of dissolution following gastric transfer relative the crystalline API, and all four polymers performed equivalently within experimental variability following gastric transfer. The results indicate that at 50% drug loading, it is believed that the dissolution of the amorphous drug itself, rather than any specific interaction with the polymers, that determines dissolution performance. While initial dissolution performance in gastric pH appeared quite different depending on the polymer used, all the curves converged to a similar equilibrium dissolution of about 100 ug/mL under intestinal pH conditions. The addition of HCl salt to the ASDs significantly enhanced dissolution at elevated gastric pH of 4.5, but the enhancement was not indicated at a simulated intestinal pH of 6.

ASD formulations 60 (50:50 API:Copovidone), 59 (50:50 API:HPMC) and 56 (50:50 HPMCAS-L) were evaluated for short term stability. Two packaging configurations—Open and Closed—were used. For open packaging, 1 g of the ASD formulation was placed in a 75 cc white HDPE bottle without cap, and a cotton ball placed in neck of bottle. For closed packaging, 1 g of the ASD formulation was placed in a 4"×6" LDPE bag (4 mil), goose-necked and closed with a plastic cable tie. The bag placed in a 4"×6" foil pouch, heat sealed with one 0.5 g silica desiccant packet between LDPE bag and foil. The open and closed containers were stored at 40° C. and at 75% RH. Sampling time points were 2 weeks and 4 weeks.

The ASD formulations tested were off-white to light gray powders, the appearance of which was unchanged on storage for 4 weeks at accelerated conditions. Some increase in clumping of powders was observed, but these clumps were easily broken up to obtain a flowing powder. Potency and related substance were determined by HPLC as follows: (1) Column: Agilent Poroshell EC-C18 150×3.0 mm, 2.7 µm; (2) Mobile Phase A: 10 mM ammonium formate (aq.) pH 3.7; (3) Mobile Phase B: 80:20 acetonitrile:methanol; (4) Gradient: 0 min (10% mobile phase B), 2 min (45% mobile phase B), 10 min (50% mobile phase B), 15 min (75% mobile phase B), 18 min (95% mobile phase B), 20 min (95% mobile phase B), 20.1 min (10% mobile phase B) and 30 min (10% mobile phase B); (5) Column Temperature: 40° C.; (6) Flow Rate: 0.5 mL/min; (7) Sample Temperature: RT; (8) Injection Volume: 10 µL; (9) Detection Method: UV; (10) Detection Wavelength: 245 nm; (11) Detection Bandwidth: 4 nm; (12) Run Time: 30 min; (13) Target Concentration: 0.20 mg/mL; and (14) Diluent: 70:30 acetonitrile:water. The stability results are presented in Table 12 where "Total Rel. Sub." refers to total related substances.

TABLE 12

| ASD # | Potency (wt. %) | | | Total Rel. Sub. (% peak area) | | | Water (wt. %) |
|---|---|---|---|---|---|---|---|
| | Time 0 | 2 wks | 4 wks | Time 0 | 2 wks | 4 wks | 4 wks |
| 56 Closed | 48.1% | 48.1% | 44.8% | 0.52% | 0.45% | 0.75% | 1.00 |
| 56 Open | | 43.8% | 35.8% | | 1.14% | 1.50% | 4.01 |
| 59 Closed | 50.0% | 51.5% | 51.2% | 0.08% | 0.19% | 0.14% | 1.54 |
| 59 Open | | 47.4% | 48.4% | | 0.32% | 0.27% | 6.25 |
| 60 Closed | 48.2% | 49.4% | 50.2% | 0.08% | 0.24% | 0.14% | 1.52 |
| 60 Open | | 44.4% | 46.5% | | 0.45% | 0.81% | 8.41 |

Example 6

Pharmacokinetic Evaluation of Compound (I) Free Base in Combination with Fumaric Acid in a Canine Model The pharmacokinetics ("PK") of Example 4 Tablets DCT-1 (comprising 15 wt. % compound (I) free base and no fumaric acid), ACT-8 (comprising 15 wt. % compound (I) free base and 10 wt. % fumaric acid), ACT-9 (comprising 15 wt. % compound (I) free base and 15 wt. % fumaric acid) and ACT-11 (comprising 15 wt. % compound (I) free base and 5 wt. % fumaric acid) were evaluated in a canine pH dependent absorption model (see Zhou, R., et al., "pH-dependent dissolution in vitro and absorption in vivo of weakly basic drugs: development of a canine model", Pharm. Res. 2005 February; 22(2): 188-92), incorporated by reference herein in its entirety). In the study, 6 treatment groups consisting of 5 male beagle dogs each were orally dosed according to the protocol outlined in Table 13 below where "API" refers to compound (I) free base, and "FA" refers to fumaric acid. Pentagastrin stimulates the secretion of gastric acid and was administered at 6 rag/kg by intramuscular injection at 30 minutes (±2 minutes) before tablet dosing. Famotidine inhibits the secretion of gastric acid and was administered at 40 mg/dog by oral administration at 180 minutes (+10 minutes) before tablet dosing.

TABLE 13

| Group | Tablet | API:FA | Target API Dose (mg) | Pre-Treatment |
|---|---|---|---|---|
| 1 | DCT-1 | No FA | 200 mg (2 tabs per dog) | Pentagastrin |
| 2 | DCT-1 | No FA | 200 mg (2 tabs per dog) | Famotidine |
| 3 | ACT-11 | 3:1 | 200 mg (2 tabs per dog) | Famotidine |
| 4 | ACT-8 | 1.5 | 200 mg (2 tabs per dog) | Pentagastrin |
| 5 | ACT-8 | 1.5 | 200 mg (2 tabs per dog) | Famotidine |
| 6 | ACT-9 | 1:1 | 200 mg (2 tabs per dog) | Famotidine |

Figure 17:
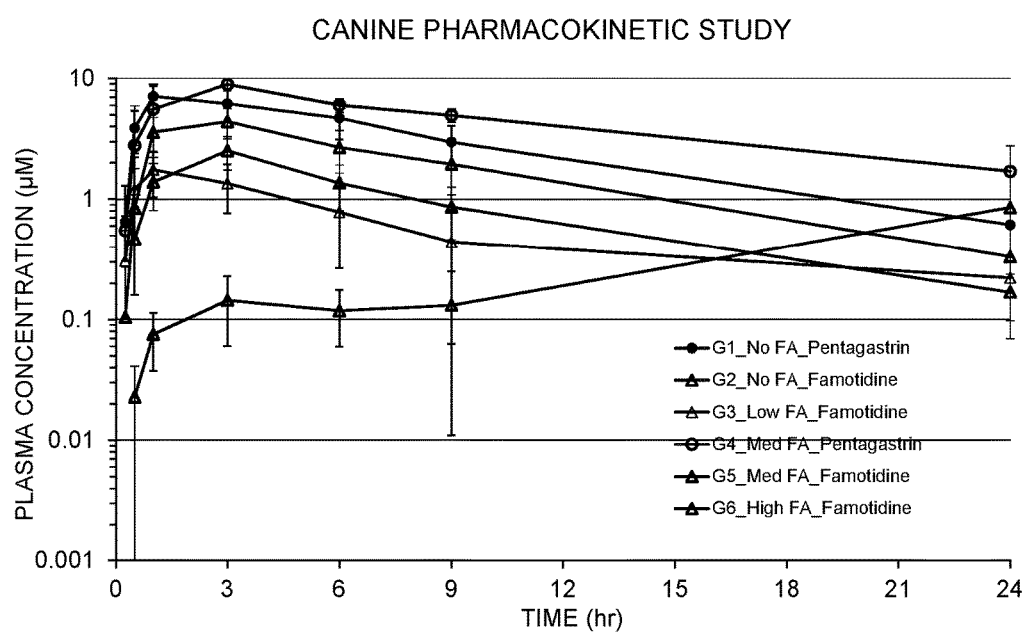
FIG. 17 provides a first graph of plasma concentration versus time for tablets comprising compound (I) free base and fumaric acid in a canine pharmacokinetics study.
Figure 18:
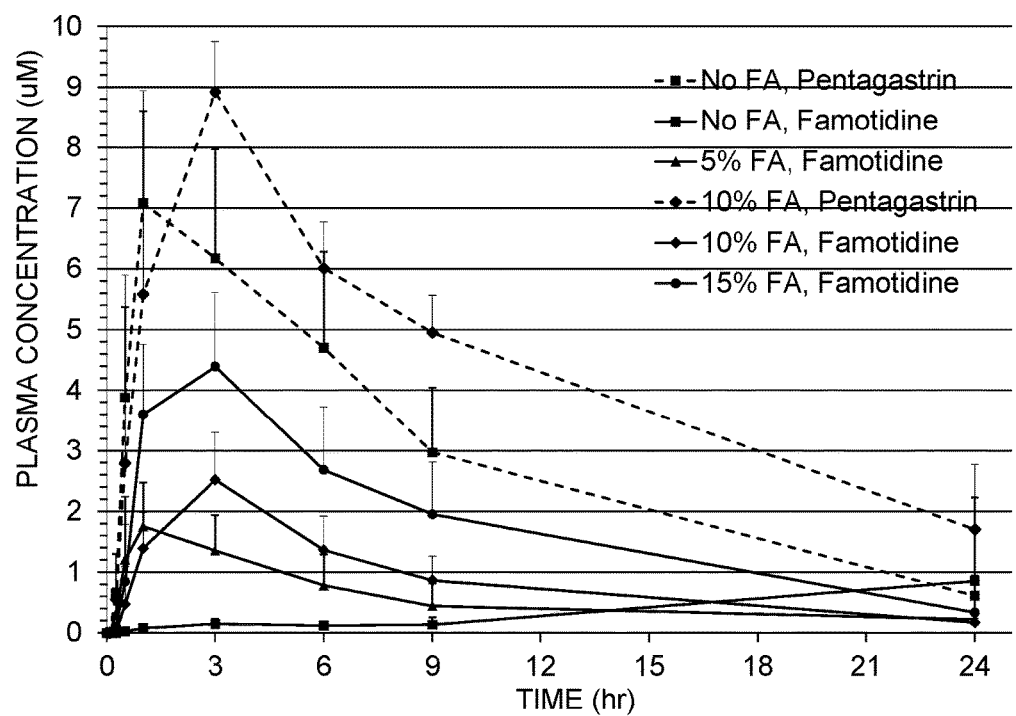
FIG. 18 provides a second graph of plasma concentration versus time for tablets comprising compound (I) free base and fumaric acid in a canine pharmacokinetics study.

The results are presented below in Table 14 and in FIGS. 17 and 18 where $C_{max}$ in µM, AUC is in hr*µM, and "FA" refers to fumaric acid. In FIG. 17, "G1" refers to Group 1, "G2" refers to Group 2, "G3" refers to Group 3, "G4" refers to Group 4, "G5" refers to Group 5, and "G6" refers to Group 6.

TABLE 14

| Group | Treatment | $C_{max}$ | $AUC_{0-24\,h}$ | % of Control Group 1 | P (compared to group 2) |
|---|---|---|---|---|---|
| 1 | Pentagastrin, no FA | 7.14 ± 1.53 | 71.2 ± 1.53 | 100% | <0.0001 |
| 2 | Famotidine, no FA | 0.95 ± 1.3 | 8.39 ± 10.2 | 12% | — |

TABLE 14-continued

| Group | Treatment | $C_{max}$ | $AUC_{0-24\,h}$ | % of Control Group 1 | P (compared to group 2) |
|---|---|---|---|---|---|
| 3 | Famotidine, 5% FA | 1.91 ± 0.8 | 14 ± 9.71 | 20% | >0.9999 |
| 4 | Famotidine, 10% FA | 2.62 ± 0.64 | 21.3 ± 6.45 | 30% | 0.7858 |
| 5 | Famotidine, 15% FA | 4.62 ± 1.18 | 43.9 ± 51.7 | 62% | 0.0026 |
| 6 | Pentagastrin, 10% FA | 9.12 ± 0.65 | 106 ± 11.5 | 149% | <0.0001 |

The results indicate that increasing fumaric acid tablet concentration results in an apparent concentration-dependent increase in absorption and exposure for dogs treated with famotidine.

Example 7

PK Evaluation of Compound (I) Free Base in Combination with Fumaric Acid as Compared to Compound (I) Mesylate Salt in a Canine Model The PK of tablets designated ACT-19 (comprising compound (I) free base and fumaric acid) and MSY-1 (comprising compound (I) mesylate salt) were evaluated in a canine model as described elsewhere herein. The tablet formulations are disclosed in Table 15 below wherein tablet MSY-1 contained 15 wt. % compound (I) on a free base basis; "FA" refers to fumaric acid; "MCC" refers to microcrystalline cellulose; "Cros-Na" refers to croscarmellose sodium; "$SiO_2$" refers to colloidal silicon dioxide; "Mg stearate" refers to magnesium stearate; "D1001" to "D1005" refers to individual dogs; and where all amount are reported in wt. %. Each dog was dosed at 200 mg compound (I) (free base basis) and where phase 1 refers to dosing with ACT-19 tablets and wherein phase 2 refers to dosing with MSY-1 tablets.

TABLE 15

| Tablet | Phase | API | FA | MCC | Lactose | Cros-Na | $SiO_2$ | Mg Stearate |
|---|---|---|---|---|---|---|---|---|
| ACT-19 | 1 | 15% | 15% | 54.5% | 10% | 3% | 1% | 1.5% |
| MSY-1 | 2 | 18.87% | 0% | 65.63% | 10% | 3% | 1% | 1.5% |

The time-concentration plasma concentration results in ltM for phase 1 (compound (I) free base+fumaric acid) and phase 2 (compound (I) mesylate salt) are presented in Tables 16 to 19 below.

TABLE 16

Phase 1 (ACT-19 tablets) and Phase 2 (MSY-1 tablets) plasma concentration results

| Phase | Subject | $C_{max}$ (uM) | $T_{max}$ (hr) | $AUC_{inf}$ (hr*uM) | $AUC_{last}$ (hr*uM) |
|---|---|---|---|---|---|
| 1 | D1001 | 3.37 | 1.00 | 22.8 | 21.3 |
|   | D1002 | 3.91 | 2.00 | 34.9 | 31.6 |
|   | D1003 | 9.28 | 2.00 | 170 | 102 |
|   | D1004 | 5.01 | 3.00 | 44.4 | 41.1 |
|   | D1005 | 4.59 | 2.00 | 51.9 | 45.1 |
|   | Mean | 5.23 | 2.00 | 64.9 | 48.3 |
|   | SD | 2.35 | 0.707 | 60.0 | 31.6 |
| 2 | D1001 | 2.90 | 2.00 | 40.9 | 33.8 |
|   | D1002 | 1.50 | 1.00 | 14.4 | 13.0 |
|   | D1003 | 2.86 | 0.500 | 25.4 | 23.0 |
|   | D1004 | 1.24 | 3.00 | 15.0 | 13.4 |
|   | D1005 | 3.56 | 24.0 | 57.5 | 35.1 |
|   | Mean | 2.41 | 6.10 | 30.7 | 23.7 |
|   | SD | 0.995 | 10.1 | 18.5 | 10.7 |

TABLE 17

Results from Table 16 without D1003 of Phase 1 and D1005 of Phase 2

| Phase | Subject | $C_{max}$ (uM) | $T_{max}$ (hr) | $AUC_{inf}$ (hr*uM) | $AUC_{last}$ (hr*uM) |
|---|---|---|---|---|---|
| 1 | D1001 | 3.37 | 1.00 | 22.8 | 21.3 |
|   | D1002 | 3.91 | 2.00 | 34.9 | 31.6 |
|   | D1003 | — | — | — | — |
|   | D1004 | 5.01 | 3.00 | 44.4 | 41.1 |
|   | D1005 | 4.59 | 2.00 | 51.9 | 45.1 |
|   | Mean | 4.22 | 2.00 | 38.5 | 34.8 |
|   | SD | 0.726 | 0.816 | 12.6 | 10.6 |
| 2 | D1001 | 2.90 | 2.00 | 40.9 | 33.8 |
|   | D1002 | 1.50 | 1.00 | 14.4 | 13.0 |
|   | D1003 | 2.86 | 0.500 | 25.4 | 23.0 |
|   | D1004 | 1.24 | 3.00 | 15.0 | 13.4 |
|   | D1005 | — | — | — | — |
|   | Mean | 2.13 | 1.63 | 23.9 | 20.8 |
|   | SD | 0.878 | 1.11 | 12.4 | 9.82 |

TABLE 18

Time-Concentration Results for Phase 1 and Phase 2 studies

| Phase | Time (hr) | D1001 | D1002 | D1003 | D1004 | D1005 | Mean (uM) | SD |
|---|---|---|---|---|---|---|---|---|
| 1 | 0 | 0 | 0 | 0 | 0.00 | 0.00 | 0 | 0 |
|   | 0.25 | 0.388 | 0.023 | 0.0227 | 0 | 0 | 0.09 | 0.169 |
|   | 0.5 | 1.96 | 1.68 | 1.47 | 0.931 | 0.534 | 1.32 | 0.576 |
|   | 1 | 3.37 | 3.47 | 6.11 | 1.62 | 2.93 | 3.5 | 1.63 |
|   | 2 | 2.57 | 3.91 | 9.28 | 4.77 | 4.59 | 5.02 | 2.53 |
|   | 3 | 2.54 | 3.32 | 6.8 | 5.01 | 4.53 | 4.44 | 1.64 |
|   | 6 | 1.28 | 1.7 | 5.25 | 2.8 | 2.27 | 2.66 | 1.56 |
|   | 9 | 0.715 | 1.39 | 4.51 | 1.9 | 1.45 | 1.99 | 1.47 |
|   | 24 | 0.168 | 0.317 | 2.6 | 0.367 | 1.29 | 0.95 | 1.02 |
| 2 | 0 | 0 | 0 | 0 | 0 | 0 | 0 | 0 |
|   | 0.25 | 0.478 | 0 | 2.42 | 0.363 | 0.668 | 0.786 | 0.946 |
|   | 0.5 | 1.88 | 0.483 | 2.86 | 0.683 | 1.04 | 1.39 | 0.98 |
|   | 1 | 2.15 | 1.5 | 2.69 | 0.802 | 1.11 | 1.65 | 0.77 |
|   | 2 | 2.9 | 1.4 | 2.29 | 1.14 | 0.979 | 1.74 | 0.822 |
|   | 3 | 2.78 | 1.1 | 2.02 | 1.24 | 0.824 | 1.59 | 0.799 |
|   | 6 | 1.7 | 0.824 | 1.33 | 0.77 | 0.597 | 1.04 | 0.457 |
|   | 9 | 1.03 | 0.588 | 0.922 | 0.71 | 0.296 | 0.71 | 0.29 |
|   | 24 | 1.17 | 0.146 | 0.251 | 0.155 | 3.56 | 1.06 | 1.47 |

TABLE 19

Time-Concentration Results for Phase 1 and Phase 2 studies without D1003 of Phase 1 and D1005 of Phase 2

| Phase | Time (hr) | D1001 | D1002 | D1003 | D1004 | D1005 | Mean (uM) | SD |
|---|---|---|---|---|---|---|---|---|
| 1 | 0 | 0 | 0 | — | 0.00 | 0 | 0.00 | 0.00 |
|   | 0.25 | 0.388 | 0.023 | — | 0 | 0 | 0.103 | 0.190 |
|   | 0.5 | 1.96 | 1.68 | — | 0.931 | 0.534 | 1.28 | 0.658 |
|   | 1 | 3.37 | 3.47 | — | 1.62 | 2.93 | 2.85 | 0.851 |
|   | 2 | 2.57 | 3.91 | — | 4.77 | 4.59 | 3.96 | 0.998 |
|   | 3 | 2.54 | 3.32 | — | 5.01 | 4.53 | 3.85 | 1.13 |
|   | 6 | 1.28 | 1.7 | — | 2.8 | 2.27 | 2.01 | 0.663 |
|   | 9 | 0.715 | 1.39 | — | 1.9 | 1.45 | 1.36 | 0.489 |
|   | 24 | 0.168 | 0.317 | — | 0.367 | 1.29 | 0.536 | 0.510 |
| 2 | 0 | 0 | 0 | 0 | 0 | — | 0.00 | 0.00 |
|   | 0.25 | 0.478 | 0 | 2.42 | 0.363 | — | 0.815 | 1.09 |
|   | 0.5 | 1.88 | 0.483 | 2.86 | 0.683 | — | 1.48 | 1.11 |
|   | 1 | 2.15 | 1.50 | 2.69 | 0.802 | — | 1.79 | 0.816 |
|   | 2 | 2.9 | 1.40 | 2.29 | 1.14 | — | 1.93 | 0.811 |
|   | 3 | 2.78 | 1.10 | 2.02 | 1.24 | — | 1.79 | 0.777 |
|   | 6 | 1.7 | 0.824 | 1.33 | 0.77 | — | 1.16 | 0.442 |
|   | 9 | 1.03 | 0.588 | 0.922 | 0.71 | — | 0.813 | 0.200 |
|   | 24 | 1.17 | 0.146 | 0.251 | 0.155 | — | 0.431 | 0.495 |

Example 8

PK Evaluation of Compound (I) Free Base in Combination with Fumaric Acid in Humans Example 8 involved a human clinical trial to investigate the PK profile of tablets comprising compound (I) free base and fumaric acid versus the PK profile of powder-in-capsule ("PIC") containing compound (I) free base in the absence of fumaric acid and excipients.

In a first study, the PK study design was a single center, randomized, open-label, two-part study. Both Part 1 and Part 2 used a 2-way crossover methodology, with one fixed sequence and three period designed to investigate the effect of formulation, food and rabeprazole on the PK of comparative compound (I) free base formulated in capsules without fumaric acid and formulated in tablets in combination with fumaric acid in healthy male and female (of non-childbearing potential) subjects (N=32). Rabeprazole is an orally administered proton pump inhibitor that inhibits the release of gastric acid. Part 1 and Part 2 methodology are summarized in Table 20 below:

TABLE 20

| Study Part | Treat. Seq. | Period 1 | Period 2 | Period 3 |
|---|---|---|---|---|
| 1 | 1 | Treatment A | Treatment B | Treatment C |
| 1 | 2 | Treatment B | Treatment A | Treatment C |
| 2 | 3 | Treatment D | Treatment E | Treatment F |
| 2 | 4 | Treatment E | Treatment D | Treatment F |

The treatment regimens are summarized as follows. Treatment A: Comparative powder-in-capsule formulation comprising 200 mg API under fasting conditions. Treatment B: Tablet formulation comprising 200 mg API under fasting conditions. Treatment C: Tablet formulation comprising 200 mg API under fasting conditions in combination with 20 mg rabeprazole twice daily. Treatment D: Tablet formulation comprising 200 mg API under fasting conditions. Treatment E: Tablet formulation comprising 200 mg API under fed conditions. Treatment F: Tablet formulation comprising 200 mg API under fed conditions in combination with 20 mg rabeprazole twice daily. The fed meal was a typical meal comprising moderate protein, carbohydrate and fat. Samples for PK analysis were collected at Day 1, 0 hour (pre-dose), and at 0.5, 1, 2, 3, 4, 6, 8, 12, 24, 36, 48 and 72 hours post dose.

Among other PK effects, the study was designed to detect a two-fold difference in PK exposures between treatments following single-dose administration. The study was further designed to measure the effect of a typical meal (E Treatment) on fasted compound (I) free base tablet (D Treatment) PK parameters (e.g. $AUC_{0-\infty}$, $C_{max}$, $T_{max}$, apparent $t_{1/2}$) by fed versus fasted comparison of pharmacokinetic parameters after a single oral dose. The study was yet further designed to measure PPI (rabeprazole) effect on fasted compound (I) free base tablet PK parameters (C Treatment) (e.g $AUC_{0-\infty}$, $C_{max}$, $T_{max}$, apparent $t_{1/2}$) vs fasted tablet (B Treatment). The study was further designed to measure PPI (rabeprazole) effect on fed compound (I) free base tablet PK parameters (F Treatment) (e.g., $AUC_{0-\infty}$, $C_{max}$, $T_{max}$, apparent $t_{1/2}$) vs fasted tablet (D Treatment).

The comparative capsules were powder-in-capsule formulations containing 50 mg compound (I) free base without fumaric acid and using a size 0 light blue opaque gelatin capsule shell.

The tablets comprised the components detailed in Table 21. The tablets were prepared as follows: The intra-granular components were blended. The intra-granular blend was slugged using a Carver press and then milled by mortar and pestle to form compound (I) free base intra-granules. The intra-granules were then blended with the extra-granular components to form a tablet blend. The tablet blend was compressed to form tablets using a Carver press.

TABLE 21

Compound (I) Free Base Tablets

| Component | Description | Amount per Tablet |
|---|---|---|
| Intra-granular Blend | | |
| Compound (I) Free base | API | 50.00 mg |
| Fumaric Acid | Powder Special, Pharma Grade | 50.00 mg |
| Lactose Monohydrate | Fast Flow 316 | 33.30 mg |
| Microcrystalline Cellulose | Avicel PH-101 | 181.65 mg |
| Magnesium Stearate | Hyqual | 1.67 mg |
| Croscarmellose Sodium | SD-711 Ac-Di-Sol | 5.00 mg |
| Silica Colloidal Anhydrous | Aerosil 200 | 1.67 mg |
| Extra-granular Blend | | |
| Magnesium Stearate | Hyqual | 3.33 mg |
| Croscarmellose Sodium | SD-711 Ac-Di-Sol | 5.00 mg |
| Silica Colloidal Anhydrous | Aerosil 200 | 1.67 mg |
| Total per tablet | | 333.29 mg |

The Study 1 PK Results are presented in Table 22 and the Study 2 PK results are presented in Table 23 wherein $T_{1/2}$ and $T_{max}$ are reported in hours, $C_{max}$ and $C_{12}$ are reported in ng/mL, AUC is reported in hr*ng/mL, "SD" refers to standard deviation, "CV" refers to the coefficient of variation, "Geo. Mean" refers to geometric mean, "CI 95% Lower" refers to the confidence interval based on the lower geometric mean, and "CI 95% Upper" refers to the confidence interval based on the upper geometric mean.

TABLE 22

Study 2 PK Results

| | $T_{1/2}$ | $T_{max}$ | $C_{max}$ | $C_{12}$ | $AUC_{0-12}$ | $AUC_{0-24}$ | $AUC_{last}$ | $AUC_{\infty}$ |
|---|---|---|---|---|---|---|---|---|
| Capsule | | | | | | | | |
| N | 16 | 16 | 16 | 16 | 16 | 16 | 16 | 16 |
| Mean | 12.65 | 1.28 | 339 | 35 | 1308 | 1554 | 1700 | 1722 |
| SD | 7.22 | 0.36 | 237 | 24 | 799 | 956 | 1011 | 1008 |
| Min | 5.56 | 0.5 | 68 | 10 | 331 | 425 | 605 | 639 |
| Median | 9.2 | 1.5 | 282 | 26 | 1100 | 1315 | 1416 | 1434 |
| Max | 29.96 | 2 | 847 | 83 | 2736 | 3321 | 3622 | 3630 |
| CV % | 57.1 | 28.4 | 70 | 70 | 61 | 62 | 60 | 59 |
| Geo. Mean | 11.08 | 1.23 | 267 | 28 | 1074 | 1281 | 1433 | 1463 |

TABLE 22-continued

Study 2 PK Results

|  | $T_{1/2}$ | $T_{max}$ | $C_{max}$ | $C_{12}$ | $AUC_{0-12}$ | $AUC_{0-24}$ | $AUC_{last}$ | $AUC_{\infty}$ |
|---|---|---|---|---|---|---|---|---|
| CI 95% Lower | 8.41 | 1.03 | 180 | 19 | 751 | 901 | 1037 | 1067 |
| CI 95% Upper | 14.59 | 1.46 | 395 | 40 | 1537 | 1820 | 1982 | 2007 |
| Tablet | | | | | | | | |
| N | 15 | 15 | 15 | 15 | 15 | 15 | 15 | 15 |
| Mean | 8.7 | 1.2 | 589 | 49 | 2139 | 2485 | 2469 | 2665 |
| SD | 3.66 | 0.65 | 283 | 24 | 868 | 1035 | 1116 | 1117 |
| Min | 5.65 | 0.5 | 325 | 25 | 1227 | 1500 | 1607 | 1612 |
| Median | 7.12 | 1 | 532 | 36 | 1734 | 1977 | 2074 | 2087 |
| Max | 19.38 | 3 | 1180 | 98 | 3804 | 4505 | 4940 | 4963 |
| CV % | 42 | 54.1 | 48 | 49 | 41 | 42 | 42 | 42 |
| Geo. Mean | 8.17 | 1.06 | 535 | 45 | 1994 | 2310 | 2462 | 2479 |
| CI 95% Lower | 6.75 | 0.8 | 418 | 35 | 1617 | 1867 | 1990 | 2007 |
| CI 95% Upper | 9.89 | 1.41 | 684 | 57 | 2459 | 2858 | 3045 | 3063 |
| Tablet + PPI | | | | | | | | |
| N | 15 | 15 | 15 | 15 | 15 | 15 | 15 | 15 |
| Mean | 14.67 | 1.47 | 294 | 39 | 1349 | 1654 | 1917 | 1957 |
| SD | 4.7 | 0.79 | 100 | 16 | 455 | 558 | 630 | 648 |
| Min | 7.14 | 0.5 | 159 | 18 | 698 | 874 | 1078 | 1092 |
| Median | 12.8 | 1 | 257 | 41 | 1282 | 1597 | 1885 | 1895 |
| Max | 24.22 | 3 | 476 | 63 | 2133 | 2513 | 3057 | 3227 |
| CV % | 32 | 53.9 | 34 | 41 | 34 | 34 | 34 | 33 |
| Geo. Mean | 14 | 1.28 | 279 | 36 | 1277 | 1564 | 1818 | 1856 |
| CI 95% Lower | 11.75 | 0.94 | 233 | 28 | 1052 | 1285 | 1505 | 1536 |
| CI 95% Upper | 16.68 | 1.74 | 335 | 46 | 1549 | 1902 | 2197 | 2243 |

TABLE 23

Study 1 PK Results

|  | $T_{1/2}$ | $T_{max}$ | $C_{max}$ | $C_{12}$ | $AUC_{0-12}$ | $AUC_{0-24}$ | $AUC_{last}$ | $AUC_{\infty}$ |
|---|---|---|---|---|---|---|---|---|
| Capsule | | | | | | | | |
| N | 16 | 16 | 16 | 16 | 16 | 16 | 16 | 16 |
| Mean | 10 | 1.09 | 568 | 51 | 2104 | 2473 | 2690 | 2699 |
| SD | 3 | 0.46 | 228 | 16 | 581 | 692 | 773 | 111 |
| Min | 6 | 0.5 | 288 | 32 | 1363 | 1589 | 1705 | 1715 |
| Median | 10 | 1 | 472 | 49 | 1945 | 2287 | 2587 | 2608 |
| Max | 18 | 2 | 965 | 85 | 3276 | 3874 | 4187 | 4199 |
| CV % | 34 | 41.6 | 40 | 31 | 28 | 28 | 29 | 29 |
| Geo. Mean | 10 | 1.01 | 527 | 49 | 2036 | 2390 | 2594 | 2603 |
| CI 95% Lower | 8 | 0.8 | 426 | 41 | 1771 | 2075 | 2242 | 2249 |
| CI 95% Upper | 12 | 1.26 | 652 | 57 | 2339 | 2753 | 3002 | 3013 |
| Tablet | | | | | | | | |
| N | 16 | 16 | 16 | 16 | 16 | 16 | 16 | 16 |
| Mean | 10 | 2.03 | 461 | 60 | 2202 | 2626 | 2848 | 2858 |
| SD | 3 | 0.94 | 110 | 15 | 335 | 451 | 544 | 553 |
| Min | 6 | 0.5 | 348 | 38 | 1809 | 2035 | 2115 | 2112 |
| Median | 11 | 2 | 425 | 63 | 2160 | 2585 | 2834 | 2847 |
| Max | 16 | 4 | 709 | 96 | 2979 | 3749 | 4184 | 4209 |
| CV % | 30 | 46.2 | 24 | 26 | 15 | 17 | 19 | 19 |
| Geo. Mean | 10 | 1.83 | 450 | 59 | 2180 | 2593 | 2803 | 2812 |
| CI 95% Lower | 8 | 1.4 | 400 | 51 | 2018 | 2378 | 2545 | 2550 |
| CI 95% Upper | 11 | 2.38 | 506 | 67 | 2356 | 2828 | 3087 | 3101 |
| Tablet + PPI | | | | | | | | |
| N | 15 | 15 | 15 | 15 | 15 | 15 | 15 | 15 |
| Mean | 14 | 2.9 | 139 | 38 | 923 | 1245 | 1561 | 1598 |
| SD | 5 | 1.38 | 31 | 8 | 180 | 259 | 454 | 490 |
| Min | 7 | 0.5 | 84 | 24 | 607 | 782 | 901 | 906 |
| Median | 12 | 3 | 142 | 41 | 925 | 1279 | 1457 | 1485 |
| Max | 26 | 4 | 186 | 51 | 1144 | 1674 | 2688 | 2861 |
| CV % | 37 | 47.5 | 22 | 22 | 20 | 21 | 29 | 31 |
| Geo. Mean | 13 | 2.33 | 136 | 37 | 905 | 1218 | 1503 | 1535 |
| CI 95% Lower | 11 | 1.48 | 120 | 33 | 806 | 1076 | 1284 | 1305 |
| CI 95% Upper | 16 | 3.68 | 155 | 43 | 1017 | 1379 | 1759 | 1804 |

Figure 19A:
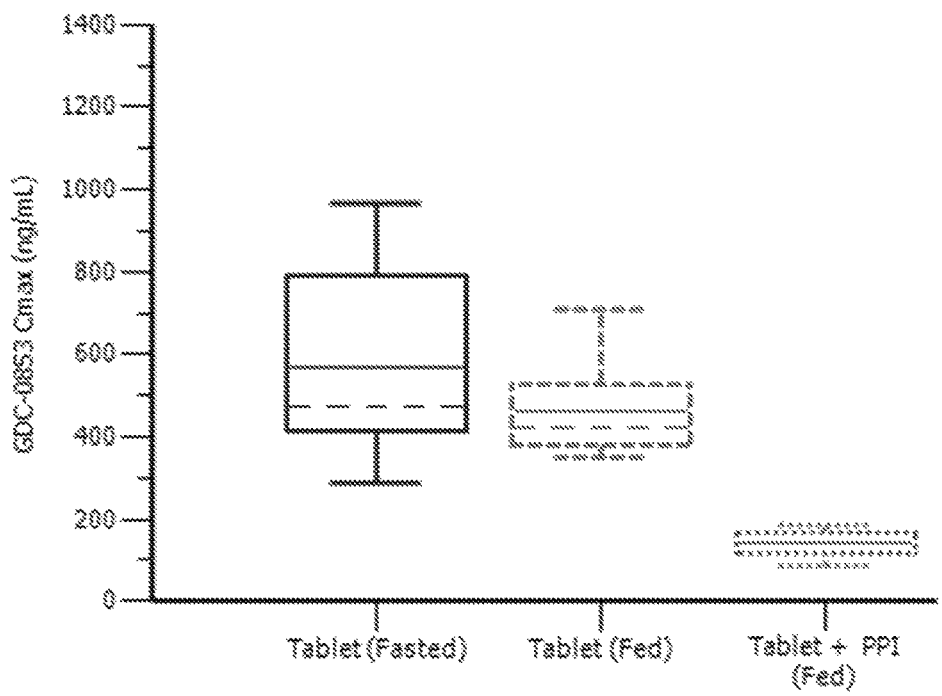
FIG. 19A provides a graph of human in vivo plasma Cmax (ng/mL) for a 200 mg tableted dose of compound (I) free base in combination with fumaric acid in a 1:1 wt. % ratio under fasted conditions, under fed conditions, and under fed conditions wherein the subject was administered 20 mg Rabeprazole (PPI) twice per day (BID).
Figure 19B:
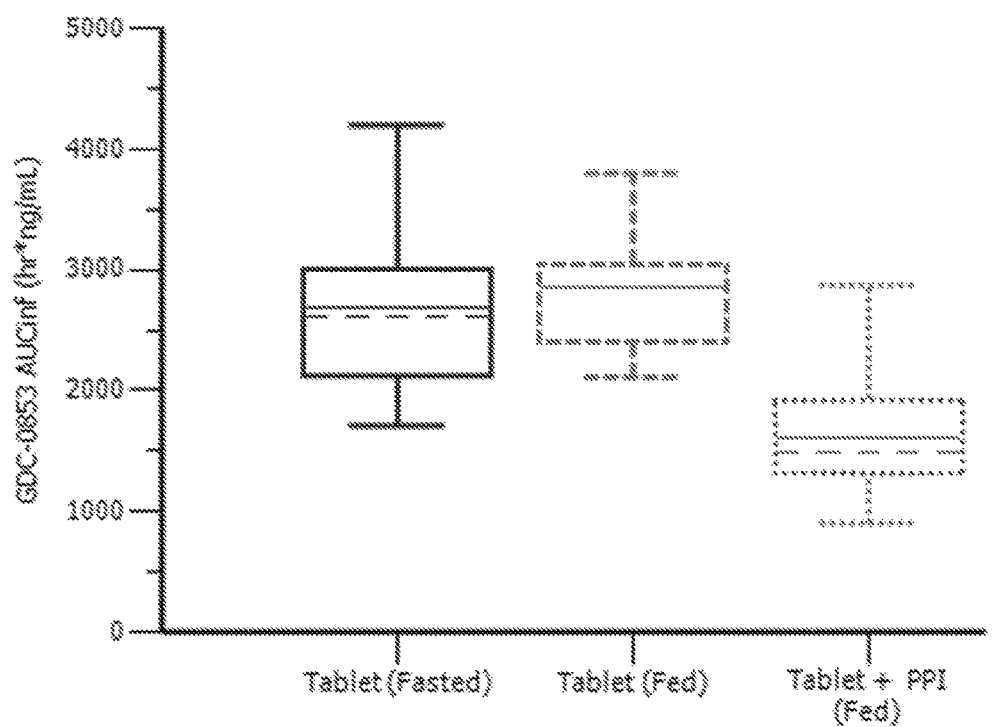
FIG. 19B provides a graph of human in vivo plasma AUCinf (hr*ng/mL) for a 200 mg tableted dose of compound (I) free base in combination with fumaric acid in a 1:1 wt. % ratio under fasted conditions, under fed conditions, and under fed conditions wherein the subject was administered 20 mg Rabeprazole (PPI) twice per day (BID).
Figure 20A:
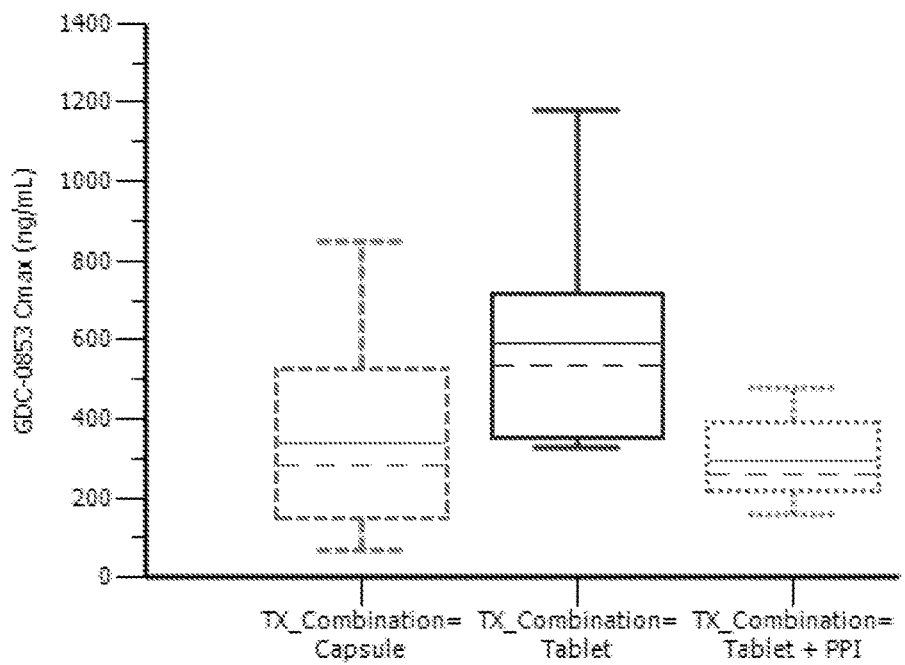
FIG. 20A provides a graph of human in vivo plasma Cmax (ng/mL) for: (i) a 200 mg powder-in-capsule dose of compound (I) free base in the absence of excipients and in the absence of fumaric acid, (ii) a 200 mg tableted dose of compound (I) free base comprising a 1:1 weight ratio of fumaric acid, and (iii) and a 200 mg tableted dose of compound (I) free base comprising at 1:1 weight ratio of fumaric acid, wherein the subject was administered 20 mg Rabeprazole (PPI) twice per day (BID).
Figure 20B:
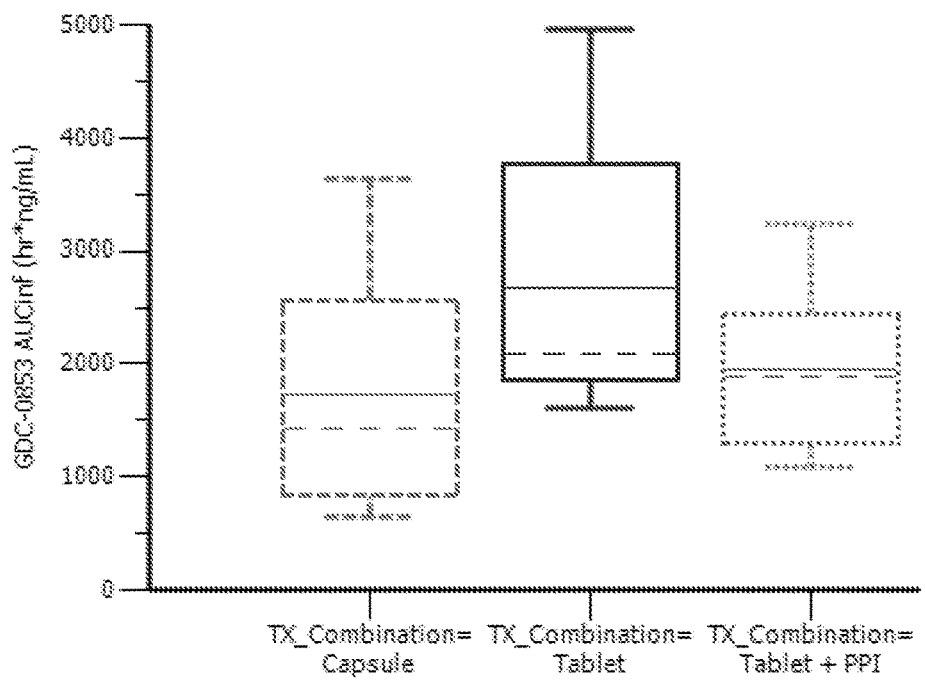
FIG. 20B provides a graph of human in vivo plasma AUCinf (hr*ng/mL) for: (i) a 200 mg powder-in-capsule dose of compound (I) free base in the absence of excipients and in the absence of fumaric acid, (ii) a 200 mg tableted dose of compound (I) free base comprising a 1:1 weight ratio of fumaric acid, and (iii) and a 200 mg tableted dose of compound (I) free base comprising at 1:1 weight ratio of fumaric acid, wherein the subject was administered 20 mg Rabeprazole (PPI) twice per day (BID).

Plasma concentration $C_{max}$ (ng/mL) linear scale results for Tablets (fasted), Tablets (Fed) and Tablets (Fed+PPI) are presented in FIG. 19A. Plasma $AUC_{inf}$ (hr*mg/mL) linear scale results for Tablets (fasted), Tablets (Fed) and Tablets (Fed+PPI) are presented in FIG. 19B. Plasma concentration $C_{max}$ (ng/mL) linear scale results for Capsules (fasted), Tablets (fasted) and Tablets (fasted+PPI) are presented in FIG. 20A. Plasma $AUC_{inf}$ (hr*mg/mL) linear scale results for Capsules (fasted), Tablets (fasted) and Tablets (fasted+PPI) are presented in FIG. 20B.

In second-comparative-study, a single dose food and PPI PK assessment was done for PIC dosage form compositions containing only 100 mg compound (I) free base (i.e., in the absence of fumaric acid and excipients). The protocol is detailed Table 24 below wherein each panel contained 10 human subjects.

TABLE 24

| Panel | PPI | Food/Fast | Compound (I) PIC Dose |
|---|---|---|---|
| J | None | Fasted Day 1 | 100 mg Day 1 |
| K | None | High Fat Breakfast Day 1 | 100 mg Day 1 |
| L | Rabeprazole (20 mg BID at −3 to day 1) | Fasted Day 1 | 100 mg Day 1 |
| M | Rabeprazole (20 mg BID at −3 to day 1) | High Fat Breakfast Day 1 | 100 mg Day 1 |

The results for plasma $C_{max}$ (µM), plasma $AUC_{inf}$ (hr*µM), plasma $AUC_{0-24}$ (hr*µM), plasma HL-Lambda-z (hr), plasma $T_{max}$ (hr) and plasma $AUC_{last}$ (hr*µM) are presented in Table 25 below.

TABLE 25

| Panel | | $C_{max}$ | $AUC_{inf}$ | $AUC_{0-24}$ | Lambda_z | $T_{max}$ | $AUC_{last}$ |
|---|---|---|---|---|---|---|---|
| J | N | 10 | 10 | 10 | 10 | 10 | 10 |
| | Mean | 0.218 | 1.07 | 0.967 | 16 | 1.5 | 1.06 |
| | SD | 0.153 | 0.635 | 0.608 | 7.6 | 0.236 | 0.633 |
| | Min | 0.043 | 0.31 | 0.23 | 7.3 | 1 | 0.31 |
| | Median | 0.2 | 1.1 | 0.98 | 13 | 1.5 | 1 |
| | Max | 0.46 | 2 | 1.9 | 29 | 2 | 2 |
| | CV % | 69.93 | 59.16 | 62.82 | 47.44 | 15.71 | 59.98 |
| K | N | 10 | 10 | 10 | 10 | 10 | 10 |
| | Mean | 0.235 | 1.7 | 1.56 | 9.82 | 4 | 1.69 |
| | SD | 0.0839 | 0.641 | 0.59 | 2.85 | 0.816 | 0.644 |
| | Min | 0.054 | 0.72 | 0.58 | 5 | 3 | 0.72 |
| | Median | 0.25 | 1.6 | 1.5 | 9.7 | 4 | 1.6 |
| | Max | 0.36 | 2.8 | 2.6 | 16 | 6 | 2.8 |
| | CV % | 35.71 | 37.69 | 37.91 | 29.05 | 20.41 | 38.06 |
| L | N | 10 | 10 | 10 | 10 | 10 | 10 |
| | Mean | 0.0116 | 0.274 | 0.157 | 12.8 | 5.7 | 0.261 |
| | SD | 0.0039 | 0.0599 | 0.0365 | 4.91 | 6.45 | 0.0489 |
| | Min | 0.0056 | 0.2 | 0.09 | 7.6 | 3 | 0.2 |
| | Median | 0.012 | 0.27 | 0.16 | 11 | 4 | 0.27 |
| | Max | 0.019 | 0.41 | 0.22 | 21 | 24 | 0.35 |
| | CV % | 33.3 | 21.82 | 23.2 | 38.4 | 113.11 | 18.71 |
| M | N | 10 | 10 | 10 | 10 | 10 | 10 |
| | Mean | 0.0406 | 0.657 | 0.471 | 13.4 | 6.9 | 0.642 |
| | SD | 0.0112 | 0.188 | 0.118 | 5.85 | 2.51 | 0.188 |
| | Min | 0.026 | 0.3 | 0.25 | 7.5 | 3 | 0.3 |
| | Median | 0.04 | 0.67 | 0.52 | 12 | 7 | 0.66 |
| | Max | 0.062 | 0.87 | 0.57 | 26 | 12 | 0.85 |
| | CV % | 27.64 | 28.68 | 25.03 | 43.63 | 36.44 | 29.34 |

The ratios of PK parameters by panels J to M are presented in Table 26 below where "J" refers to Panel J (Fast), "K" refers to Panel K (Fed), "L" refers to Panel L (Fast+Rabeprazole PPI), and "M" refers to Panel M (Fed+Rabeprazole PPI).

TABLE 26

| Parameter | N | J | K | L | M | K/J | L/J | M/J | M/L |
|---|---|---|---|---|---|---|---|---|---|
| $AUC_{inf}$ | 10 | 1.073 | 1.701 | 0.274 | 0.657 | 1.585 | 0.256 | 0.612 | 2.395 |
| $C_{max}$ | 10 | 0.218 | 0.235 | 0.012 | 0.041 | 1.076 | 0.053 | 0.186 | 3.487 |

Figure 21A:
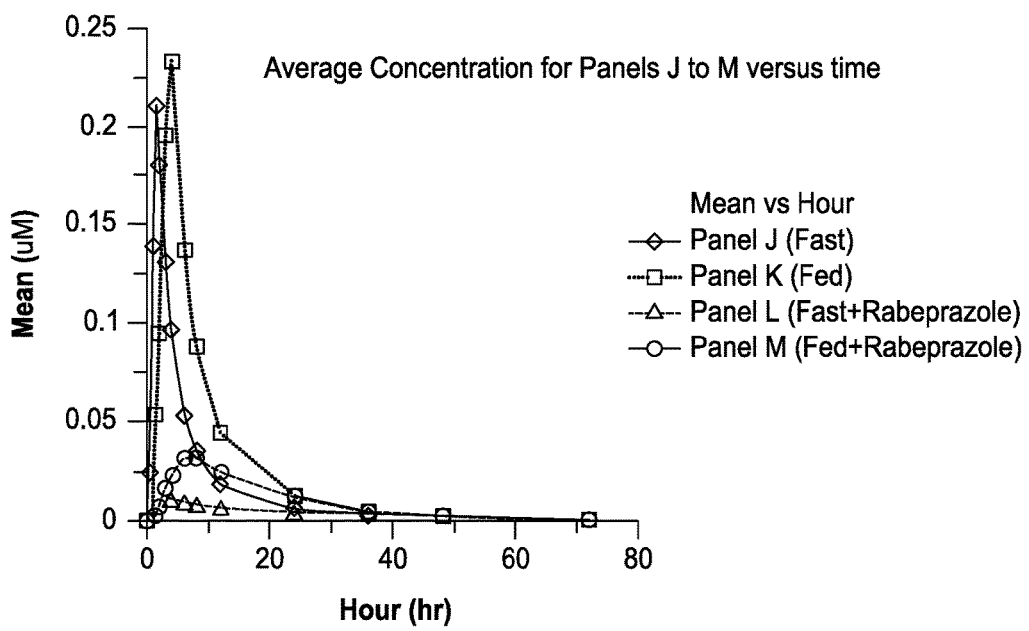
FIG. 21A provides a graph of human in vivo plasma concentration (ng/mL) versus time for a dose of a powder-in-capsule containing 100 mg compound (I) free base in the absence of excipients and in the absence of fumaric acid under (i) fasted conditions, (ii) fed conditions, (iii) fasted conditions wherein the subject was administered 20 mg Rabeprazole (PPI) twice per day (BID) for three days prior to, and on the day of, compound (I) dosing, and (iv) fed conditions wherein the subject was administered 20 mg Rabeprazole (PPI) twice per day (BID) for three days prior to, and on the day of, compound (I) dosing.
Figure 21B:
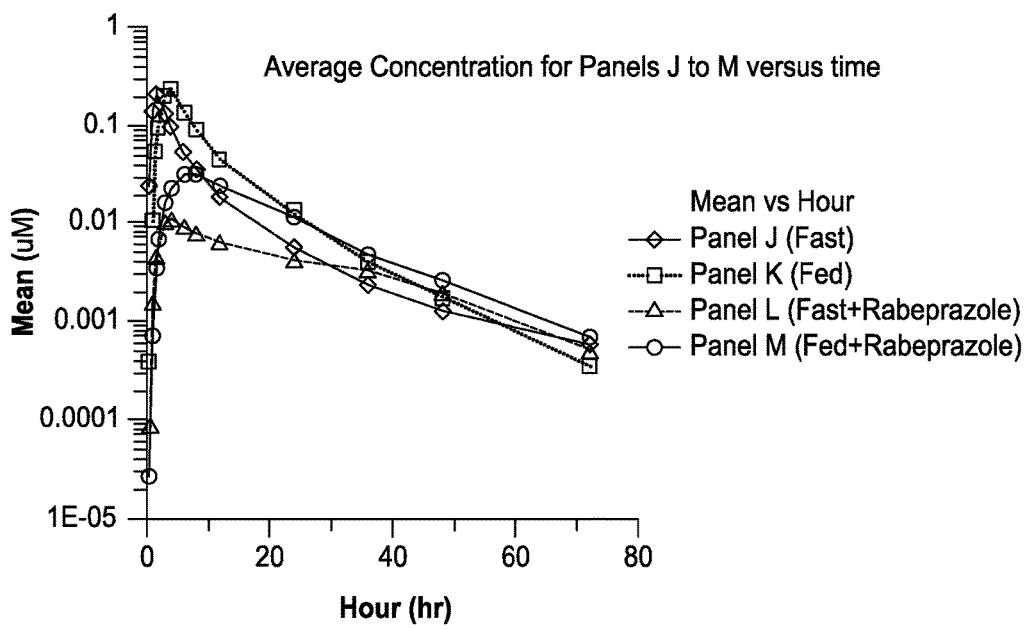
FIG. 21B provides a graph of human in vivo plasma concentration (ng/mL, logarithmic scale) versus time for a dose of powder-in-capsule containing 100 mg compound (I) free base in the absence of excipients and in the absence of fumaric acid under fasted conditions, under fed conditions, and under (i) fasted conditions, (ii) fed conditions, (iii) fasted conditions wherein the subject was administered 20 mg Rabeprazole (PPI) twice per day (BID) for three days prior to, and on the day of, compound (I) dosing, and (iv) fed conditions wherein the subject was administered 20 mg Rabeprazole (PPI) twice per day (BID) for three days prior to, and on the day of, compound (I) dosing.
Figure 22A:
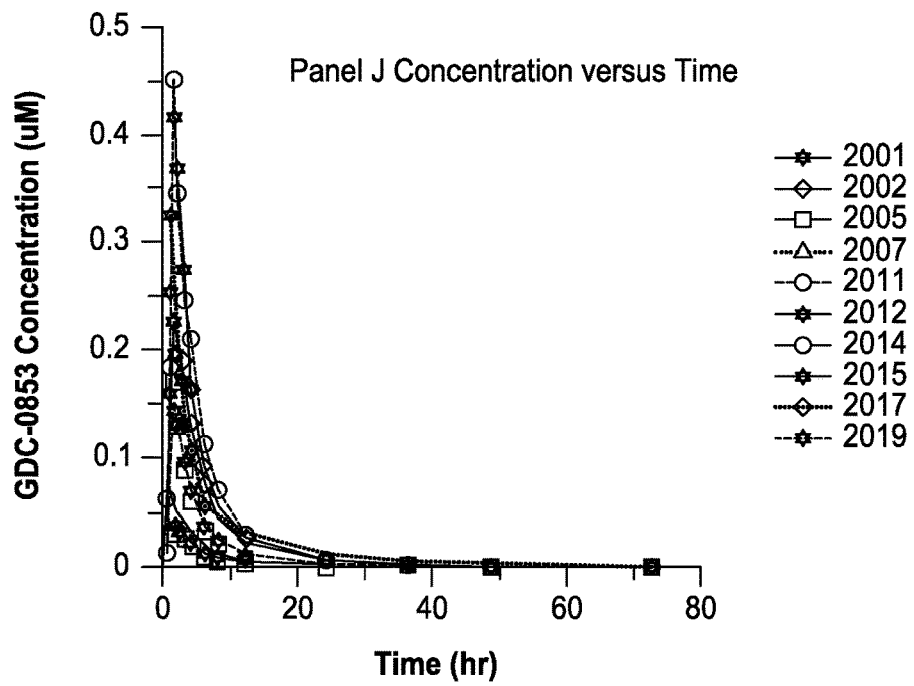
FIG. 22A provides a graph of human in vivo plasma concentration (ng/mL) versus time for a dose of a powder-in-capsule containing 100 mg compound (I) free base in the absence of excipients and in the absence of fumaric acid under fasted conditions.
Figure 22B:
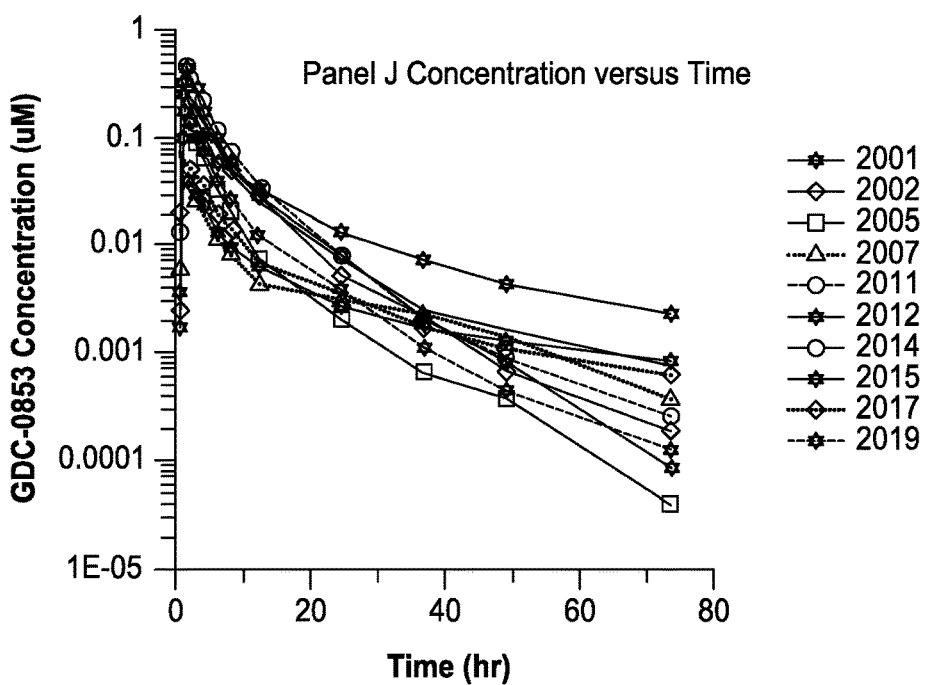
FIG. 22B provides a graph of human in vivo plasma concentration (ng/mL, logarithmic scale) versus time for a dose of a powder-in-capsule containing 100 mg compound (I) free base in the absence of excipients and in the absence of fumaric acid under fasted conditions.
Figure 23A:
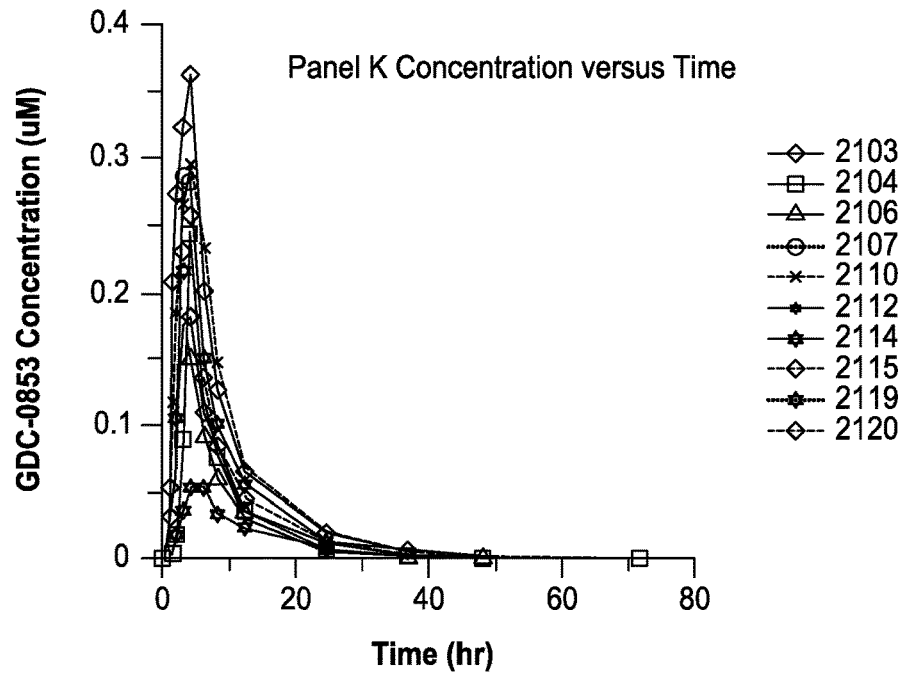
FIG. 23A provides a graph of human in vivo plasma concentration (ng/mL) versus time for a dose of a powder-in-capsule containing 100 mg compound (I) free base in the absence of excipients and in the absence of fumaric acid under fed conditions.
Figure 23B:
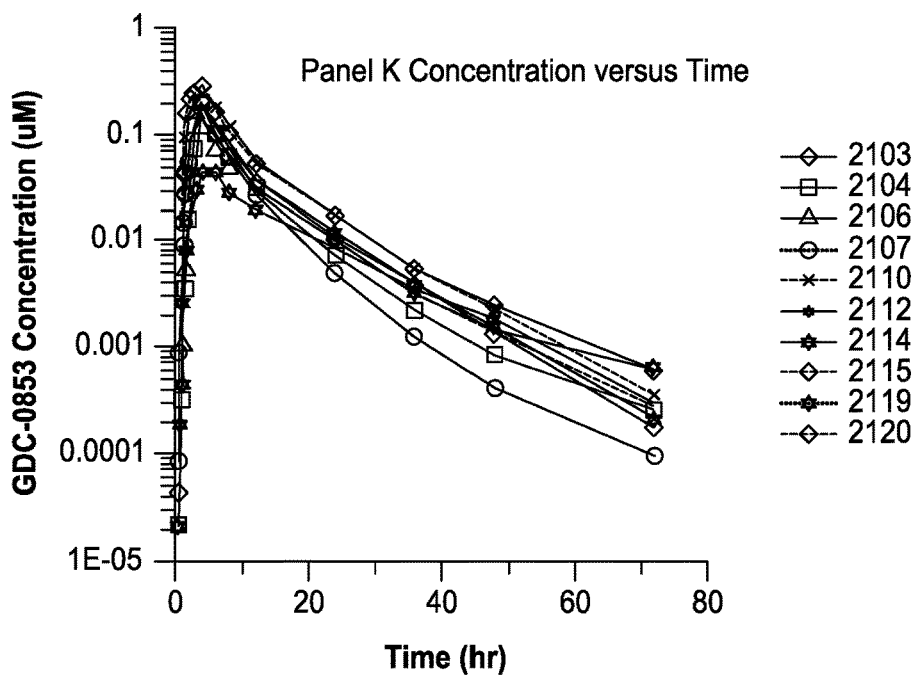
FIG. 23B provides a graph of human in vivo plasma concentration (ng/mL, logarithmic scale) versus time for a dose of a powder-in-capsule containing 100 mg compound (I) free base in the absence of excipients and in the absence of fumaric acid under fed conditions.
Figure 24A:
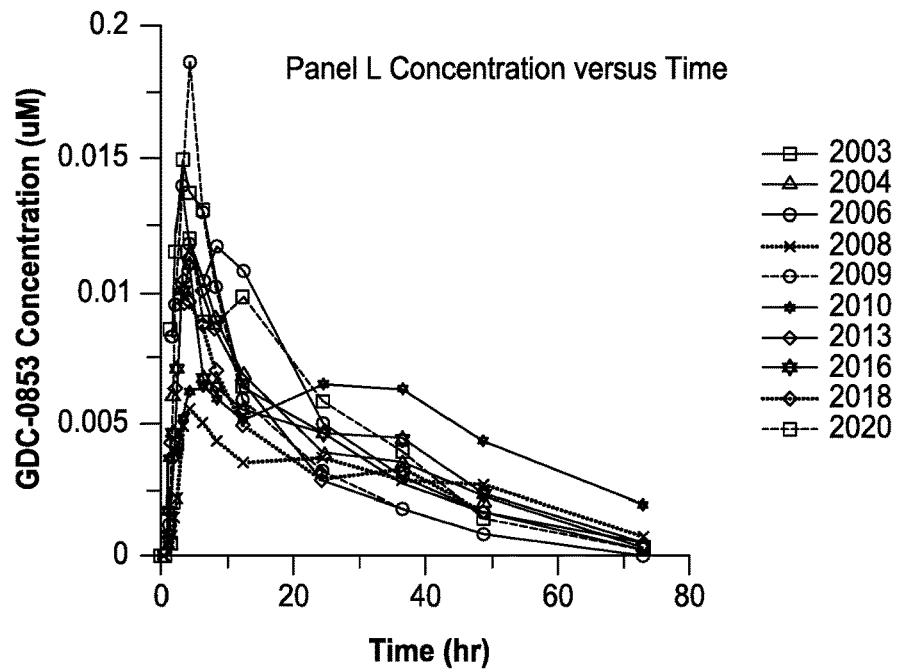
FIG. 24A provides a graph of human in vivo plasma concentration (ng/mL) versus time for a dose of a powder-in-capsule containing 100 mg compound (I) free base in the absence of excipients and in the absence of fumaric acid under fasted conditions wherein the subject was administered 20 mg Rabeprazole (PPI) twice per day (BID) for three days prior to, and on the day of, compound (I) dosing.
Figure 24B:
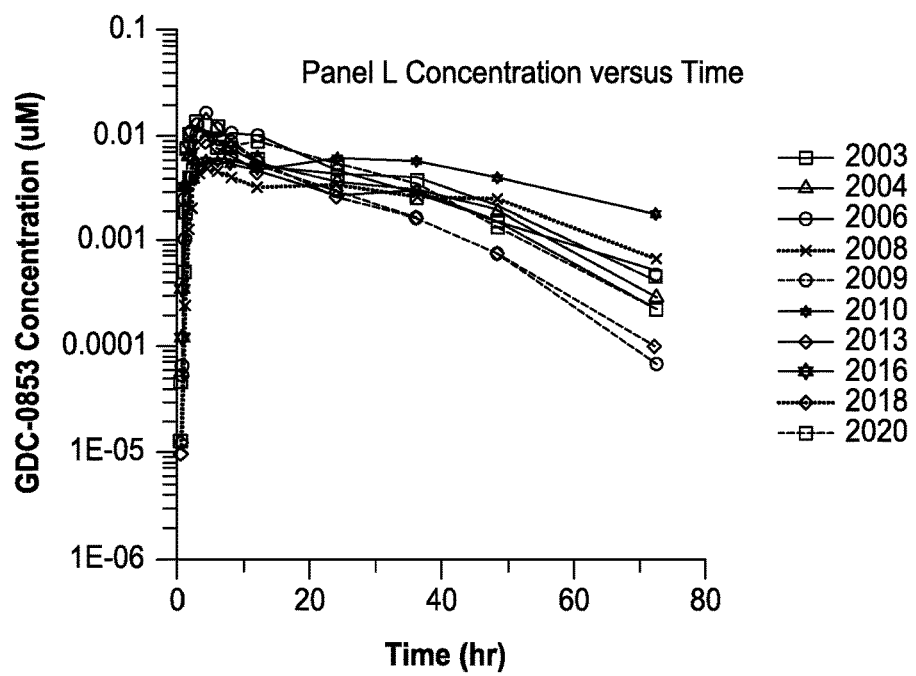
FIG. 24B provides a graph of human in vivo plasma concentration (ng/mL, logarithmic scale) versus time for a dose of a powder-in-capsule containing 100 mg compound (I) free base in the absence of excipients and in the absence of fumaric acid under fasted conditions wherein the subject was administered 20 mg Rabeprazole (PPI) twice per day (BID) for three days prior to, and on the day of, compound (I) dosing.
Figure 25A:
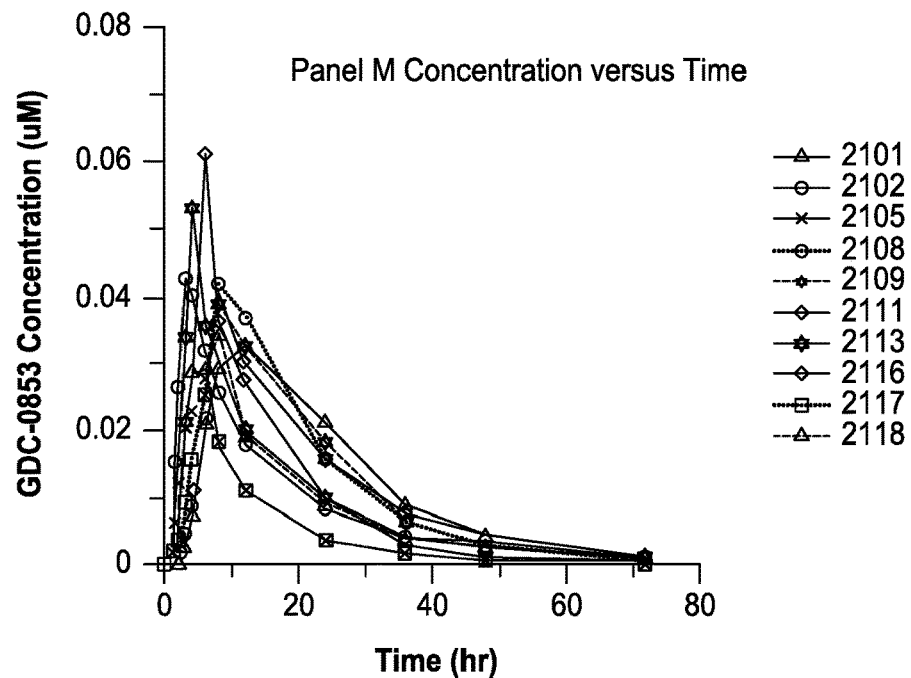
FIG. 25A provides a graph of human in vivo plasma concentration (ng/mL) versus time for a dose of a powder-in-capsule containing 100 mg compound (I) free base in the absence of excipients and in the absence of fumaric acid under fed conditions wherein the subject was administered 20 mg Rabeprazole (PPI) twice per day (BID) for three days prior to, and on the day of, compound (I) dosing.
Figure 25B:
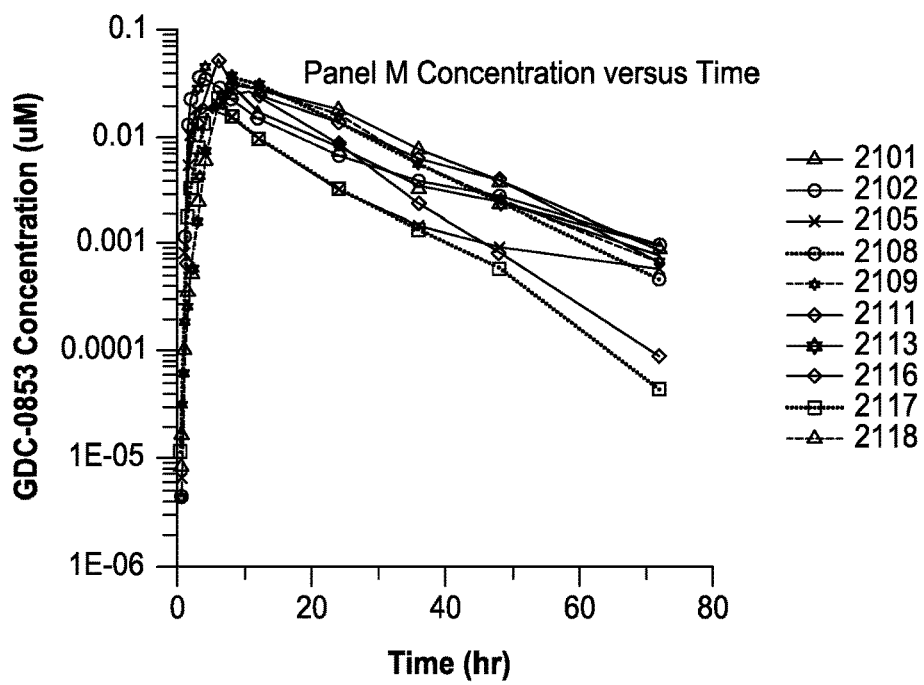
FIG. 25B provides a graph of human in vivo plasma concentration (ng/mL, logarithmic scale) versus time for a dose of a powder-in-capsule containing 100 mg compound (I) free base in the absence of excipients and in the absence of fumaric acid under fed conditions wherein the subject was administered 20 mg Rabeprazole (PPI) twice per day (BID) for three days prior to, and on the day of, compound (I) dosing.
Figure 26A:
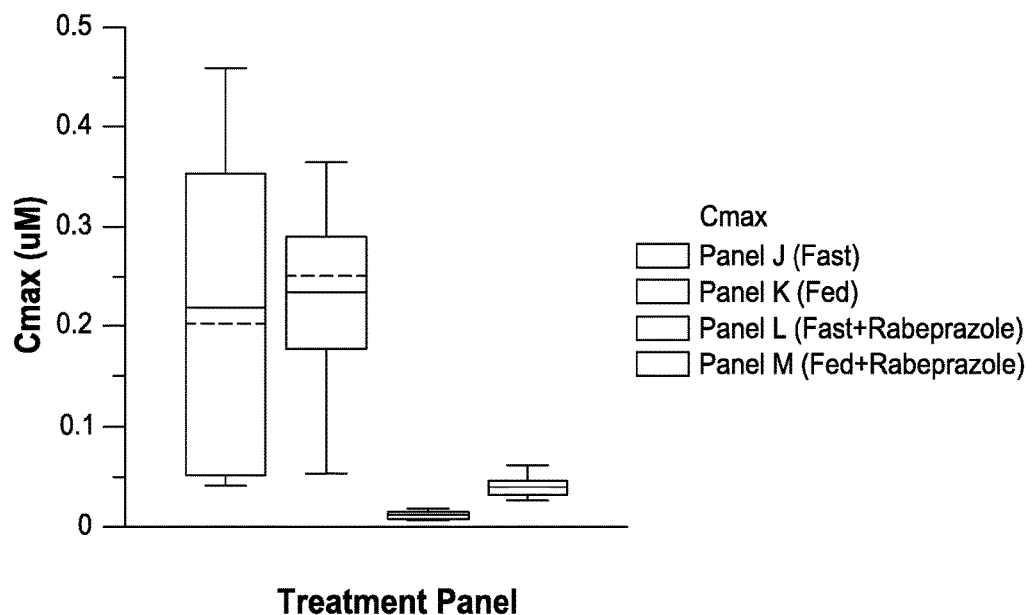
FIG. 26A provides a graph of human in vivo plasma Cmax (ng/mL) for a dose of a powder-in-capsule containing 100 mg compound (I) free base in the absence of excipients and in the absence of fumaric acid under (i) fasted conditions, (ii) fed conditions, (iii) fasted conditions wherein the subject was administered 20 mg Rabeprazole (PPI) twice per day (BID) for three days prior to, and on the day of, compound (I) dosing, and (iv) fed conditions wherein the subject was administered 20 mg Rabeprazole (PPI) twice per day (BID) for three days prior to, and on the day of, compound (I) dosing.
Figure 26B:
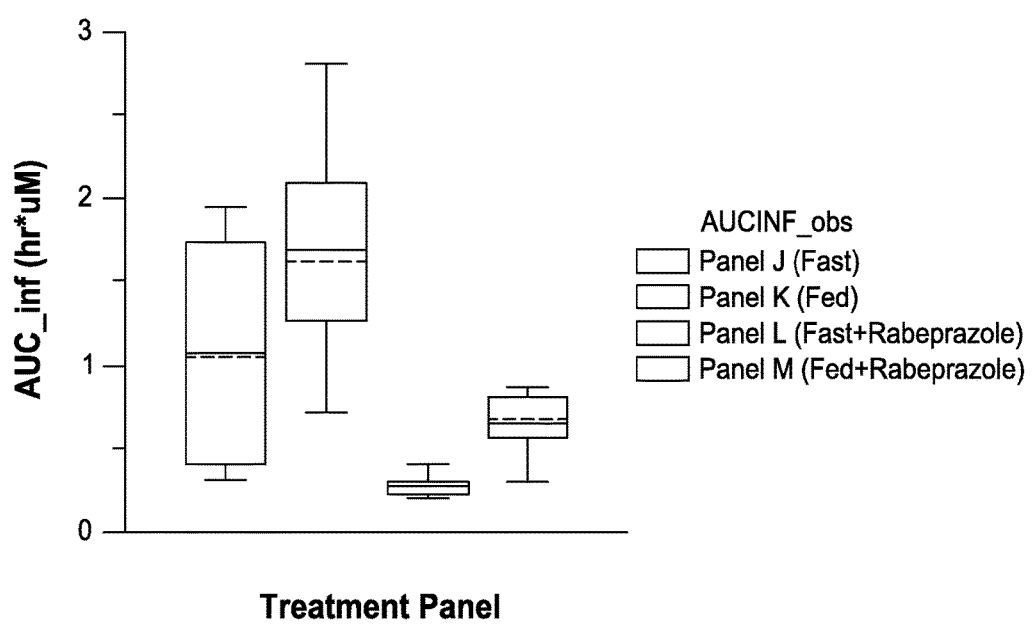
FIG. 26B provides a graph of human in vivo plasma AUCinf (hr*ng/mL) for a dose of a powder-in-capsule containing 100 mg compound (I) free base in the absence of excipients and in the absence of fumaric acid under (i) fasted conditions, (ii) fed conditions, (iii) fasted conditions wherein the subject was administered 20 mg Rabeprazole (PPI) twice per day (BID) for three days prior to, and on the day of, compound (I) dosing, and (iv) fed conditions wherein the subject was administered 20 mg Rabeprazole (PPI) twice per day (BID) for three days prior to, and on the day of, compound (I) dosing.

The comparative results for the mean concentration (µM) for panels J to M versus time (hr) are presented in FIG. 21A (linear scale) and 21B (log scale). Plasma concentration (µM) comparative results for individuals in panel J versus time (hr) are presented in FIGS. 22A (linear scale) and 22B (log scale). Plasma concentration (µM) comparative results for individuals in panel K versus time (hr) are presented in FIGS. 23A (linear scale) and 23B (log scale). Plasma concentration (µM) comparative results for individuals in panel L versus time (hr) are presented in FIG. 24A (linear scale) and 24B (log scale). Plasma concentration (µM) comparative results for individuals in panel M versus time (hr) are presented in FIGS. 25A (linear scale) and 25B (log scale). Plasma concentration comparative $C_{max}$ (µM) linear scale results for Panel J (Fast), Panel K (Fed), Panel L (Fast+Rabeprazole PPI) and Panel M (Fed+Rabeprazole PPI) are presented in FIG. 26A. Plasma comparative $AUC_{inf}$ (hr*µM) linear scale results for Panel J, Panel K, Panel L and Panel M are presented in FIG. 26B.

The second (comparative) Example 8 study results for PIC compound (I) free base dosed in the absence of fumaric acid indicate high variability in fasting subjects and a large decrease in compound (I) exposure when a PPI is taken. In contrast, the combination of compound (I) free base and fumaric acid from the first Example 8 study showed reduced variability in fasting subjects and maintenance of therapeutic compound (I) exposure when a PPI is taken.

Example 9

Preparation of Tablets Comprising Compound (I) Free Base and Fumaric Acid

The tablets comprised the components detailed in Table 27. The tablets were prepared as follows: The intra-granular components were blended. The intra-granular blend was slugged using a Carver press and then milled by mortar and pestle to form compound (I) free base intra-granules. The intra-granules were then blended with the extra-granular components to form a tablet blend. The tablet blend was compressed to form tablets using a Carver press.

TABLE 27

| Component | Description | wt. % | Tablet 1 mg/tablet | wt. % | Tablet 2 mg/tablet |
|---|---|---|---|---|---|
| Intra-granular | | | | | |
| Compound (I) Free Base | API | 20.0 | 200.0 | 25.0 | 200.0 |
| Lactose monohydrate | Fast Flo 316 | 10.0 | 100.0 | 10.0 | 80.0 |
| Microcrystalline cellulose | Avicel PH-102 | 45.5 | 455.0 | 35.5 | 284.0 |
| Croscarmellose sodium | Ac-Di-Sol | 1.5 | 15.0 | 1.5 | 12.0 |
| Magnesium stearate | Hyqual 2257 | 0.5 | 5.0 | 0.5 | 4.0 |
| Extra-granular | | | | | |
| Fumaric acid | Powder Special, Pharma Grade | 20.0 | 200.0 | 25.0 | 200.0 |
| Croscarmellose sodium | Ac-Di-Sol | 1.5 | 15.0 | 1.5 | 12.0 |
| Magnesium stearate | Hyqual 2257 | 1.0 | 10.0 | 1.0 | 10.0 |
| Tablet Core Total | | 100.0 | 1000.0 | 100.0 | 800.0 |

Example 10

Preparation of Compound (I) Amorphous and Crystalline Chloride Salts

Figure 27:
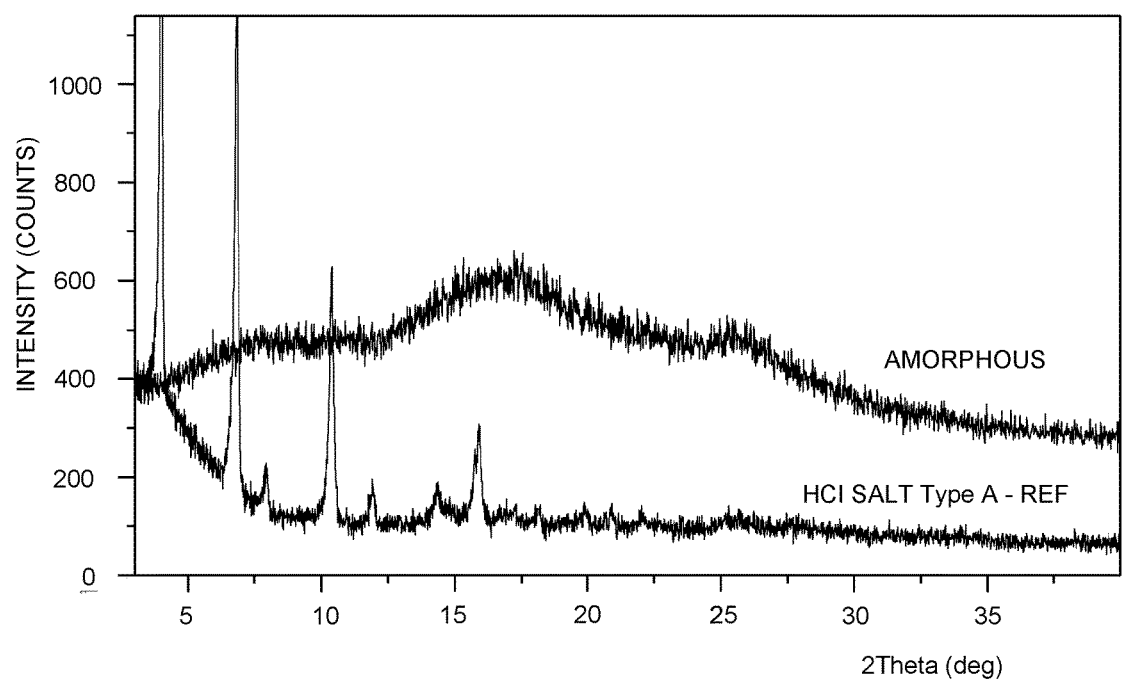
FIG. 27 provides an overlay of XRPD patterns of compound (I) chloride Type A crystals and compound (I) amorphous chloride salt.

The amorphous chloride salt of compound (I) was prepared as follows. Concentrated HCl (37%) was diluted to 0.2 M with dichloromethane ("DCM"). About 200 mg of compound (I) free base Type A was added to a 20 mL glass vial to which 1.5 mL DCM was added to generate a clear solution. Sufficient HCl/DCM solution (1.52 mL) was added drop wise to provide a molar ratio of compound (I) free base to HCl of 1:1.1. About 2 mg of compound (I) chloride salt type A polymorph seed crystal was added to the vial as seed whereupon 1 mL of ethyl acetate was added thereby resulting in an admixture having a cloudy appearance. The admixture was stirred at room temperature for 1 day and the solids were then isolated by centrifugation and dried at room temperature. The solids were collected and analyzed by HPLC for purity and by XRPD. Purity by HPLC was determined to be 99.8% and having a stoichiometry of 1. The XRPD results for the amorphous chloride salt and the crystalline chloride type A salt are depicted in FIG. 27 as compared to a compound (I) crystalline chloride type A salt reference.

Figure 28:
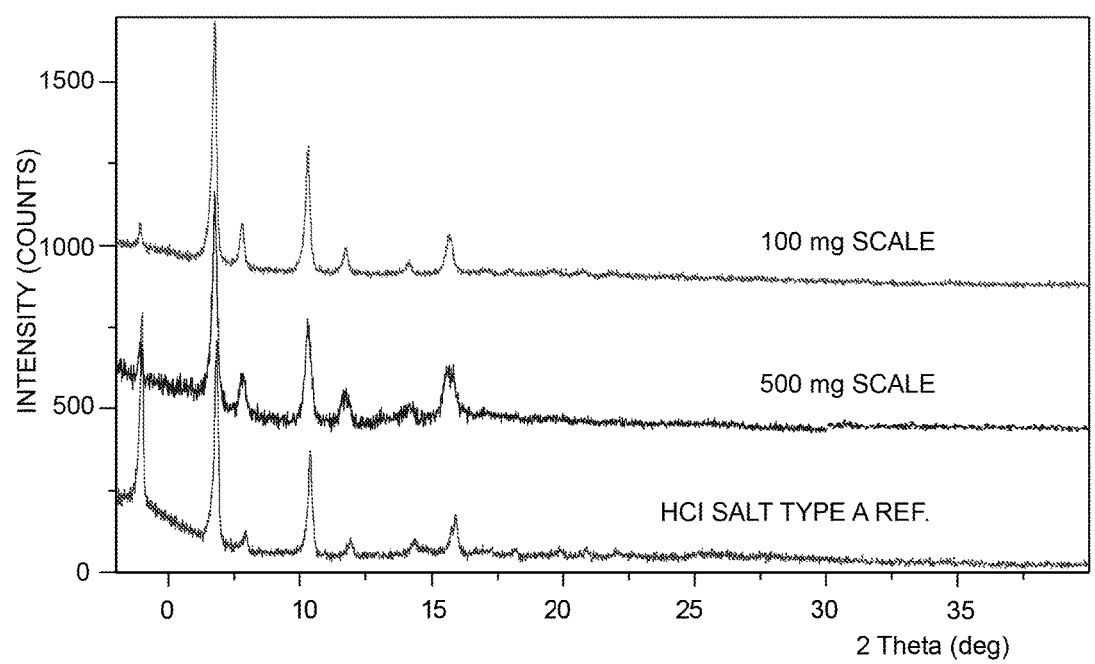
FIG. 28 provides an overlay of powder XRPD patterns of compound (I) chloride Type A crystals (i) prepared at 100 mg scale in according to a first aspect of the disclosure and (ii) prepared at 500 mg scale in according to a second aspect of the disclosure as compared to compound (I) chloride Type A crystal standard.
Figure 29:
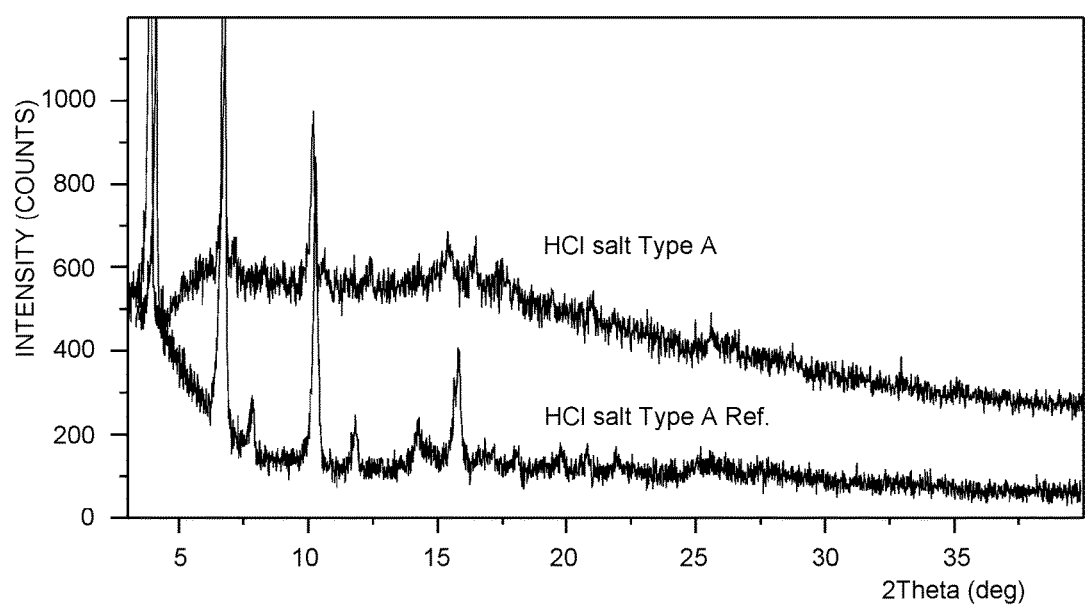
FIG. 29 provides an overlay of powder XRPD patterns of compound (I) chloride salt Type A crystals prepared according to a third aspect of the disclosure as compared to compound (I) chloride salt Type A crystal standard.

In a first evaluation for preparing compound (I) chloride salt type A polymorph, concentrated HCl (37%) was diluted to 0.2 M with tetrahydrofuran ("THF"). 100 mg of compound (I) free base Type A was added to a 20 mL glass vial to which 1.5 mL of THF/H$_2$O (19:1, v/v) was added to generate a clear solution. Dilute HCl was added to the free base solution in increments of 170 L until the stoichiometric ratio of compound (I) to HCl reached 1.1. About 8 mg of compound (I) chloride salt type A polymorph seed crystal thereby resulting in an admixture. The admixture was stirred at room temperature for 1 day and the solids were then isolated by centrifugation and dried at room temperature. The solids were collected and analyzed by HPLC for purity and by XRPD. Purity by HPLC was determined to be 99.41% and having a stoichiometry of 1. In a second evaluation for preparing compound (I) chloride salt type A polymorph, concentrated HCl (37%) was diluted to 0.2 M with THF/H$_2$O (19:1, v/v). About 500 mg of compound (I) free base was added to a 20 mL glass vial to which 7.5 mL of THF/H$_2$O (19:1, v/v) was added to generate a clear solution. A total of 4.1 mL of the 0.2 M HCl was added to the free base solution drop-wise until the stoichiometric ratio of compound (I) to HCl reached 1.1. About 8 mg of compound (I) chloride salt type A polymorph seed crystal thereby resulting in an admixture. The admixture was stirred at room temperature for 18 hours and the solids were then isolated by centrifugation and dried at room temperature. The solids were collected and analyzed by HPLC for purity and by XRPD. Purity by HPLC was determined to be 99.74% and having a stoichiometry of 1. The XRPD results for the 100 mg and 500 mg scale compound (I) crystalline chloride type A salt preparations as compared to compound (I) crystalline chloride type A salt reference are depicted in FIG. 28.

In a third evaluation for preparing compound (I) chloride salt type A polymorph, about 20 mg compound (I) free base Type A was combined with 0.5 mL ACN in a glass vial. About 0.17 mL of 0.2 M HCl in ethanol was added in a molar charge ratio of free base to acid of 1:1.1. About 2 mg compound (I) chloride salt Type A was seed added to the vial to form an admixture. The admixture was stirred at 5° C. for about 2 days. The solids were then isolated by centrifugation and dried at room temperature. The solids were collected and analyzed by HPLC for purity and by XRPD. Purity by HPLC was determined to be 99.04% and have a stoichiometry of 1. The XPRD results are presented in FIG. 29. XRPD peak data for the compound (I) chloride salt type A polymorph is recited in Table 28.

TABLE 28

Compound (I) chloride salt type A polymorph XRPD data

| Pos. [° 2Th.] | Height [cts] | FWHM Left [° 2Th.] | d-spacing [Å] | Rel. Int. [%] |
|---|---|---|---|---|
| 3.973 | 791.424 | 0.0895 | 22.240 | 95.67 |
| 6.831 | 827.242 | 0.1023 | 12.94 | 100.00 |
| 7.917 | 387.033 | 0.1023 | 11.167 | 46.79 |
| 10.458 | 376.445 | 0.1151 | 8.459 | 45.51 |
| 11.865 | 313.483 | 0.1023 | 7.459 | 37.89 |
| 14.209 | 214.622 | 0.1023 | 6.234 | 25.94 |
| 15.793 | 798.100 | 0.1151 | 5.611 | 96.48 |
| 17.018 | 82.976 | 0.5117 | 5.21 | 10.03 |
| 18.096 | 95.793 | 0.154 | 4.902 | 11.58 |
| 19.758 | 161.731 | 0.1279 | 4.493 | 19.55 |
| 20.891 | 49.5 | 0.2047 | 4.252 | 5.98 |
| 22.0313 | 51.738 | 0.307 | 4.035 | 6.25 |
| 25.225 | 59.497 | 0.307 | 3.531 | 7.19 |

Example 11

Preparation of Compound (I) Crystalline Sulfate Salts

Compound (I) sulfate salt type A polymorph was prepared according to the following method. About 0.9 g of compound (I) free base Type A was combined with 4.6 mL DCM in a 10 mL crystallizer followed by stirring at about 20° C. to obtain a clear solution. 7.44 mL of 0.2 M H2SO4 was added stepwise over 0.5 hours with stirring. The contents were transferred to a second 100 mL crystallizer to remove gel-like material. The solution was heated to 35° C. followed by addition of 5.5 mL ACN. 100 mg of compound (I) sulfate salt type A seed was added to form a cloudy admixture. The admixture was stirred at 35° C. for 0.5 hours and 60 mL of ACN was added over 12 hours. Thereafter, the admixture was cooled to 20° C. over 2 hours and then stirred at 20° C. for 3 hours. The crystals were isolated by filtration and washed with 2 mL ACN. The wet crystals were dried at 45° C. under vacuum for 4 hours. The solids were collected providing 1.1 g with a yield of about 87.9%. The crystals were characterized by XRPD (FIG. 30), TGA/DSC, $^1$H NMR and HPLC. TGA results indicated a weight loss of 9.1% up to 100° C. DSC results indicated three endotherms at 138.0° C., 216.8° C. and 272.0° C. (peak temperature). $^1$H NMR results indicated 5.8% ACN residual in compound (I) sulfate type A. HPLC results indicated 99.48% purity.

Figure 31:
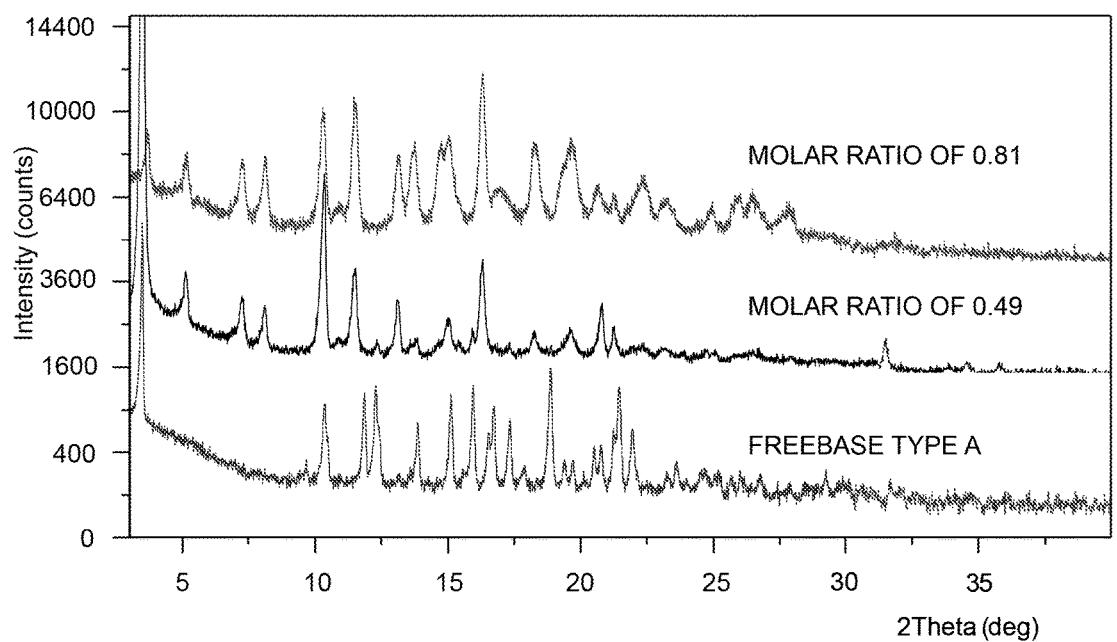
FIG. 31 provides an overlay of powder XRPD patterns of compound (I) sulfate salt Type A crystals prepared from compound (I) free base and sulfuric acid at mole ratios of free base to acid of 0.49:1 and 0.81:1 as compared to compound (I) free base.

Stoichiometry of sulfate formation was evaluated wherein two batches of compound (I) sulfate type A were prepared as described elsewhere herein and at molar ratios of compound (I) free base to sulfate anion of 0.49:1 and 0.81:1. Unreacted free base type A was observed from the batch prepared at the mole ratio of 0.49:1 suggesting that compound (I) sulfate type A is more likely to be a mono-sulfate salt. The XRPD results are presented in FIG. 31. XRPD peak data for the compound (I) sulfate salt type A polymorph is recited in Table 29.

TABLE 29

Compound (I) sulfate salt type A polymorph XRPD data

| Pos. [° 2Th.] | Height [cts] | FWHM Left [° 2Th.] | d-spacing [Å] | Rel. Int. [%] |
| --- | --- | --- | --- | --- |
| 3.722 | 442.219 | 0.1151 | 23.741 | 52.28 |
| 5.17 | 366.646 | 0.1791 | 17.094 | 43.34 |
| 7.28 | 332.047 | 0.1535 | 12.143 | 39.25 |
| 8.115 | 353.807 | 0.1535 | 10.895 | 41.83 |
| 10.336 | 591.699 | 0.1535 | 8.559 | 69.95 |
| 11.525 | 628.358 | 0.2303 | 7.678 | 74.28 |
| 13.121 | 347.351 | 0.2047 | 6.748 | 41.06 |
| 13.755 | 425.278 | 0.1023 | 6.438 | 50.28 |
| 14.712 | 433.923 | 0.179 | 6.021 | 51.3 |
| 15.057 | 457.369 | 0.1791 | 5.884 | 54.07 |
| 16.294 | 845.897 | 0.1663 | 5.44 | 100 |
| 16.955 | 204.818 | 0.4093 | 5.229 | 24.21 |
| 18.282 | 429.418 | 0.307 | 4.853 | 50.76 |
| 19.736 | 406.63 | 0.307 | 4.498 | 48.07 |
| 20.596 | 211.892 | 0.2558 | 4.313 | 25.05 |
| 21.272 | 174.449 | 0.2047 | 4.177 | 20.62 |
| 22.356 | 246.142 | 0.4093 | 3.977 | 29.1 |
| 23.215 | 149.993 | 0.4093 | 3.832 | 17.73 |
| 24.935 | 118.488 | 0.2558 | 3.571 | 14.01 |
| 25.943 | 171.613 | 0.358 | 3.435 | 20.29 |
| 26.52 | 161.794 | 0.307 | 3.361 | 19.13 |
| 27.967 | 93.482 | 0.307 | 3.19 | 11.05 |
| 31.514 | 21.405 | 0.614 | 2.839 | 2.53 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A tablet composition comprising:
   (i) from about 25 mg to about 300 mg of a free base of structure (I):

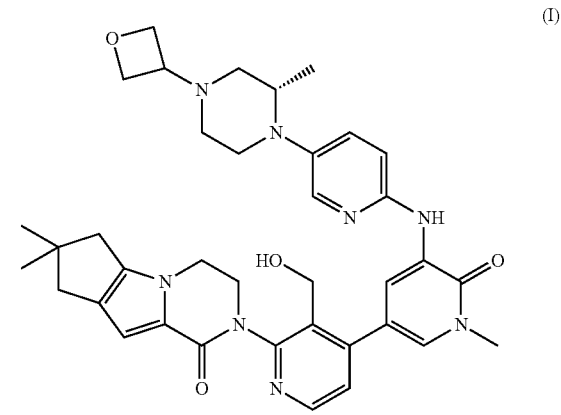 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

and
   (ii) fumaric acid, wherein the weight ratio of the free base of structure (I) to fumaric acid is from about 1:5 to about 3:1.

2. The composition of claim 1 wherein the compound (I) free base content is from about 100 mg to about 300 mg, and wherein the composition comprises from about 15 wt. % to about 30 wt. % compound (I) free base.

3. The composition of claim 1 wherein the fumaric acid content is from about 10 wt. % to about 30 wt. %.

4. The composition of claim 1 wherein the weight ratio of the compound (I) free base to fumaric acid is from about 1:2 to about 2:1.

5. The composition of claim 1 further comprising at least one pharmaceutically acceptable excipient selected from fillers, binders, disintegrants, lubricants and glidants.

6. The composition of claim 1 wherein the fumaric acid is present as an extra-granular component.

7. The composition of claim 5 comprising:
   (i) from about 20 wt. % to about 25 wt. % of the free base of structure (I);
   (ii) from about 15 wt. % to about 25 wt. % fumaric acid;
   (iii) filler;
   (iv) lubricant; and
   (v) from about 1 wt. % to about 5 wt. % disintegrant, wherein the weight ratio of the free base of structure (I) to fumaric acid is from about 1:1.5 to about 1.5:1.

8. The composition of claim 7 wherein the weight ratio of the free base of structure (I) to fumaric acid is from about 1:1.2 to about 1.2:1.

9. The composition of claim 7 wherein:
   (i) the tablet comprises and intra-granular component and an extra-granular component;
   (ii) the disintegrant is present as an intra-granular component and as an extra-granular component; and
   (iii) the fumaric acid is present as an extra-granular component.

10. The composition of claim 9 wherein:
    (i) the filler comprises lactose monohydrate and microcrystalline cellulose;
    (ii) the disintegrant comprises croscarmellose sodium; and
    (iii) the lubricant comprises magnesium stearate.

11. A method of treating a condition selected from immune disorders, cancer, cardiovascular disease, viral infection, inflammation, metabolism/endocrine function disorders and neurological disorders in an achlorhydric patient, the method comprising administering the pharmaceutical composition of claim 1 to a patient in need of such treatment.

\* \* \* \* \*